US009655377B2

(12) United States Patent
Xue et al.

(10) Patent No.: US 9,655,377 B2
(45) Date of Patent: May 23, 2017

(54) METHODS OF CONTROLLING FRUCTAN SYNTHESIS IN PLANTS

(75) Inventors: Gangping Xue, St Lucia (AU); Cathrine Lynne Mcintyre, Paddington (AU); Maarten Christiaan Kooiker, Indooroopilly (AU)

(73) Assignee: COMMONWEALTH SCIENTIFIC AND INDUSTRIAL RESEARCH ORGANISATION, Campbell (AU)

( * ) Notice: Subject to any disclaimer, the term of this patent is extended or adjusted under 35 U.S.C. 154(b) by 362 days.

(21) Appl. No.: 14/238,715

(22) PCT Filed: Aug. 10, 2012

(86) PCT No.: PCT/AU2012/000942
§ 371 (c)(1),
(2), (4) Date: Oct. 31, 2014

(87) PCT Pub. No.: WO2013/023243
PCT Pub. Date: Feb. 21, 2013

(65) Prior Publication Data
US 2015/0044349 A1 Feb. 12, 2015

Related U.S. Application Data

(60) Provisional application No. 61/523,050, filed on Aug. 12, 2011.

(51) Int. Cl.
| C12N 15/82 | (2006.01) |
| A23L 1/10 | (2006.01) |
| C07K 14/415 | (2006.01) |
| C12P 19/04 | (2006.01) |
| A23L 7/10 | (2016.01) |

(52) U.S. Cl.
CPC ..... *A23L 1/10* (2013.01); *A23L 7/10* (2016.08); *C07K 14/415* (2013.01); *C12N 15/8246* (2013.01); *C12P 19/04* (2013.01)

(58) Field of Classification Search
None
See application file for complete search history.

(56) References Cited

U.S. PATENT DOCUMENTS 7,214,786 B2 * 5/2007 Kovalic ............... C07K 14/415
530/324
7,425,666 B2 * 9/2008 da Costa e Silva . C07K 14/415
435/419
2006/0121157 A1 * 6/2006 Caspers ............... A21D 2/38
426/11
2007/0044171 A1 * 2/2007 Kovalic ............... C07K 14/415
800/278
2007/0214517 A1 9/2007 Alexandrov et al.
2009/0094717 A1 4/2009 Troukhan et al.
2010/0083407 A1 4/2010 Feldmann et al.
2011/0003697 A1 1/2011 Cahoon et al.
2011/0167514 A1 7/2011 Brover et al.
2011/0258735 A1 * 10/2011 Coffin ............... C12N 15/8247
800/275

FOREIGN PATENT DOCUMENTS

WO WO 2009/091518 A2 7/2009
WO WO 2010/124324 A1 11/2010

OTHER PUBLICATIONS

Kirik et al. The Plant Journal 13(6): 729-742 (1998).*
Xue et al. The Plant Journal 68: 857-870 (published online Sep. 19, 2011).*
Li et al. Journal of Experimental Botany 57(6): 1263-1273 (2006).*
Notification of Transmittal of the International Search Report and the Written Opinion of the International Searching Authority, or the Declaration, including an International Search Report and Written Opinion of the International Searching Authority, mailed Oct. 25, 2012 in connection with PCT International Application No. PCT/AU2012/000942, filed Aug. 10, 2012.
Notification Concerning Transmittal of International Preliminary Report on Patentability (Chapter I of the Patent Cooperation Treaty), including an International Preliminary Report on Patentability and Written Opinion of the International Searching Authority, mailed Feb. 27, 2014 by the International Bureau of WIPO in connection with PCT International Application No. PCT/AU2012/000942, filed Aug. 10, 2012.

* cited by examiner

*Primary Examiner* — David T Fox
(74) *Attorney, Agent, or Firm* — John P. White; Cooper & Dunham LLP

(57) ABSTRACT

The present invention relates to plants with increased levels of water soluble carbohydrates, particularly fructan, in the stem and leaf sheath. The present invention also provides methods of identifying and/or producing these plants. In particular, the present invention relates to a novel class of polypeptides designated MYB13 which upregulate the expression of enzymes involved in fructan synthesis. The present invention further relates to a novel promoter element that can be used to express genes predominantly in the stem and leaf sheath during the early reproductive stage of a plant.

8 Claims, 20 Drawing Sheets

Figure 3:
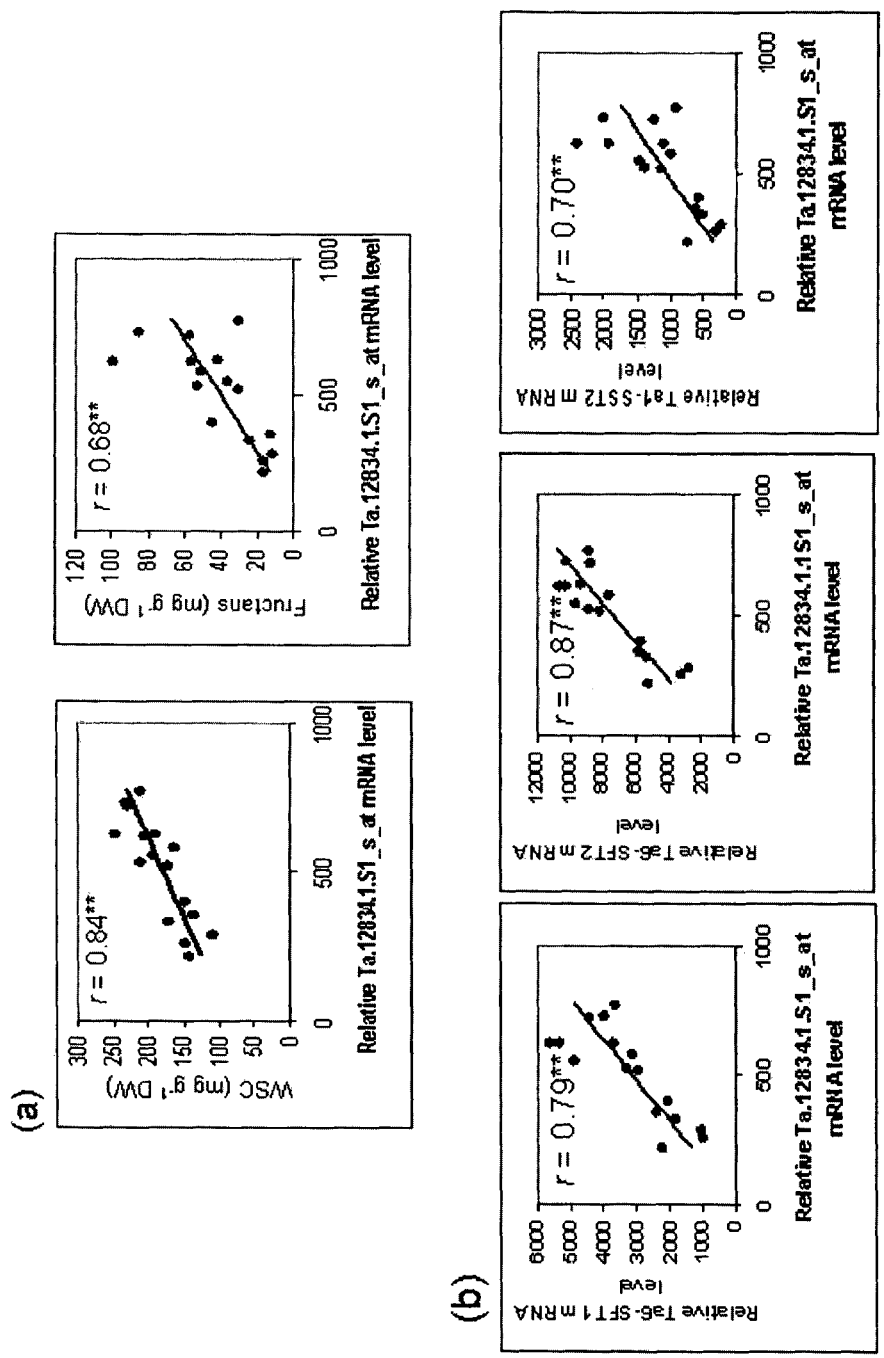

```
                                                                           80
TaMYB13-1  ATGAAGACGAAGCAGGCTTCCAAGGCCAAGGCGGCGCCCGTCGCCGGGGAAGGAGGAGGAAGCAGTTGCACCGGGTGGTTT
TaMYB13-2  ATGAAGACGAAGCAGGCTTCCAAGGCCAAGGCGGCGCCCGTCGCCGGGGAAGGAGGAGGAAGCAGTTGCACCGGGGGGTTT
TaMYB13-3  ATGAAGATGAAGCAGACGAAGAAGAC---GTCGGCGCCGTCGCCGGGCAAGCAGGAGGAGCAGTTGCACCCGGGGGTTT
                                                                          160
TaMYB13-1  CCGCAAGGGGCCATGGACGGAGCAGGAGGACATGAAGCTGGCGTGGTTCGTGCGGCTCTTCGGCGAGCGCCGCTGGGATT
TaMYB13-2  CCGGAAGGGGACCATGGACGGAGCAGGAGGACATGAAGCTGGCGTGGTTCGTGCGGCTCTTCGGCGAGCGCCGCTGGGATT
TaMYB13-3  CCGAAGGGGCCATGGACGGAGCAGGAGGACATGAAGCTGGCCTGGTTCGTGCGGCTCTTCGGCGAGCGCCGCTGGGATT
                                                                          240
TaMYB13-1  TCTTAGCTAAGGTGTCAGgtttgcaaggtggcgggtgaccatgccgtgccatgca---------tgcgcc--------
TaMYB13-2  TCTTAGCTAAGGTGTCAGgtttgcaaggtggcgggtgaccatgccgtgccatgcgatgccatgcgtgcgcctccacgca
TaMYB13-3  TCTTAGCTAAGGTGTCAGgtttgcaaggtggcgggtgaccatgccgtgccatgca---------tgcgc---------
                                                                          320
TaMYB13-1  ----atgcatgcatgcatgtctgggaccaaaatatgatgtagccatggtcctttgtgtgctaacgctctcggtctccgccg
TaMYB13-2  tgcatgcatgcaggccatgcatgggaccaaaatatgatgtagccatggtcctttgtgtgctaacgctctcggtctccgccg
TaMYB13-3  ----atgcatgcatgcatgtctgggaccaaa-taacatgtagccatggtcctttgtgtgctaacgctctcggtctccgccg
                                                                          400
TaMYB13-1  ----gcacctcttgctcttgtgtttgcttggcgacagGTCTTAACCGGACGGGAAGAGCTGCCGGCTCCGGTGGGTCA
TaMYB13-2  tccggcacctccgctcttgtgtctgccttgcctacagGTCTCAACCGGACGGGGAAGAGCTGCCGGCTCCGGTGGGTCA
TaMYB13-3  ----gcacctcttgctcttgtgtctgcctggctacagGTCTCAACCGGACGGGAAGAGCTGCCGGCTCCGGTGGGTCA
                                                                          480
TaMYB13-1  ACTACCTGCACCCGGACCTCAAGCGCGGCCGGATGAGCCCCGAAGAGGAGCGCCTCGTCGTCGACCTCCACGCCCGCTGG
TaMYB13-2  ACTACCTGCACCCGGACCTCAAGCGCGGCCGGATGAGCCCCGAAGAGGAGCGCCTCGTCGTCGACCTCCACGCCCGCTGG
TaMYB13-3  ACTACCTGCACCCGGACCTGAAGCGCGGCCGGATGAGCCCCGACGAGGAGCGCCTCGTCGTCGACCTCCACGCCCGCTGG
                                                                          560
TaMYB13-1  GGCAACCGCTGGTCACGGATCGCCAAGGCCATGCCGGGGCGCACCGACAACGAGATCAAGAACTACTGGCGCACCCACAC
TaMYB13-2  GGCAACCGCTGGTCCCGCATCGCCAAGGCCATGCCGGGCCGCACCGACAACGAGATCAAGAACTACTGGCGCACCCACAC
TaMYB13-3  GGCAACCGCTGGTCCCGCATCGCCAAGGCCATGCCGGGGCGCACCGACAACGAGATCAAGAACTACTGGCGCACCCACAC
                                                                          640
TaMYB13-1  CCGCAAGCTCCACAAGGACACGCGCGCC---TCTGCTG---------CTTCGGCCTCTACGACCACG------TCCACGT
TaMYB13-2  CCGCAAGCTCCACAAGGACACGCGCGCCGCCTCTGCTG---------CTTCGGCCTCCACGACCACGACCACGTCCACGT
TaMYB13-3  CCGCAAGCTCCACAAGGACGCGCGCGCCGCCGCCGCGGACGGCGCCTCTGCTGCTTCTGCCTCCACGACCACGTCCACGT
                                                                          720
TaMYB13-1  CCATGTCGGCGGCGTCTCCGGCCACCACGTCCAGCTCCTCCTCTTC---AACGATCGACAACGACAACAACTCACATCAC
TaMYB13-2  CCATGTCGGCGGCGTCTCCGGCCACCACGTCCAGCTCCTCCTCCTCAACGAACGACAACGATAACCACTCGCATCAC
TaMYB13-3  CCATGTCGGCGGCGTCTCCGGCCACCACGTCCAGCTCCTCCTCCTC---AACAAACGACAACCACAACCACTTGCATCAC
                                                                          800
TaMYB13-1  GGCCACCGCGACCAAGAGACGGCGGCCAGCCAGGAACAAGCGGATAACCAGCTGCTCTACACCGCCGGCATCGGCATGGA
TaMYB13-2  GGCCACCGCGACCAAGAGACGGCGGCCAGCCAGGAACAAGCAGATCACCAGCTGCTCTACACCTCCGGCATCGGCATGGA
TaMYB13-3  GGCCACGGCGACCAAGAGACGGCGGCCAGCCAGGAACAAGCGGATAACCAGCTGCTCTACACCGCCGGCATCGGCATGGA
                                                                          880
TaMYB13-1  CAGCCACCTCCTTTGGAACGACGCCATCATGGACTCCTACGCATGGGGAGCCGCCGTGCCGTCGATGATAGTGCCGCCGC
TaMYB13-2  CAGCCACCTCCTTTGGAACGACGCCCTCATGGACTCCTACGCCATGGGGAGCGGCCGCCGCCGTCTATGATAGTGCCGCCGC
TaMYB13-3  CAGCCACCTCCTTTGGAACGACGCCATCATGGACTCTTACGCATGGGGAGCGGCCGCCGCCGTCCATGTTAGTGCCGCCGC
                                                                          960
TaMYB13-1  CTTCATCGCCGGTGTGGGACTACTGCTGCTCGGATTCGCTCTGGGGGATAGGCGACGACGAGGTCGAGTACAAGAAGATG
TaMYB13-2  CTTCATCGCCGGTGTGGGACTACTGCTGCTCGGATTCGCTCTGGGGAATAGGTGACGACGAGGTCGAGTACAAGAAGATG
TaMYB13-3  CTTCATCGCCGGTGTGGGACTACTGCTGCTCGGATTCGCTCTGGGGGATAGGCGACGACGAGGTCGAGTACAAGAAGATG
                                                                          984
TaMYB13-1  CTCGCCGTCGCCGGTGCCTCATGA
TaMYB13-2  CTCGCCGTCGCCGGTGCCTCATGA
TaMYB13-3  CTCGCCGTCGCCGGTGCCTCATGA
```

Figure 1

(a) Transactivation of fructosyltransferase promoter-driven reporters
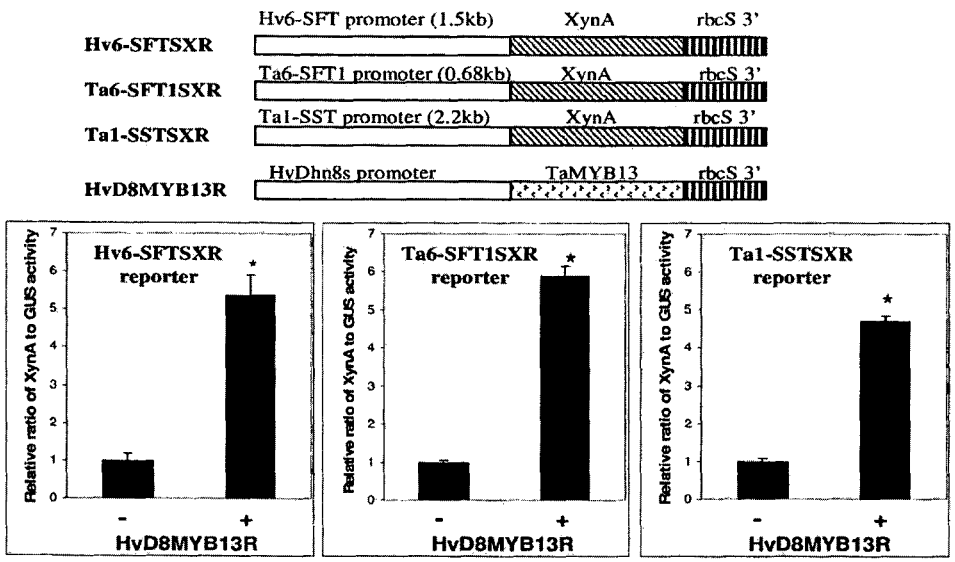
(b) Fructosyltransferase promoter truncation and point-mutation
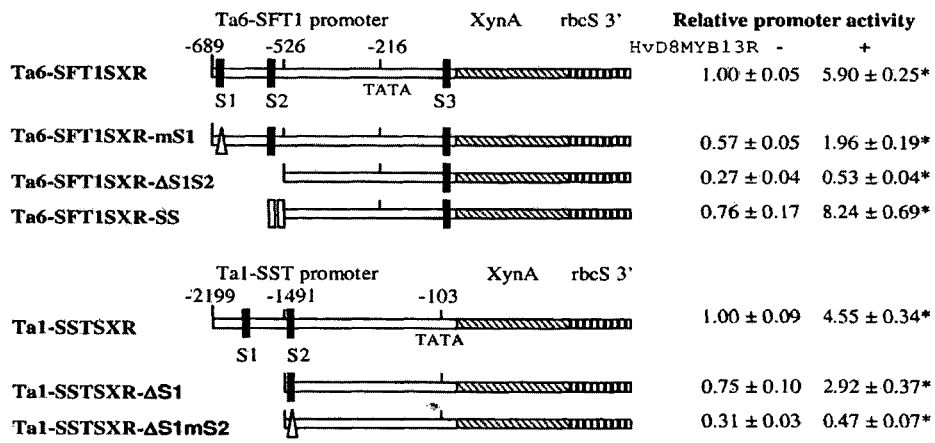
Figure 2

TaMYB13 proteins encoded by correctly spliced transcript forms

```
            1                                                                         80
TaMYB13-1   MKTKQASKAKAAPSPGKEEEAVAPGGFRKGPWTEQEDMKLAWFVRLFGERRWDFLAKVSGLNRTGKSCRLRWVNYLHPDL
TaMYB13-2   MKTKQASKAKAAPSPGKEEEAVAPGGFRKGPWTEQEDMKLAWFVRLFGERRWDFLAKVSGLNRTGKSCRLRWVNYLHPDL
TaMYB13-3   MKMKQTKKT-SAPSPGKQEEAVAPGGFRKGPWTEQEDMKLAWFVRLFGERRWDFLAKVSGLNRTGKSCRLRWVNYLHPDL 81                                                                        160
TaMYB13-1   KRGRMSPEEERLVVDLHARWGNRWSRIAKAMPGRTDNEIKNYWRTHTRKLHKDTRA-SA---ASASTTT--STSMSAASP
TaMYB13-2   KRGRMSPEEERLVVDLHARWGNRWSRIAKAMPGRTDNEIKNYWRTHTRKLHKDTRAASA---ASASTTTTTSTSMSAASP
TaMYB13-3   KRGRMSPDEERLVVDLHARWGNRWSRIAKAMPGRTDNEIKNYWRTHTRKLHKDARAAAADGASAASASTTTSTSMSAASP 161                                                                       240
TaMYB13-1   ATTSSSSSS-TIDNDNNSHHGHRDQETAASQEQADNQLLYTAGIGMDSHLLWNDAIMDSYAWGAAVPSMIVPPPSSPVWD
TaMYB13-2   ATTSSSSSSSTNDNDNHSHHGHGDQETAASQEQADHQLLYTSGIGMDSHLLWNDALMDSYAWGAAAPSMIVPPPSSPVWD
TaMYB13-3   ATTSSSSSS-TNDNHNHLHHGHGDQETAASQEQADNQLLYTAGIGMDSHLLWNDAIMDSYAWGAAAPSMLVPPPSSPVWD 241              267
TaMYB13-1   YCCSDSLWGIGDDEVEYKKMLAVAGAS
TaMYB13-2   YCCSDSLWGIGDDEVEYKKMLAVAGAS
TaMYB13-3   YCCSDSLWGIGDDEVEYKKMLAVAGAS
```

TaMYB13 proteins encoded by the transcripts containing an unspliced intron

```
            1                                                                 65
TaMYB13-1   MKTKQASKAKAAPSPGKEEEAVAPGGFRKGPWTEQEDMKLAWFVRLFGERRWDFLAKVSglqggg
TaMYB13-2   MKTKQASKAKAAPSPGKEEEAVAPGGFRKGPWTEQEDMKLAWFVRLFGERRWDFLAKVSglqggg
TaMYB13-3   MKMKQTKKT-SAPSPGKQEEAVAPGGFRKGPWTEQEDMKLAWFVRLFGERRWDFLAKVSglqggg
```

Figure 4

(a)

```
TaMYB13-1   MKTKQASKAKA-APSPGKEEEAVAPGGFRKGPWTEQEDMKLAWFVRLFGE  50
HvMYB13     MKMKQASKAKATATSPGKEDEAVAPGGFRKGPWTEQEDMKLAWFVRLFGE

TaMYB13-1   RRWDFLAKVSGLNRTGKSCRLRWVNYLHPDLKRGRMSPEEERLVVDLHAR  100
HvMYB13     RRWDFLAKVSGLNRTGKSCRLRWVNYLHPDLKRGRMTPDEERLVVDLHAR

TaMYB13-1   WGNRWSRIAKAMPGRTDNEIKNYWRTHTRKLHKDTRA--------SAASA  150
HvMYB13     WGNRWSRIAKAMPGRTDNEIKNYWRTHTRKLHKDTRAVAAADGSGSAASA

TaMYB13-1   STTT-STSMSAASPATTSSSSSSTIDNDNNSHH---GHRDQETAAS----  200
HvMYB13     STTTTSTSMSPASPATTSSSSSSTTDNDNHSHHHGHGHHDQETAASCQEQ

TaMYB13-1   QEQADNQLLYTAGIGMDSHLLWND-AIMDSYAWGA-AVPSMIVPPPSSPV  250
HvMYB13     QQAAEQQLFYTSVGAMDSHLLWNDDAMLDSYAWGATALPSMIVPPPSSPV

TaMYB13-1   WDYCCSDSLWGIGDDEVEYKKMLAVAGAS  279
HvMYB13     WDYCCSDSLWGIGDDEVEYKKMLAVAGAS
```

(b)

```
AtMYB48        NRKGPWTEQEDILLVNFVHLFGDRRWDFIAKVSGLNRTGKSCRLRWVNYLHPG
AtMYB59        YRKGPWTEQEDILLVNFVHLFGDRRWDFVAKVSGLNRTGKSCRLRWVNYLHPG
Os11g47460.1   MRKGPWTEQEDLQLVCTVRLFGDRRWDFVAKVSGLNRTGKSCRLRWVNYLHPG
Os12g37970.1   IRKGPWTEQEDLQLVCTVRLFGERRWDFIAKVSGLNRTGKSCRLRWVNYLHPG
TaMYB13-1      FRKGPWTEQEDMKLAWFVRLFGERRWDFLAKVSGLNRTGKSCRLRWVNYLHPD
HvMYB13        FRKGPWTEQEDMKLAWFVRLFGERRWDFLAKVSGLNRTGKSCRLRWVNYLHPD
Os01g74410.1   MRKGPWTEQEDVQLVWFVRLLGERR-DFLAKVSGLQRSGKSCRLRWVNYLHPG
               **********: *.  *:*:*:** **:*****:*:*************.

AtMYB48        LKRGKMTPQEERLVLELHAKW-NRWSKIARKLPGRTDNEIKNYWRTHMRKK
AtMYB59        LKRGKMTPQEERLVLELHAK-GNRWSKIARKLPGRTDNEIKNYWRTHMRKK
Os11g47460.1   LKHGRMSPKEEHLIIELHAR-GNRWSRIARRLPGRTDNEIKNYWRTHMRKK
Os12g37970.1   LKRGRMSPHEERLILELHAR-GNRWSRIARRLPGRTDNEIKNYWRTHMRKK
TaMYB13-1      LKRGRMSPEEERLVVDLHARWGNRWSRIAKAMPGRTDNEIKNYWRTHTRKL
HvMYB13        LKRGRMTPDEERLVVDLHARWGNRWSRIAKAMPGRTDNEIKNYWRTHTRKL
Os01g74410.1   LKRGRMSPEEERMVVQLHAKLGNRWSRIAKSIPGRTDNEIKNYWRTHLRKL
               **:*:*.*.**:::::***:   ****:**: :************** **
```

Figure 5

```
Os11g47460.1    ---------------------------------MVTVREE--------------MRKGP   12
Os12g37970.1    ---------------------------------MVTVREE--------------IRKGP   12
AtMYB48         ---------------------------------MMQEEG---------------NRKGP   11
AtMYB59         ---------------------------------MKLVQEE--------------YRKGP   12
TaMYB13-1       ---MKTKQASKAKAAPS----------------PGKEE-----EAVAPGG---FRKGP   31
Os01g74410.1    MVVAGRKQGRHSFSASSSSSSSSSCSVVQLGHHQRPQGEDPLIGIKAAAAGGGGIMRKGP  60
                                                  *        *           *  ***

Os11g47460.1    WTEQEDLQLVCTVRLFGDRRWDFVAKVSGLNRTGKSCRLRWVNYLHPGLKHGRMSPKEEH   72
Os12g37970.1    WTEQEDLQLVCTVRLFGERRWDFIAKVSGLNRTGKSCRLRWVNYLHPGLKRGRMSPHEER   72
AtMYB48         WTEQEDILLVNFVHLFGDRRWDFIAKVSGLNRTGKSCRLRWVNYLHPGLKRGKMTPQEER   71
AtMYB59         WTEQEDILLVNFVHLFGDRRWDFVAKVSGLNRTGKSCRLRWVNYLHPGLKRGKMTPQEER   72
TaMYB13-1       WTEQEDMKLAWFVRLFGERRWDFLAKVSGLNRTGKSCRLRWVNYLHPDLKRGRMSPEEER   91
Os01g74410.1    WTEQEDVQLVWFVRLLGERR-DFLAKVSGLQRSGKSCRLRWVNYLHPGLKRGRMSPEEER  119
                ******  *  * * *  **  ** ***** :***********:***:***:*:*:*:

Os11g47460.1    LIIELHAR-GNRWSRIARRLPGRTDNEIKNYWRTHMRKKAQERRG---DMSPSSSSSSLV  128
Os12g37970.1    LILELHAR-GNRWSRIARRLPGRTDNEIKNYWRTHMRKKAQERKS---NMSPSSSSSSLT  128
AtMYB48         LVLELHAK-WNRWSKIARKLPGRTDNEIKNYWRTHMRKKAQEKKR---PVSPTSSFSNCS  127
AtMYB59         LVLELHAK-GNRWSKIARKLPGRTDNEIKNYWRTHMRKKAQEKKR---PMSPTSSSSNCC  128
TaMYB13-1       LVVDLHARWGNRWSRIAKAMPGRTDNEIKNYWRTHTRKLHKDTRASAASASTTTSTSMSA  151
Os01g74410.1    MVVQLHAKLGNRWSRIAKSIPGRTDNEIKNYWRTHLRKLKLQQKQ---QQSDDHHNDNDD  176
                : :: ***  **** :**  ****************** *:*                       :

Os11g47460.1    YQSCLLDT--------VPIISMDGGDIHDDRSCMARVLKSQSVMDGYTMDQIWKEIEAPG  180
Os12g37970.1    YQSCHPETP-------SMIIGIEEQELHGGSGCITSIMKTPVDMDGYPMDQIWMEIEAPN  181
AtMYB48         SSSVTTTTTNTQDTSCHSRKSSGEVSFYDTGGSSTREMN-QENEDVYSLDDIWREIDHSA  186
AtMYB59         SSSMTTTTS-------------------QDTGGS-NGKRMN-QECEDGYYSMDDWREIDQSG  168
TaMYB13-1       ASPATTSSSS------SSTIDNDNNSHHGHRDQETAASQEQADNQLLYTAGIGMDS-HLL  204
Os01g74410.1    DDDRNSSSSS------SSSNSNSNLQQQPQPEDESSASG--SLQAQHHEDQHQLFL-HPL  227
                    :

Os11g47460.1    APSLLGIDE-GKDKACSNLPCPLLTSTMSDYSCPEVFWKIDNEETPMLATQSGYGK----  235
Os12g37970.1    VLPGPCFDE-AKDSASNSLSGPLLPYPMWDYYCPETCLRMDDEIK--VAPQFGYGKGVGP  238
AtMYB48         VNIIKPVKD-IYSEQSHCLSYPNLASPSWES-SLDSIWNMDADKSK-ISSYFANDQF-FC  242
AtMYB59         ANVIKPVKDNYYSEQSCYLNFPPLASPTWES-SLESIWNMDADESK-MSS-FAIDQFPLS  225
TaMYB13-1       WN-DAIMDSYAWGAAVPSMIVPPPSSPVWDYCCSDSLWGIGDDEVEYKRMLAVAGAS---  260
Os01g74410.1    WNDDIIVDVDCWSSTN--VVAPPPMP-------ASPLWDIDDAFFCSDYSLPLWG-----  273
                                 ..    ,         :  *                       :.

Os11g47460.1    ----------
Os12g37970.1    CY--------  240
AtMYB48         FQHSRSPWSSG  253
AtMYB59         FEHGSGRL---  233
TaMYB13-1       ----------
Os01g74410.1    ----------
```

Overall amino acid sequence identities between TaMYB13-1 and its closest homologues in Arabidopsis and rice

| MYB Gene | Plant species | % amino acid identity with TaMYB13-1 |
|---|---|---|
| AtMYB48 (AT3G46130.1) | Arabidopsis thaliana | 40.7 |
| AtMYB59 (AT5G59780.3) | Arabidopsis thaliana | 42.6 |
| LOC_Os01g74410.1 | Oryza sativa subsp. japonica | 45.2 |
| LOC_Os11g47460.1 | Oryza sativa subsp. japonica | 42.8 |
| LOC_Os12g37970.1 | Oryza sativa subsp. japonica | 43.0 |

Figure 6

TaMYB13-selected oligonucleotides

```
SO1              TTACGAGGAAGTTAGGTTCGACCTAACGCA
SO2            TCGACCGAATAAAGTTTGGTATGATGTGCT
SO3                    CGAGTTAGGTAACTTTACCTTACGGGCGTA
SO4      TAGGTGTACCTAACAATAAGTTAGGTAGCT
SO5            GATGTTGCTATTTTTTGGTTTGTACCTGTC
SO6      TGTAGGATGGACCGAACAAATTAGGTCATA
SO7      TCAGATGCGACCTAATAAAGTTAGGTAGGG
SO8         ACACCTGACCTAGAATATTAGGTTGGACGA
SO9          CCTACCCAACTTATTGTTAGGTACACCTAG
SO10     GGAAATGAAACCTAACAAAGTTAGGTAAGA
SO11         ACCATACCTAACAAATTAGGTACGTCGGGC
SO12                    CCGTTAGGTCCTGGCTTCCACTAACGTCTA
SO13                    GGGGTTAGGTACGCCCCACCCACCTACCCG
SO14     ACACCTACACCTACTTTAATTAGGTATCGA
SO15     TCGGTGTACCTAACAATAAGTTAGGTAGA
SO16     CTGATCATACCAAACTTTATTCGGTAGAGC
SO17         TATCCAACTTATTTTTAGGTACATTTAGGA
```

TaMYB13 binding sequence profile 

Figure 9

(a) DTTHGGT sites from fructosyltransferase promoters and TaMYB13 binding activity

| Name | Start position & (strand) | Sequence | Relative binding activity |
|---|---|---|---|
| SynO2 | | TCGACCGAATAAAGTTTGGTATGATGT | 1.00 ± 0.06 |
| Hv6-SFT-s1 | -971(+) | CAAAGTTTCACTATATGTTAGGTACTTGTT | 1.21 ± 0.10 |
| Hv6-SFT-s2 | -728(-) | AAGCTTCAAAGCCATTTGGTAACTAGC | 0.03 ± 0.01 |
| Hv6-SFT-s3 | -15 (-) | TCAACTCCGAGAGGGTTTGGTAGATTCT | 0.09 ± 0.02 |
| Ta6-SFT1s1 | -639(-) | GGTCAAGACTGTGTTAGGTTCGGTTGTAATT | 0.63 ± 0.05 |
| Ta6-SFT1s2 | -436(-) | CGGTCAAGACTGTGTTAGGTTCGGCTG | 0.45 ± 0.02 |
| Ta6-SFT1s3 | -16 (-) | GAACTCCAAGAGAGTTTGGTAGATTGT | 0.26 ± 0.02 |
| Ta6-SFT2s1 | -817(-) | TGGCCAAGACTGTGTTAGGTTTGGCTG | 0.59 ± 0.03 |
| Ta6-SFT2s2 | -615(-) | CGGCCAAGACTGTGTTAGGTTTGGCTG | 0.57 ± 0.07 |
| Ta6-SFT2s3 | -413(-) | CGGCCAAGACTGTGTTAGGTTCTGCTG | 0.53 ± 0.08 |
| Ta6-SFT2s4 | -16 (-) | GAACTCCAAGAGAGTTTGGTAGATTGT | 0.26 ± 0.02 |
| Ta1-SST-s1 | -1786(-) | CCATCGGGTTTGCATTAGGTTCATAAG | 0.19 ± 0.03 |
| Ta1-SST-s2 | -1449(-) | GGGACGCATGCATGTTCGGTAAGAAACAA | 0.53 ± 0.02 |

(b) Illustration of the binding activity of TaMYB13CELD to Hv6-SFT-s1 and Ta1-SST-s2 sites

Hv6-SFT-s1   Ta1-SST-s2   Control

Figure 11

SEQUENCE LISTING

<160> NUMBER OF SEQ ID NOS: 168

<210> SEQ ID NO 1
<211> LENGTH: 260
<212> TYPE: PRT
<213> ORGANISM: Triticum aestivum

<400> SEQUENCE: 1

```
Met Lys Thr Lys Gln Ala Ser Lys Ala Lys Ala Ala Pro Ser Pro Gly
1               5                   10                  15

Lys Glu Glu Glu Ala Val Ala Pro Gly Gly Phe Arg Lys Gly Pro Trp
            20                  25                  30

Thr Glu Gln Glu Asp Met Lys Leu Ala Trp Phe Val Arg Leu Phe Gly
        35                  40                  45

Glu Arg Arg Trp Asp Phe Leu Ala Lys Val Ser Gly Leu Asn Arg Thr
50                  55                  60

Gly Lys Ser Cys Arg Leu Arg Trp Val Asn Tyr Leu His Pro Asp Leu
65                  70                  75                  80

Lys Arg Gly Arg Met Ser Pro Glu Glu Arg Leu Val Val Asp Leu
            85                  90                  95

His Ala Arg Trp Gly Asn Arg Trp Ser Arg Ile Ala Lys Ala Met Pro
            100                 105                 110

Gly Arg Thr Asp Asn Glu Ile Lys Asn Tyr Trp Arg Thr His Thr Arg
        115                 120                 125

Lys Leu His Lys Asp Thr Arg Ala Ser Ala Ala Ser Ala Ser Thr Thr
    130                 135                 140

Thr Ser Thr Ser Met Ser Ala Ala Ser Pro Ala Thr Thr Ser Ser Ser
145                 150                 155                 160

Ser Ser Ser Thr Ile Asp Asn Asp Asn Asn Ser His His Gly His Arg
                165                 170                 175

Asp Gln Glu Thr Ala Ala Ser Gln Glu Gln Ala Asp Asn Gln Leu Leu
            180                 185                 190

Tyr Thr Ala Gly Ile Gly Met Asp Ser His Leu Leu Trp Asn Asp Ala
        195                 200                 205

Ile Met Asp Ser Tyr Ala Trp Gly Ala Ala Val Pro Ser Met Ile Val
```

```
            210                 215                 220
Pro Pro Ser Ser Pro Val Trp Asp Tyr Cys Cys Ser Asp Ser Leu
225                 230                 235                 240

Trp Gly Ile Gly Asp Asp Glu Val Glu Tyr Lys Lys Met Leu Ala Val
            245                 250                 255

Ala Gly Ala Ser
            260

<210> SEQ ID NO 2
<211> LENGTH: 264
<212> TYPE: PRT
<213> ORGANISM: Triticum aestivum

<400> SEQUENCE: 2

Met Lys Thr Lys Gln Ala Ser Lys Ala Lys Ala Pro Ser Pro Gly
1               5                   10                  15

Lys Glu Glu Glu Ala Val Ala Pro Gly Gly Phe Arg Lys Gly Pro Trp
                20                  25                  30

Thr Glu Gln Glu Asp Met Lys Leu Ala Trp Phe Val Arg Leu Phe Gly
            35                  40                  45

Glu Arg Arg Trp Asp Phe Leu Ala Lys Val Ser Gly Leu Asn Arg Thr
50                  55                  60

Gly Lys Ser Cys Arg Leu Arg Trp Val Asn Tyr Leu His Pro Asp Leu
65                  70                  75                  80

Lys Arg Gly Arg Met Ser Pro Glu Glu Glu Arg Leu Val Val Asp Leu
                85                  90                  95

His Ala Arg Trp Gly Asn Arg Trp Ser Arg Ile Ala Lys Ala Met Pro
            100                 105                 110

Gly Arg Thr Asp Asn Glu Ile Lys Asn Tyr Trp Arg Thr His Thr Arg
        115                 120                 125

Lys Leu His Lys Asp Thr Arg Ala Ala Ser Ala Ala Ser Ala Ser Thr
130                 135                 140

Thr Thr Thr Thr Ser Thr Ser Met Ser Ala Ala Ser Pro Ala Thr Thr
145                 150                 155                 160

Ser Ser Ser Ser Ser Ser Thr Asn Asp Asn Asp Asn His Ser His
                165                 170                 175

His Gly His Gly Asp Gln Glu Thr Ala Ala Ser Gln Glu Gln Ala Asp
            180                 185                 190

His Gln Leu Leu Tyr Thr Ser Gly Ile Gly Met Asp Ser His Leu Leu
        195                 200                 205

Trp Asn Asp Ala Leu Met Asp Ser Tyr Ala Trp Gly Ala Ala Ala Pro
210                 215                 220

Ser Met Ile Val Pro Pro Pro Ser Ser Pro Val Trp Asp Tyr Cys Cys
225                 230                 235                 240

Ser Asp Ser Leu Trp Gly Ile Gly Asp Asp Glu Val Glu Tyr Lys Lys
                245                 250                 255

Met Leu Ala Val Ala Gly Ala Ser
            260

<210> SEQ ID NO 3
<211> LENGTH: 265
<212> TYPE: PRT
<213> ORGANISM: Triticum aestivum

<400> SEQUENCE: 3

Met Lys Met Lys Gln Thr Lys Lys Thr Ser Ala Pro Ser Pro Gly Lys
```

```
              1               5                  10                 15
            Gln Glu Glu Ala Val Ala Pro Gly Gly Phe Arg Lys Gly Pro Trp Thr
                           20                 25                 30

Glu Gln Glu Asp Met Lys Leu Ala Trp Phe Val Arg Leu Phe Gly Glu
                           35                 40                 45

Arg Arg Trp Asp Phe Leu Ala Lys Val Ser Gly Leu Asn Arg Thr Gly
             50                 55                 60

Lys Ser Cys Arg Leu Arg Trp Val Asn Tyr Leu His Pro Asp Leu Lys
             65                 70                 75                 80

Arg Gly Arg Met Ser Pro Asp Glu Glu Arg Leu Val Val Asp Leu His
                           85                 90                 95

Ala Arg Trp Gly Asn Arg Trp Ser Arg Ile Ala Lys Ala Met Pro Gly
                           100                105                110

Arg Thr Asp Asn Glu Ile Lys Asn Tyr Trp Arg Thr His Thr Arg Lys
                           115                120                125

Leu His Lys Asp Ala Arg Ala Ala Ala Asp Gly Ala Ser Ala Ala
                           130                135                140

Ser Ala Ser Thr Thr Thr Ser Thr Ser Met Ser Ala Ala Ser Pro Ala
            145                150                155                160

Thr Thr Ser Ser Ser Ser Ser Thr Asn Asp Asn His Asn His Leu
                           165                170                175

His His Gly His Gly Asp Gln Glu Thr Ala Ala Ser Gln Glu Gln Ala
                           180                185                190

Asp Asn Gln Leu Leu Tyr Thr Ala Gly Ile Gly Met Asp Ser His Leu
                           195                200                205

Leu Trp Asn Asp Ala Ile Met Asp Ser Tyr Ala Trp Gly Ala Ala Ala
                           210                215                220

Pro Ser Met Leu Val Pro Pro Ser Pro Val Trp Asp Tyr Cys
            225                230                235                240

Cys Ser Asp Ser Leu Trp Gly Ile Gly Asp Asp Glu Val Glu Tyr Lys
                           245                250                255

Lys Met Leu Ala Val Ala Gly Ala Ser
                           260                265

<210> SEQ ID NO 4
<211> LENGTH: 279
<212> TYPE: PRT
<213> ORGANISM: Hordeum vulgare

<400> SEQUENCE: 4

Met Lys Met Lys Gln Ala Ser Lys Ala Lys Ala Thr Ala Thr Ser Pro
 1               5                  10                 15

Gly Lys Glu Asp Glu Ala Val Ala Pro Gly Gly Phe Arg Lys Gly Pro
                20                 25                 30

Trp Thr Glu Gln Glu Asp Met Lys Leu Ala Trp Phe Val Arg Leu Phe
             35                 40                 45

Gly Glu Arg Arg Trp Asp Phe Leu Ala Lys Val Ser Gly Leu Asn Arg
 50                 55                 60

Thr Gly Lys Ser Cys Arg Leu Arg Trp Val Asn Tyr Leu His Pro Asp
 65                 70                 75                 80

Leu Lys Arg Gly Arg Met Thr Pro Asp Glu Glu Arg Leu Val Val Asp
                85                 90                 95

Leu His Ala Arg Trp Gly Asn Arg Trp Ser Arg Ile Ala Lys Ala Met
             100                105                110
```

Pro Gly Arg Thr Asp Asn Glu Ile Lys Asn Tyr Trp Arg Thr His Thr
            115                 120                 125

Arg Lys Leu His Lys Asp Thr Arg Ala Val Ala Ala Ala Asp Gly Ser
        130                 135                 140

Gly Ser Ala Ala Ser Ala Ser Thr Thr Thr Thr Ser Thr Ser Met Ser
145                 150                 155                 160

Pro Ala Ser Pro Ala Thr Thr Ser Ser Ser Ser Ser Thr Thr Asp
                165                 170                 175

Asn Asp Asn His Ser His His His Gly His Gly His His Asp Gln Glu
            180                 185                 190

Thr Ala Ala Ser Cys Gln Glu Gln Gln Ala Ala Glu Gln Gln Leu
        195                 200                 205

Phe Tyr Thr Ser Val Gly Ala Met Asp Ser His Leu Leu Trp Asn Asp
        210                 215                 220

Asp Ala Met Leu Asp Ser Tyr Ala Trp Gly Ala Thr Ala Leu Pro Ser
225                 230                 235                 240

Met Ile Val Pro Pro Ser Ser Pro Val Trp Asp Tyr Cys Cys Ser
                245                 250                 255

Asp Ser Leu Trp Gly Ile Gly Asp Asp Glu Val Glu Tyr Lys Lys Met
            260                 265                 270

Leu Ala Val Ala Gly Ala Ser
        275

<210> SEQ ID NO 5
<211> LENGTH: 783
<212> TYPE: DNA
<213> ORGANISM: Triticum aestivum

<400> SEQUENCE: 5

```
atgaagacga agcaggcttc caaggccaag gcggcgccgt cgccggggaa ggaggaggaa      60
gcagttgcac cgggtggttt ccgcaagggg ccatggacgg agcaggagga catgaagctg     120
gcgtggttcg tgcggctctt cggcgagcgc cgctgggatt tcttagctaa ggtgtcaggt     180
cttaaccgga cggggaagag ctgccggctc cggtgggtca actacctgca cccggacctc     240
aagcgcggcc ggatgagccc cgaagaggag cgcctcgtcg tcgacctcca cgcccgctgg     300
ggcaaccgct ggtcacgcat cgccaaggcc atgccggggc gcaccgacaa cgagatcaag     360
aactactggc gcacccacac ccgcaagctc acaaggaca cgcgcgcctc tgctgcttcg     420
gcctctacga ccacgtccac gtccatgtcg gcggcgtctc cggccaccac gtccagctcc     480
tcctcttcaa cgatcgacaa cgacaacaac tcacatcacg gccaccgcga ccaagagacg     540
gcggccagcc aggaacaagc ggataaccag ctgctctaca ccgccggcat cggcatggac     600
agccacctcc tttggaacga cgccatcatg gactcctacg catggggagc cgccgtgccg     660
tcgatgatag tgccgccgcc ttcatcgccg gtgtgggact actgctgctc ggattcgctc     720 tggggatag cgacgacga ggtcgagtac aagaagatgc tcgccgtcgc cggtgcctca     780
tga                                                                    783
```

<210> SEQ ID NO 6
<211> LENGTH: 795
<212> TYPE: DNA
<213> ORGANISM: Triticum aestivum

<400> SEQUENCE: 6

```
atgaagacga agcaggcttc caaggccaag gcggcgccgt cgccggggaa ggaggaggaa      60
```

| | | |
|---|---|---|
| gcagttgcac cggggggttt ccggaaggga ccatggacgg agcaggagga catgaagctg | 120 | |
| gcgtggttcg tgcggctctt cggcgagcgc cgctgggatt tcttagctaa ggtgtcaggt | 180 | |
| ctcaaccgga cggggaagag ctgccggctc cggtgggtca actacctgca cccggacctc | 240 | |
| aagcgcggcc ggatgagccc cgaagaggag cgcctcgtcg tcgacctcca cgcccgctgg | 300 | |
| ggcaaccgct ggtcccgcat cgccaaggcc atgccgggcc gcaccgacaa cgagatcaag | 360 | |
| aactactggc gcacccacac ccgcaagctc acaaggaca cgcgcgccgc ctctgctgct | 420 | |
| tcggcctcca cgaccacgac cacgtccacg tccatgtcgg cggcgtctcc ggccaccacg | 480 | |
| tccagctcct cctcctcctc aacgaacgac aacgataacc actcgcatca cggccacggc | 540 | |
| gaccaagaga cggcggccag ccaggaacaa gcagatcacc agctgctcta cacctccggc | 600 | |
| atcggcatgg acagccacct cctttggaac gacgccctca tggactccta cgcatgggga | 660 | |
| gcggccgcgc cgtctatgat agtgccgccg ccttcatcgc cggtgtggga ctactgctgc | 720 | |
| tcggattcgc tctggggaat aggtgacgac gaggtcgagt acaagaagat gctcgccgtc | 780 | |
| gccggtgcct catga | 795 | |

<210> SEQ ID NO 7
<211> LENGTH: 798
<212> TYPE: DNA
<213> ORGANISM: Triticum aestivum

<400> SEQUENCE: 7

| | | |
|---|---|---|
| atgaagatga agcagacgaa gaagacgtcg gcgccgtcgc cgggcaagca ggaggaagca | 60 | |
| gttgcacccg ggggtttccg gaaggggcca tggacggagc aggaggacat gaagctggcg | 120 | |
| tggttcgtgc ggctcttcgg cgagcgccgc tgggattct tagctaaggt gtcaggtctc | 180 | |
| aaccggacgg ggaagagctg ccggctccgg tgggtcaact acctgcaccc ggacctgaag | 240 | |
| cgcggccgga tgagccccga cgaggagcgc ctcgtcgtcg acctccacgc ccgctggggc | 300 | |
| aaccgctggt cccgcatcgc caaggccatg ccggggcgca ccgacaacga gatcaagaac | 360 | |
| tactggcgca cccacacccg caagctccac aaggacgcgc gcgccgccgc gcggacggc | 420 | |
| gcctctgctg cttctgcctc cacgaccacg tccacgtcca tgtcggcggc gtctccggcc | 480 | |
| accacgtcca gctcctcctc ctcaacaaac gacaaccaca ccacttgca tcacggccac | 540 | |
| ggcgaccaag agacggcggc cagccaggaa caagcggata accagctgct ctacaccgcc | 600 | |
| ggcatcggca tggacagcca cctccttggg aacgacgcca tcatggactc ttacgcatgg | 660 | |
| ggagcggccg cgccgtccat gttagtgccg ccgccttcat cgccggtgtg ggactactgc | 720 | |
| tgctcggatt cgctctgggg gataggcgac gacgaggtcg agtacaagaa gatgctcgcc | 780 | |
| gtcgccggtg cctcatga | 798 | |

<210> SEQ ID NO 8
<211> LENGTH: 840
<212> TYPE: DNA
<213> ORGANISM: Hordeum vulgare

<400> SEQUENCE: 8

| | | |
|---|---|---|
| atgaagatga agcaggcttc caaggcgaag gcgacggcga cgtcgccggg gaaggaggat | 60 | |
| gaagcggttg cgccgggcgg tttccgcaag gggccatgga cggagcagga ggacatgaag | 120 | |
| ctggcgtggt tcgtgcggct cttcggcgag cgccgctggg atttcttggc taaggtgtca | 180 | |
| ggtctcaacc ggaccgggaa gagctgccgc ctccggtggg tcaactacct ccaccccgac | 240 | |
| ctgaagcgcg gccggatgac gcccgacgag gagcgcctcg tcgtcgacct ccacgcccgc | 300 | |

```
tggggcaacc gatggtcacg catcgccaag gccatgccgg gccgcaccga caacgagatc    360
aagaactact ggcgcacaca tacccgcaag ctccacaagg acactcgcgc cgtcgccgcc    420
gccgacggct ccggctccgc tgcttcagcc tccacgacga ccacgtccac gtccatgtcg    480
ccggcgtctc cggccacaac ctccagctcc tcctcttcaa cgaccgacaa cgacaaccac    540
tcacatcatc acggccacgg ccaccacgac caagagaccg cggccagctg ccaggaacaa    600
caacaggcgg cggaacagca gctcttctac accagcgtcg cgccatgga cagccacctg    660 ctctggaacg acgatgccat gctcgattcc tacgcctggg agccaccgc cttgccgtcc     720 atgatcgtcc cgccgccttc atcgccggtg tgggactact gctgctcgga ttcgctctgg    780
gggataggcg acgacgaggt cgagtacaag aagatgctcg ccgtcgccgg tgcctcatga    840
```

<210> SEQ ID NO 9
<211> LENGTH: 938
<212> TYPE: DNA
<213> ORGANISM: Triticum aestivum

<400> SEQUENCE: 9

```
atgaagacga agcaggcttc caaggccaag gcggcgccgt cgccggggaa ggaggaggaa     60
gcagttgcac cgggtggttt ccgcaagggg ccatggacgg agcaggagga catgaagctg    120
gcgtggttcg tgcggctctt cggcgagcgc cgctgggatt tcttagctaa ggtgtcaggt    180
ttgcaaggtg gcgggtgacc catgccgtgc catgcatgcg ccatgcatgc atgcatgtct    240
gggaccaaaa tatgatgtag ccatggtcct ttgtgtgcta acgctctcgg tctccgccgg    300 caccatcttgc tcttgtgttt gtcttggcga caggtcttaa ccggacgggg aagagctgcc    360
ggctccggtg ggtcaactac ctgcacccgg acctcaagcg cggccggatg agccccgaag    420
aggagcgcct cgtcgtcgac ctccacgccc gctggggcaa ccgctggtca cgcatcgcca    480
aggccatgcc ggggcgcacc gacaacgaga tcaagaacta ctggcgcacc cacacccgca    540
agctccacaa ggacacgcgc gcctctgctg cttcggcctc tacgaccacg tccacgtcca    600
tgtcggcggc gtctccggcc accagtcca gctcctcctc ttcaacgatc gacaacgaca    660
acaactcaca tcacggccac cgcgaccaag agacggcggc cagccaggaa caagcggata    720
accagctgct ctacaccgcc ggcatcggca tggacagcca cctcctttgg aacgacgcca    780
tcatggactc ctacgcatgg ggagccgccg tgccgtcgat gatagtgccg ccgccttcat    840
cgccggtgtg ggactactgc tgctcggatt cgctctgggg gataggcgac gacgaggtcg    900
agtacaagaa gatgctcgcc gtcgccggtg cctcatga                            938
```

<210> SEQ ID NO 10
<211> LENGTH: 975
<212> TYPE: DNA
<213> ORGANISM: Triticum aestivum

<400> SEQUENCE: 10

```
atgaagacga agcaggcttc caaggccaag gcggcgccgt cgccggggaa ggaggaggaa     60
gcagttgcac cggggggttt ccggaaggga ccatggacgg agcaggagga catgaagctg    120
gcgtggttcg tgcggctctt cggcgagcgc cgctgggatt tcttagctaa ggtgtcaggt    180
ttgcaaggtg gcgggtgacc catgccgtgc catgcgatgc catgcgtgcg cctccacgca    240
tgcatgcatg caggcatgca tgggaccaaa tatgatgtca gccatggtcc tttgtgtgct    300
aacgctctcg ctctccgccg tccggcacct cccgctcttg tgtctgcctt gcctacaggt    360
```

| | |
|---|---|
| ctcaaccgga cggggaagag ctgccggctc cggtgggtca actacctgca cccggacctc | 420 |
| aagcgcggcc ggatgagccc cgaagaggag cgcctcgtcg tcgacctcca cgcccgctgg | 480 |
| ggcaaccgct ggtcccgcat cgccaaggcc atgccgggcc gcaccgacaa cgagatcaag | 540 |
| aactactggc gcacccacac ccgcaagctc acaaggaca cgcgcgccgc ctctgctgct | 600 |
| tcggcctcca cgaccacgac cacgtccacg tccatgtcgg cggcgtctcc ggccaccacg | 660 |
| tccagctcct cctcctcctc aacgaacgac aacgataacc actcgcatca cggccacggc | 720 |
| gaccaagaga cggcggccag ccaggaacaa gcagatcacc agctgctcta cacctccggc | 780 |
| atcggcatgg acagccacct cctttggaac gacgccctca tggactccta cgcatgggga | 840 |
| gcggccgcgc cgtctatgat agtgccgccg ccttcatcgc cggtgtggga ctactgctgc | 900 |
| tcggattcgc tctggggaat aggtgacgac gaggtcgagt acaagaagat gctcgccgtc | 960 |
| gccggtgcct catga | 975 |

<210> SEQ ID NO 11
<211> LENGTH: 957
<212> TYPE: DNA
<213> ORGANISM: Triticum aestivum

<400> SEQUENCE: 11

| | |
|---|---|
| atgaagatga agatgaagca gacgaagaag acgtcggcgc cgtcgccggg caagcaggag | 60 |
| gaagcagttg cacccggggg tttccggaag gggccatgga cggagcagga ggacatgaag | 120 |
| ctggcgtggt tcgtgcggct cttcggcgag cgccgctggg atttcttagc taaggtgtca | 180 |
| ggtttgcaag gtggcgggtg acccatgccg tgccatgcat gcgcatgcat gcatgcatgt | 240 |
| ctgggaccaa ataacatgta gccatggtcc tttgtgtgct aacgctctcg gtctccgccg | 300 |
| gcacctcttg ctcttgtgtc tgccttggct acaggtctca accggacggg gaagagctgc | 360 |
| cggctccggt gggtcaacta cctgcacccg gacctgaagc gcggccggat gagccccgac | 420 |
| gaggagcgcc tcgtcgtcga cctccacgcc gctggggca accgctggtc ccgcatcgcc | 480 |
| aaggccatgc cggggcgcac cgacaacgag atcaagaact actggcgcac ccacacccgc | 540 |
| aagctccaca ggacgcgcg cgccgccgcc gcggacggcg cctctgctgc ttctgcctcc | 600 |
| acgaccacgt ccacgtccat gtcggcggcg tctccggcca ccgtccag ctcctcctcc | 660 |
| tcaacaaacg acaaccacaa ccacttgcat cacggccacg cgaccaaga cgcggcc | 720 |
| agccaggaac aagcggataa ccagctgctc tacaccgccg gcatcggcat ggacagccac | 780 |
| ctcctttgga cgacgccat catggactct tacgcatggg gagcggccgc gccgtccatg | 840 |
| ttagtgccgc cgccttcatc gccggtgtgg gactactgct gctcggattc gctctggggg | 900 |
| ataggcgacg acgaggtcga gtacaagaag atgctcgccg tcgccggtgc ctcatga | 957 |

<210> SEQ ID NO 12
<211> LENGTH: 999
<212> TYPE: DNA
<213> ORGANISM: Hordeum vulgare

<400> SEQUENCE: 12

| | |
|---|---|
| atgaagatga agcaggcttc caaggcgaag gcgacggcga cgtcgccggg gaaggaggat | 60 |
| gaagcggttg cgccgggcgg tttccgcaag gggccatgga cggagcagga ggacatgaag | 120 |
| ctggcgtggt tcgtgcggct cttcggcgag cgccgctggg atttcttggc taaggtgtca | 180 |
| ggtttgcaag gtggcgggtg acccatgtcg tgccatgcat gcatgcgcga tgcatgctgg | 240 |
| catgcatggg accaaaatat gatgtagcca tggccttttg tgtgctaacg ctctcgccct | 300 |

```
ccaccggcac ctcttgctct tgtctctgcc ttgcctacag gtctcaaccg gaccgggaag    360
agctgccgcc tccggtgggt caactacctc accccgacc tgaagcgcgg ccggatgacg     420
cccgacgagg agcgcctcgt cgtcgacctc acgcccgct ggggcaaccg atggtcacgc     480
atcgccaagg ccatgccggg ccgcaccgac aacgagatca agaactactg gcgcacacat    540
acccgcaagc tccacaagga cactcgcgcc gtcgccgccg ccgacggctc cggctccgct    600
gcttcagcct ccacgacgac cacgtccacg tccatgtcgc cggcgtctcc ggccacaacc    660
tccagctcct cctcttcaac gaccgacaac gacaaccact cacatcatca cggccacggc    720
caccacgacc aagagaccgc ggccagctgc caggaacaac aacaggcggc ggaacagcag    780
ctcttctaca ccagcgtcgg cgccatggac agccacctgc tctggaacga cgatgccatg    840
ctcgattcct acgcctgggg agccaccgcc ttgccgtcca tgatcgtccc gccgccttca    900
tcgccggtgt gggactactg ctgctcggat tcgctctggg ggataggcga cgacgaggtc    960
gagtacaaga agatgctcgc cgtcgccggt gcctcatga                            999
```

<210> SEQ ID NO 13
<211> LENGTH: 237
<212> TYPE: PRT
<213> ORGANISM: Oryza sativa

<400> SEQUENCE: 13

```
Met Val Thr Val Arg Glu Glu Met Arg Lys Gly Pro Trp Thr Glu Gln
1               5                   10                  15

Glu Asp Leu Gln Leu Val Cys Thr Val Arg Leu Phe Gly Asp Arg Arg
            20                  25                  30

Trp Asp Phe Val Ala Lys Val Ser Gly Leu Asn Arg Thr Gly Lys Ser
        35                  40                  45

Cys Arg Leu Arg Trp Val Asn Tyr Leu His Pro Gly Leu Lys His Gly
    50                  55                  60

Arg Met Ser Pro Lys Glu Glu His Leu Ile Ile Glu Leu His Ala Arg
65                  70                  75                  80

Trp Gly Asn Arg Trp Ser Arg Ile Ala Arg Arg Leu Pro Gly Arg Thr
                85                  90                  95

Asp Asn Glu Ile Lys Asn Tyr Trp Arg Thr His Met Arg Lys Lys Ala
            100                 105                 110

Gln Glu Arg Arg Gly Asp Met Ser Pro Ser Ser Ser Ser Ser Ser Leu
        115                 120                 125

Val Tyr Gln Ser Cys Leu Leu Asp Thr Val Pro Ile Ile Ser Met Asp
    130                 135                 140

Gly Gly Asp Ile His Asp Asp Arg Ser Cys Met Ala Arg Val Leu Lys
145                 150                 155                 160

Ser Thr Gln Ser Val Met Asp Gly Tyr Thr Met Asp Gln Ile Trp Lys
                165                 170                 175

Glu Ile Glu Ala Pro Gly Ala Pro Ser Leu Leu Gly Ile Asp Glu Gly
            180                 185                 190

Lys Asp Lys Ala Cys Ser Asn Leu Pro Cys Pro Leu Leu Thr Ser Thr
        195                 200                 205

Met Ser Asp Tyr Ser Cys Pro Glu Val Phe Trp Lys Ile Asp Asn Glu
    210                 215                 220

Glu Thr Arg Met Leu Ala Thr Gln Ser Gly Tyr Gly Lys
225                 230                 235
```

```
<210> SEQ ID NO 14
<211> LENGTH: 242
<212> TYPE: PRT
<213> ORGANISM: Oryza sativa

<400> SEQUENCE: 14
```

Met Val Thr Val Arg Glu Glu Ile Arg Lys Gly Pro Trp Thr Glu Gln
1               5                   10                  15

Glu Asp Leu Gln Leu Val Cys Thr Val Arg Leu Phe Gly Glu Arg Arg
            20                  25                  30

Trp Asp Phe Ile Ala Lys Val Ser Gly Leu Asn Arg Thr Gly Lys Ser
        35                  40                  45

Cys Arg Leu Arg Trp Val Asn Tyr Leu His Pro Gly Leu Lys Arg Gly
    50                  55                  60

Arg Met Ser Pro His Glu Arg Leu Ile Leu Glu Leu His Ala Arg
65                  70                  75                  80

Trp Gly Asn Arg Trp Ser Arg Ile Ala Arg Arg Leu Pro Gly Arg Thr
                85                  90                  95

Asp Asn Glu Ile Lys Asn Tyr Trp Arg Thr His Met Arg Lys Lys Ala
            100                 105                 110

Gln Glu Arg Lys Ser Asn Met Ser Pro Ser Ser Ser Ser Ser Ser Leu
        115                 120                 125

Thr Tyr Gln Ser Cys His Pro Glu Thr Pro Ser Met Ile Ile Gly Ile
    130                 135                 140

Glu Glu Gln Glu Leu His Gly Gly Ser Gly Cys Ile Thr Ser Ile Met
145                 150                 155                 160

Lys Ser Thr Pro Val Asp Met Asp Gly Tyr Pro Met Asp Gln Ile Trp
                165                 170                 175

Met Glu Ile Glu Ala Pro Asn Val Leu Pro Gly Pro Cys Phe Asp Glu
            180                 185                 190

Ala Lys Asp Ser Ala Ser Asn Ser Leu Ser Gly Pro Leu Leu Pro Tyr
        195                 200                 205

Pro Met Trp Asp Tyr Tyr Cys Pro Glu Thr Cys Leu Arg Met Asp Asp
    210                 215                 220

Glu Ile Lys Val Ala Pro Gln Phe Gly Tyr Gly Lys Gly Val Gly Pro
225                 230                 235                 240

Cys Tyr

```
<210> SEQ ID NO 15
<211> LENGTH: 256
<212> TYPE: PRT
<213> ORGANISM: Arabidopsis thaliana

<400> SEQUENCE: 15
```

Met Met Gln Glu Glu Gly Asn Arg Lys Gly Pro Trp Thr Glu Gln Glu
1               5                   10                  15

Asp Ile Leu Leu Val Asn Phe Val His Leu Phe Gly Asp Arg Arg Trp
            20                  25                  30

Asp Phe Ile Ala Lys Val Ser Gly Leu Asn Arg Thr Gly Lys Ser Cys
        35                  40                  45

Arg Leu Arg Trp Val Asn Tyr Leu His Pro Gly Leu Lys Arg Gly Lys
    50                  55                  60

Met Thr Pro Gln Glu Glu Arg Leu Val Leu Glu Leu His Ala Lys Trp
65                  70                  75                  80

Gly Asn Arg Trp Ser Lys Ile Ala Arg Lys Leu Pro Gly Arg Thr Asp
                85                  90                  95

```
Asn Glu Ile Lys Asn Tyr Trp Arg Thr His Met Arg Lys Lys Ala Gln
                100                 105                 110

Glu Lys Lys Arg Pro Val Ser Pro Thr Ser Ser Phe Ser Asn Cys Ser
            115                 120                 125

Ser Ser Ser Val Thr Thr Thr Thr Asn Thr Gln Asp Thr Ser Cys
130             135                 140

His Ser Arg Lys Ser Ser Gly Glu Val Ser Phe Tyr Asp Thr Gly Gly
145                 150                 155                 160

Ser Arg Ser Thr Arg Glu Met Asn Gln Glu Asn Glu Asp Val Tyr Ser
                165                 170                 175

Leu Asp Asp Ile Trp Arg Glu Ile Asp His Ser Ala Val Asn Ile Ile
                180                 185                 190

Lys Pro Val Lys Asp Ile Tyr Ser Glu Gln Ser His Cys Leu Ser Tyr
                195                 200                 205

Pro Asn Leu Ala Ser Pro Ser Trp Glu Ser Ser Leu Asp Ser Ile Trp
            210                 215                 220

Asn Met Asp Ala Asp Lys Ser Lys Ile Ser Ser Tyr Phe Ala Asn Asp
225                 230                 235                 240

Gln Phe Pro Phe Cys Phe Gln His Ser Arg Ser Pro Trp Ser Ser Gly
                245                 250                 255

<210> SEQ ID NO 16
<211> LENGTH: 235
<212> TYPE: PRT
<213> ORGANISM: Arabidopsis thaliana

<400> SEQUENCE: 16

Met Lys Leu Val Gln Glu Glu Tyr Arg Lys Gly Pro Trp Thr Glu Gln
1               5                   10                  15

Glu Asp Ile Leu Leu Val Asn Phe Val His Leu Phe Gly Asp Arg Arg
                20                  25                  30

Trp Asp Phe Val Ala Lys Val Ser Gly Leu Asn Arg Thr Gly Lys Ser
            35                  40                  45

Cys Arg Leu Arg Trp Val Asn Tyr Leu His Pro Gly Leu Lys Arg Gly
50                  55                  60

Lys Met Thr Pro Gln Glu Glu Arg Leu Val Leu Glu Leu His Ala Lys
65                  70                  75                  80

Trp Gly Asn Arg Trp Ser Lys Ile Ala Arg Lys Leu Pro Gly Arg Thr
                85                  90                  95

Asp Asn Glu Ile Lys Asn Tyr Trp Arg Thr His Met Arg Lys Lys Ala
                100                 105                 110

Gln Glu Lys Lys Arg Pro Met Ser Pro Thr Ser Ser Ser Ser Asn Cys
            115                 120                 125

Cys Ser Ser Ser Met Thr Thr Thr Thr Ser Gln Asp Thr Gly Gly Ser
130                 135                 140

Asn Gly Lys Met Asn Gln Glu Cys Glu Asp Gly Tyr Tyr Ser Met Asp
145                 150                 155                 160

Asp Ile Trp Arg Glu Ile Asp Gln Ser Gly Ala Asn Val Ile Lys Pro
                165                 170                 175

Val Lys Asp Asn Tyr Tyr Ser Glu Gln Ser Cys Tyr Leu Asn Phe Pro
                180                 185                 190

Pro Leu Ala Ser Pro Thr Trp Glu Ser Ser Leu Glu Ser Ile Trp Asn
            195                 200                 205

Met Asp Ala Asp Glu Ser Lys Met Ser Ser Phe Ala Ile Asp Gln Phe
```

```
                210                 215                 220
Pro Leu Ser Phe Glu His Gly Ser Gly Arg Leu
225                 230                 235

<210> SEQ ID NO 17
<211> LENGTH: 276
<212> TYPE: PRT
<213> ORGANISM: Oryza sativa

<400> SEQUENCE: 17

Met Val Val Ala Gly Lys Lys Gln Gly Arg His Ser Phe Ser Ala Ser
1               5                   10                  15

Ser Ser Ser Ser Ser Ser Ser Cys Ser Val Val Gln Leu Gly His
            20                  25                  30

His Gln Arg Pro Gln Gly Glu Asp Pro Leu Ile Gly Ile Lys Ala Ala
            35                  40                  45

Ala Ala Gly Gly Gly Gly Ile Met Arg Lys Gly Pro Trp Thr Glu Gln
    50                  55                  60

Glu Asp Val Gln Leu Val Trp Phe Val Arg Leu Leu Gly Glu Arg Arg
65                  70                  75                  80

Trp Asp Phe Leu Ala Lys Val Ser Gly Leu Gln Arg Ser Gly Lys Ser
                85                  90                  95

Cys Arg Leu Arg Trp Val Asn Tyr Leu His Pro Gly Leu Lys Arg Gly
            100                 105                 110

Arg Met Ser Pro Glu Glu Glu Arg Met Val Val Gln Leu His Ala Lys
            115                 120                 125

Leu Gly Asn Arg Trp Ser Arg Ile Ala Lys Ser Ile Pro Gly Arg Thr
130                 135                 140

Asp Asn Glu Ile Lys Asn Tyr Trp Arg Thr His Leu Arg Lys Leu Lys
145                 150                 155                 160

Leu Lys Gln Gln Lys Gln Gln Ser Asp His His Asn Asp Asn
                165                 170                 175

Asp Asp Asp Asp Asp Arg Asn Ser Ser Ser Ser Ser Ser Ser Asn
            180                 185                 190

Ser Asn Ser Asn Leu Gln Gln Gln Pro Gln Pro Glu Asp Glu Ser Ser
        195                 200                 205

Ala Ser Gly Ser Leu Gln Ala Gln His His Glu Asp Gln His Gln Leu
        210                 215                 220

Phe Leu His Pro Leu Trp Asn Asp Asp Ile Ile Val Asp Val Asp Cys
225                 230                 235                 240

Trp Ser Ser Ser Thr Asn Val Val Ala Pro Pro Met Pro Ala Ser
                245                 250                 255

Pro Leu Trp Asp Ile Asp Asp Ala Phe Phe Cys Ser Asp Tyr Ser Leu
            260                 265                 270

Pro Leu Trp Gly
        275

<210> SEQ ID NO 18
<211> LENGTH: 103
<212> TYPE: PRT
<213> ORGANISM: Arabidopsis thaliana

<400> SEQUENCE: 18

Asn Arg Lys Gly Pro Trp Thr Glu Gln Glu Asp Ile Leu Leu Val Asn
1               5                   10                  15

Phe Val His Leu Phe Gly Asp Arg Arg Trp Asp Phe Ile Ala Lys Val
```

```
            20                  25                  30
Ser Gly Leu Asn Arg Thr Gly Lys Ser Cys Arg Leu Arg Trp Val Asn
        35                  40                  45

Tyr Leu His Pro Gly Leu Lys Arg Gly Lys Met Thr Pro Gln Glu Glu
    50                  55                  60

Arg Leu Val Leu Glu Leu His Ala Lys Trp Asn Arg Trp Ser Lys Ile
65                  70                  75                  80

Ala Arg Lys Leu Pro Gly Arg Thr Asp Asn Glu Ile Lys Asn Tyr Trp
                85                  90                  95

Arg Thr His Met Arg Lys Lys
            100

<210> SEQ ID NO 19
<211> LENGTH: 103
<212> TYPE: PRT
<213> ORGANISM: Arabidopsis thaliana

<400> SEQUENCE: 19

Tyr Arg Lys Gly Pro Trp Thr Glu Gln Glu Asp Ile Leu Leu Val Asn
1               5                   10                  15

Phe Val His Leu Phe Gly Asp Arg Arg Trp Asp Phe Val Ala Lys Val
            20                  25                  30

Ser Gly Leu Asn Arg Thr Gly Lys Ser Cys Arg Leu Arg Trp Val Asn
        35                  40                  45

Tyr Leu His Pro Gly Leu Lys Arg Gly Lys Met Thr Pro Gln Glu Glu
    50                  55                  60

Arg Leu Val Leu Glu Leu His Ala Lys Gly Asn Arg Trp Ser Lys Ile
65                  70                  75                  80

Ala Arg Lys Leu Pro Gly Arg Thr Asp Asn Glu Ile Lys Asn Tyr Trp
                85                  90                  95

Arg Thr His Met Arg Lys Lys
            100

<210> SEQ ID NO 20
<211> LENGTH: 103
<212> TYPE: PRT
<213> ORGANISM: Oryza sativa

<400> SEQUENCE: 20

Met Arg Lys Gly Pro Trp Thr Glu Gln Glu Asp Leu Gln Leu Val Cys
1               5                   10                  15

Thr Val Arg Leu Phe Gly Asp Arg Arg Trp Asp Phe Val Ala Lys Val
            20                  25                  30

Ser Gly Leu Asn Arg Thr Gly Lys Ser Cys Arg Leu Arg Trp Val Asn
        35                  40                  45

Tyr Leu His Pro Gly Leu Lys His Gly Lys Met Thr Pro Lys Glu Glu
    50                  55                  60

His Leu Ile Ile Glu Leu His Ala Arg Gly Asn Arg Trp Ser Lys Ile
65                  70                  75                  80

Ala Arg Arg Leu Pro Gly Arg Thr Asp Asn Glu Ile Lys Asn Tyr Trp
                85                  90                  95

Arg Thr His Met Arg Lys Lys
            100

<210> SEQ ID NO 21
<211> LENGTH: 103
<212> TYPE: PRT
```

<213> ORGANISM: Oryza sativa

<400> SEQUENCE: 21

```
Ile Arg Lys Gly Pro Trp Thr Glu Gln Glu Asp Leu Gln Leu Val Cys
1               5                   10                  15
Thr Val Arg Leu Phe Gly Glu Arg Trp Asp Phe Ile Ala Lys Val
            20                  25                  30
Ser Gly Leu Asn Arg Thr Gly Lys Ser Cys Arg Leu Arg Trp Val Asn
        35                  40                  45
Tyr Leu His Pro Gly Leu Lys Arg Gly Arg Met Ser Pro His Glu Glu
    50                  55                  60
Arg Leu Ile Leu Glu Leu His Ala Arg Gly Asn Arg Trp Ser Arg Ile
65                  70                  75                  80
Ala Arg Arg Leu Pro Gly Arg Thr Asp Asn Glu Ile Lys Asn Tyr Trp
                85                  90                  95
Arg Thr His Met Arg Lys Lys
                100
```

<210> SEQ ID NO 22
<211> LENGTH: 104
<212> TYPE: PRT
<213> ORGANISM: Triticum aestivum

<400> SEQUENCE: 22

```
Phe Arg Lys Gly Pro Trp Thr Glu Gln Glu Asp Met Lys Leu Ala Trp
1               5                   10                  15
Phe Val Arg Leu Phe Gly Glu Arg Trp Asp Phe Leu Ala Lys Val
            20                  25                  30
Ser Gly Leu Asn Arg Thr Gly Lys Ser Cys Arg Leu Arg Trp Val Asn
        35                  40                  45
Tyr Leu His Pro Asp Leu Lys Arg Gly Arg Met Ser Pro Glu Glu Glu
    50                  55                  60
Arg Leu Val Val Asp Leu His Ala Arg Trp Gly Asn Arg Trp Ser Arg
65                  70                  75                  80
Ile Ala Lys Ala Met Pro Gly Arg Thr Asp Asn Glu Ile Lys Asn Tyr
                85                  90                  95
Trp Arg Thr His Thr Arg Lys Leu
                100
```

<210> SEQ ID NO 23
<211> LENGTH: 104
<212> TYPE: PRT
<213> ORGANISM: Hordeum vulgare

<400> SEQUENCE: 23

```
Phe Arg Lys Gly Pro Trp Thr Glu Gln Glu Asp Met Lys Leu Ala Trp
1               5                   10                  15
Phe Val Arg Leu Phe Gly Glu Arg Trp Asp Phe Leu Ala Lys Val
            20                  25                  30
Ser Gly Leu Asn Arg Thr Gly Lys Ser Cys Arg Leu Arg Trp Val Asn
        35                  40                  45
Tyr Leu His Pro Asp Leu Lys Arg Gly Arg Met Thr Pro Asp Glu Glu
    50                  55                  60
Arg Leu Val Val Asp Leu His Ala Arg Trp Gly Asn Arg Trp Ser Arg
65                  70                  75                  80
Ile Ala Lys Ala Met Pro Gly Arg Thr Asp Asn Glu Ile Lys Asn Tyr
                85                  90                  95
```

```
Trp Arg Thr His Thr Arg Lys Leu
                100

<210> SEQ ID NO 24
<211> LENGTH: 103
<212> TYPE: PRT
<213> ORGANISM: Oryza sativa

<400> SEQUENCE: 24

Met Arg Lys Gly Pro Trp Thr Glu Gln Glu Asp Val Gln Leu Val Trp
1               5                   10                  15

Phe Val Arg Leu Leu Gly Glu Arg Arg Asp Phe Leu Ala Lys Val Ser
            20                  25                  30

Gly Leu Gln Arg Ser Gly Lys Ser Cys Arg Leu Arg Trp Val Asn Tyr
        35                  40                  45

Leu His Pro Gly Leu Lys Arg Gly Arg Met Ser Pro Glu Glu Glu Arg
    50                  55                  60

Met Val Val Gln Leu His Ala Lys Leu Gly Asn Arg Trp Ser Arg Ile
65                  70                  75                  80

Ala Lys Ser Ile Pro Gly Arg Thr Asp Asn Glu Ile Lys Asn Tyr Trp
                85                  90                  95

Arg Thr His Leu Arg Lys Leu
                100

<210> SEQ ID NO 25
<211> LENGTH: 65
<212> TYPE: PRT
<213> ORGANISM: Triticum aestivum

<400> SEQUENCE: 25

Met Lys Thr Lys Gln Ala Ser Lys Ala Lys Ala Ala Pro Ser Pro Gly
1               5                   10                  15

Lys Glu Glu Glu Ala Val Ala Pro Gly Gly Phe Arg Lys Gly Pro Trp
            20                  25                  30

Thr Glu Gln Glu Asp Met Lys Leu Ala Trp Phe Val Arg Leu Phe Gly
        35                  40                  45

Glu Arg Arg Trp Asp Phe Leu Ala Lys Val Ser Gly Leu Gln Gly Gly
    50                  55                  60

Gly
65

<210> SEQ ID NO 26
<211> LENGTH: 65
<212> TYPE: PRT
<213> ORGANISM: Triticum aestivum

<400> SEQUENCE: 26

Met Lys Thr Lys Gln Ala Ser Lys Ala Lys Ala Ala Pro Ser Pro Gly
1               5                   10                  15

Lys Glu Glu Glu Ala Val Ala Pro Gly Gly Phe Arg Lys Gly Pro Trp
            20                  25                  30

Thr Glu Gln Glu Asp Met Lys Leu Ala Trp Phe Val Arg Leu Phe Gly
        35                  40                  45

Glu Arg Arg Trp Asp Phe Leu Ala Lys Val Ser Gly Leu Gln Gly Gly
    50                  55                  60

Gly
65
```

<210> SEQ ID NO 27
<211> LENGTH: 64
<212> TYPE: PRT
<213> ORGANISM: Triticum aestivum

<400> SEQUENCE: 27

Met Lys Met Lys Gln Thr Lys Lys Thr Ser Ala Pro Ser Pro Gly Lys
1               5                   10                  15

Gln Glu Glu Ala Val Ala Pro Gly Gly Phe Arg Lys Gly Pro Trp Thr
            20                  25                  30

Glu Gln Glu Asp Met Lys Leu Ala Trp Phe Val Arg Leu Phe Gly Glu
        35                  40                  45

Arg Arg Trp Asp Phe Leu Ala Lys Val Ser Gly Leu Gln Gly Gly Gly
    50                  55                  60

<210> SEQ ID NO 28
<211> LENGTH: 30
<212> TYPE: DNA
<213> ORGANISM: Artificial
<220> FEATURE:
<223> OTHER INFORMATION: Variant MYB13 binding site

<400> SEQUENCE: 28
ttacgaggaa gttaggttcg acctaacgca                                    30

<210> SEQ ID NO 29
<211> LENGTH: 30
<212> TYPE: DNA
<213> ORGANISM: Artificial
<220> FEATURE:
<223> OTHER INFORMATION: Variant MYB13 binding site

<400> SEQUENCE: 29
tcgaccgaat aaagtttggt atgatgtgct                                    30

<210> SEQ ID NO 30
<211> LENGTH: 30
<212> TYPE: DNA
<213> ORGANISM: Artificial
<220> FEATURE:
<223> OTHER INFORMATION: Variant MYB13 binding site

<400> SEQUENCE: 30
cgagttaggt aactttacct tacgggcgta                                    30

<210> SEQ ID NO 31
<211> LENGTH: 30
<212> TYPE: DNA
<213> ORGANISM: Artificial
<220> FEATURE:
<223> OTHER INFORMATION: Variant MYB13 binding site

<400> SEQUENCE: 31
taggtgtacc taacaataag ttaggtagct                                    30

<210> SEQ ID NO 32
<211> LENGTH: 30
<212> TYPE: DNA
<213> ORGANISM: Artificial
<220> FEATURE:
<223> OTHER INFORMATION: Variant MYB13 binding site

<400> SEQUENCE: 32
gatgttgcta tttttggtt tgtacctgtc                                     30

<210> SEQ ID NO 33
<211> LENGTH: 30
<212> TYPE: DNA
<213> ORGANISM: Artificial
<220> FEATURE:
<223> OTHER INFORMATION: Variant MYB13 binding site

<400> SEQUENCE: 33
tgtaggatgg accgaacaaa ttaggtcata                                    30

<210> SEQ ID NO 34
<211> LENGTH: 30
<212> TYPE: DNA
<213> ORGANISM: Artificial
<220> FEATURE:
<223> OTHER INFORMATION: Variant MYB13 binding site

<400> SEQUENCE: 34
tcagatgcga cctaataaag ttaggtaggg                                    30

<210> SEQ ID NO 35
<211> LENGTH: 30
<212> TYPE: DNA
<213> ORGANISM: Artificial
<220> FEATURE:
<223> OTHER INFORMATION: Variant MYB13 binding site

<400> SEQUENCE: 35
acacctgacc tagaatatta ggttggacga                                    30

<210> SEQ ID NO 36
<211> LENGTH: 30
<212> TYPE: DNA
<213> ORGANISM: Artificial
<220> FEATURE:
<223> OTHER INFORMATION: Variant MYB13 binding site

<400> SEQUENCE: 36
cctacccaac ttattgttag gtacacctag                                    30

<210> SEQ ID NO 37
<211> LENGTH: 30
<212> TYPE: DNA
<213> ORGANISM: Artificial
<220> FEATURE:
<223> OTHER INFORMATION: Variant MYB13 binding site

<400> SEQUENCE: 37
ggaaatgaaa cctaacaaag ttaggtaaga                                    30

<210> SEQ ID NO 38
<211> LENGTH: 30
<212> TYPE: DNA
<213> ORGANISM: Artificial
<220> FEATURE:
<223> OTHER INFORMATION: Variant MYB13 binding site

<400> SEQUENCE: 38
accataccta acaaattagg tacgtcgggc                                    30

<210> SEQ ID NO 39
<211> LENGTH: 30
<212> TYPE: DNA
<213> ORGANISM: Artificial
<220> FEATURE:

<223> OTHER INFORMATION: Variant MYB13 binding site

<400> SEQUENCE: 39
ccgttaggtc ctggcttcca ctaacgtcta                                    30

<210> SEQ ID NO 40
<211> LENGTH: 30
<212> TYPE: DNA
<213> ORGANISM: Artificial
<220> FEATURE:
<223> OTHER INFORMATION: Variant MYB13 binding site

<400> SEQUENCE: 40
ggggttaggt acgccccacc cacctacccg                                    30

<210> SEQ ID NO 41
<211> LENGTH: 30
<212> TYPE: DNA
<213> ORGANISM: Artificial
<220> FEATURE:
<223> OTHER INFORMATION: Variant MYB13 binding site

<400> SEQUENCE: 41
acacctacac ctactttaat taggtatcga                                    30

<210> SEQ ID NO 42
<211> LENGTH: 29
<212> TYPE: DNA
<213> ORGANISM: Artificial
<220> FEATURE:
<223> OTHER INFORMATION: Variant MYB13 binding site

<400> SEQUENCE: 42
tcggtgtacc taacaataag ttaggtaga                                     29

<210> SEQ ID NO 43
<211> LENGTH: 30
<212> TYPE: DNA
<213> ORGANISM: Artificial
<220> FEATURE:
<223> OTHER INFORMATION: Variant MYB13 binding site

<400> SEQUENCE: 43
ctgatcatac caaactttat tcggtagagc                                    30

<210> SEQ ID NO 44
<211> LENGTH: 30
<212> TYPE: DNA
<213> ORGANISM: Artificial
<220> FEATURE:
<223> OTHER INFORMATION: Variant MYB13 binding site

<400> SEQUENCE: 44
tatccaactt atttttaggt acatttagga                                    30

<210> SEQ ID NO 45
<211> LENGTH: 9
<212> TYPE: DNA
<213> ORGANISM: Artificial
<220> FEATURE:
<223> OTHER INFORMATION: MYB13 binding sequence consensus
<220> FEATURE:
<221> NAME/KEY: n
<222> LOCATION: (1)..(1)
<223> OTHER INFORMATION: n=t or a
<220> FEATURE:
<221> NAME/KEY: misc_feature

```
<222> LOCATION: (1)..(2)
<223> OTHER INFORMATION: n is a, c, g, or t
<220> FEATURE:
<221> NAME/KEY: n
<222> LOCATION: (2)..(2)
<223> OTHER INFORMATION: n=g or a
<220> FEATURE:
<221> NAME/KEY: n
<222> LOCATION: (5)..(5)
<223> OTHER INFORMATION: n=a or t or c, preferably a
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: n
<222> LOCATION: (9)..(9)
<223> OTHER INFORMATION: n=a or t or c, preferably a
<220> FEATURE:
<221> NAME/KEY: misc_feature
<222> LOCATION: (9)..(9)
<223> OTHER INFORMATION: n is a, c, g, or t

<400> SEQUENCE: 45 nnttnggtn                                                                  9

<210> SEQ ID NO 46
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 46
tcgaccgaat aaagtttggt atgatgt                                             27

<210> SEQ ID NO 47
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 47
tcgagggaat aaagtttggt atgatgt                                             27

<210> SEQ ID NO 48
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 48
tcgagggaat aaagttcggt atgatgt                                             27

<210> SEQ ID NO 49
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 49
tcgagggaat aaagttgggt atgatgt                                             27

<210> SEQ ID NO 50
<211> LENGTH: 27
<212> TYPE: DNA
```

```
<213> ORGANISM: Artificial
<220> FEATURE:
<223> OTHER INFORMATION: OLIGONUCLEOTIDE

<400> SEQUENCE: 50
tcgagggaat aaagttaggt atgatgt                                              27

<210> SEQ ID NO 51
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 51
tcgagggaat aaaattaggt atgatgt                                              27

<210> SEQ ID NO 52
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 52
tcgagggaat aaacttaggt atgatgt                                              27

<210> SEQ ID NO 53
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 53
tcgagggaat aaatttaggt atgatgt                                              27

<210> SEQ ID NO 54
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 54
tcgagggaat aaagttaggg atgatgt                                              27

<210> SEQ ID NO 55
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 55
tcgagggaat aaagttagga atgatgt                                              27

<210> SEQ ID NO 56
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 56
tcgagggaat aaagttaggc atgatgt                                              27
```

<210> SEQ ID NO 57
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 57
tcgagggaat aaagttaggt ttgatgt                                    27

<210> SEQ ID NO 58
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 58
tcgagggaat aaagttaggt gtgatgt                                    27

<210> SEQ ID NO 59
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 59
tcgagggaat aaagttaggt ctgatgt                                    27

<210> SEQ ID NO 60
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 60
tcgagggaat aaagttaggt aagatgt                                    27

<210> SEQ ID NO 61
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 61
tcgagggaat aaagttaggt acgatgt                                    27

<210> SEQ ID NO 62
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 62
tcgagggaat aaagttaggt aggatgt                                    27

<210> SEQ ID NO 63
<211> LENGTH: 27
<212> TYPE: DNA
<213> ORGANISM: Artificial
<220> FEATURE:

-continued

<223> OTHER INFORMATION: OLIGONUCLEOTIDE

<400> SEQUENCE: 63
tcgagggaat aacgttaggt atgatgt                                   27

<210> SEQ ID NO 64
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 64
tcgagggaat aaggttaggt atgatgt                                   27

<210> SEQ ID NO 65
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 65
tcgagggaat aatgttaggt atgatgt                                   27

<210> SEQ ID NO 66
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 66
tcgagggaat atagttaggt atgatgt                                   27

<210> SEQ ID NO 67
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 67
tcgagggaat acagttaggt atgatgt                                   27

<210> SEQ ID NO 68
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 68
tcgagggaat agagttaggt atgatgt                                   27

<210> SEQ ID NO 69
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 69
tcgagggaat agagggaggt atgatgt                                   27

```
<210> SEQ ID NO 70
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 70
tcgagggaat agagttattt atgatgt                                           27

<210> SEQ ID NO 71
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 71
tcgagggaat accgttaggt gtgatgt                                           27

<210> SEQ ID NO 72
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 72
tcgagggaat accgtttggt gtgatgt                                           27

<210> SEQ ID NO 73
<211> LENGTH: 7
<212> TYPE: DNA
<213> ORGANISM: Artificial
<220> FEATURE:
<223> OTHER INFORMATION: OLIGONUCLEOTIDE
<220> FEATURE:
<221> NAME/KEY: D
<222> LOCATION: (1)..(1)
<223> OTHER INFORMATION: D=A or G or T, preferably a or g
<220> FEATURE:
<221> NAME/KEY: H
<222> LOCATION: (4)..(4)
<223> OTHER INFORMATION: H=A or T or C, preferably A

<400> SEQUENCE: 73 dtthggt                                                                 7

<210> SEQ ID NO 74
<211> LENGTH: 11
<212> TYPE: DNA
<213> ORGANISM: Artificial
<220> FEATURE:
<223> OTHER INFORMATION: OLIGONUCLEOTIDE
<220> FEATURE:
<221> NAME/KEY: R
<222> LOCATION: (3)..(3)
<223> OTHER INFORMATION: R=A OR G
<220> FEATURE:
<221> NAME/KEY: R
<222> LOCATION: (11)..(11)
<223> OTHER INFORMATION: R=A OR G

<400> SEQUENCE: 74
aarttaggta r                                                            11

<210> SEQ ID NO 75
<211> LENGTH: 27
<212> TYPE: DNA
```

```
<213> ORGANISM: Artificial
<220> FEATURE:
<223> OTHER INFORMATION: Regions of 6-SFT and 1-SST genes comprising
      MYB13 binding sites

<400> SEQUENCE: 75
tcgaccgaat aaagtttggt atgatgt                                            27

<210> SEQ ID NO 76
<211> LENGTH: 30
<212> TYPE: DNA
<213> ORGANISM: Hordeum vulgare

<400> SEQUENCE: 76
caaagtttca ctatatgtta ggtacttgtt                                         30

<210> SEQ ID NO 77
<211> LENGTH: 27
<212> TYPE: DNA
<213> ORGANISM: Hordeum vulgare

<400> SEQUENCE: 77
aagcttcaaa gccatttggt aactagc                                            27

<210> SEQ ID NO 78
<211> LENGTH: 28
<212> TYPE: DNA
<213> ORGANISM: Hordeum vulgare

<400> SEQUENCE: 78
tcaactccga gagggtttgg tagattct                                           28

<210> SEQ ID NO 79
<211> LENGTH: 31
<212> TYPE: DNA
<213> ORGANISM: Triticum aestivum

<400> SEQUENCE: 79
ggtcaagact gtgttaggtt cggttgtaat t                                       31

<210> SEQ ID NO 80
<211> LENGTH: 27
<212> TYPE: DNA
<213> ORGANISM: Triticum aestivum

<400> SEQUENCE: 80
cggtcaagac tgtgttaggt tcggctg                                            27

<210> SEQ ID NO 81
<211> LENGTH: 27
<212> TYPE: DNA
<213> ORGANISM: Triticum aestivum

<400> SEQUENCE: 81
gaactccaag agagtttggt agattgt                                            27

<210> SEQ ID NO 82
<211> LENGTH: 27
<212> TYPE: DNA
<213> ORGANISM: Triticum aestivum

<400> SEQUENCE: 82
tggccaagac tgtgttaggt ttggctg                                            27
```

-continued

<210> SEQ ID NO 83
<211> LENGTH: 27
<212> TYPE: DNA
<213> ORGANISM: Triticum aestivum

<400> SEQUENCE: 83
cggccaagac tgtgttaggt ttggctg                                        27

<210> SEQ ID NO 84
<211> LENGTH: 27
<212> TYPE: DNA
<213> ORGANISM: Triticum aestivum

<400> SEQUENCE: 84
cggccaagac tgtgttaggt tctgctg                                        27

<210> SEQ ID NO 85
<211> LENGTH: 27
<212> TYPE: DNA
<213> ORGANISM: Triticum aestivum

<400> SEQUENCE: 85
gaactccaag agagtttggt agattgt                                        27

<210> SEQ ID NO 86
<211> LENGTH: 27
<212> TYPE: DNA
<213> ORGANISM: Triticum aestivum

<400> SEQUENCE: 86
ccatcgggtt tgcattaggt tcataag                                        27

<210> SEQ ID NO 87
<211> LENGTH: 29
<212> TYPE: DNA
<213> ORGANISM: Triticum aestivum

<400> SEQUENCE: 87
gggacgcatg catgttcggt aagaaacaa                                      29

<210> SEQ ID NO 88
<211> LENGTH: 30
<212> TYPE: DNA
<213> ORGANISM: Artificial
<220> FEATURE:
<223> OTHER INFORMATION: OLIGONUCLEOTIDE

<400> SEQUENCE: 88
gagaatttgc cgtttatcta gaaattacct                                     30

<210> SEQ ID NO 89
<211> LENGTH: 12
<212> TYPE: DNA
<213> ORGANISM: Artificial
<220> FEATURE:
<223> OTHER INFORMATION: oligonucleotide

<400> SEQUENCE: 89
tatgttaggt ac                                                        12

<210> SEQ ID NO 90
<211> LENGTH: 27
<212> TYPE: DNA
<213> ORGANISM: Artificial

```
<220> FEATURE:
<223> OTHER INFORMATION: OLIGONUCLEOTIDE

<400> SEQUENCE: 90
tcgagggaat aaagttagtt atgatgt                                        27

<210> SEQ ID NO 91
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 91
tcgagggaat tataacggtt ttttgat                                        27

<210> SEQ ID NO 92
<211> LENGTH: 28
<212> TYPE: DNA
<213> ORGANISM: Artificial
<220> FEATURE:
<223> OTHER INFORMATION: OLIGONUCLEOTIDE

<400> SEQUENCE: 92
tcgagggaat aaggtaggtg gatgatgt                                       28

<210> SEQ ID NO 93
<211> LENGTH: 18
<212> TYPE: DNA
<213> ORGANISM: Artificial
<220> FEATURE:
<223> OTHER INFORMATION: FORWARD PRIMER

<400> SEQUENCE: 93
agttgcaccg ggtggttt                                                  18

<210> SEQ ID NO 94
<211> LENGTH: 18
<212> TYPE: DNA
<213> ORGANISM: Artificial
<220> FEATURE:
<223> OTHER INFORMATION: FORWARD PRIMER

<400> SEQUENCE: 94
agttgcaccg ggtggttt                                                  18

<210> SEQ ID NO 95
<211> LENGTH: 18
<212> TYPE: DNA
<213> ORGANISM: Artificial
<220> FEATURE:
<223> OTHER INFORMATION: FORWARD PRIMER

<400> SEQUENCE: 95
ggtttccgga agggacca                                                  18

<210> SEQ ID NO 96
<211> LENGTH: 18
<212> TYPE: DNA
<213> ORGANISM: Artificial
<220> FEATURE:
<223> OTHER INFORMATION: FORWARD PRIMER

<400> SEQUENCE: 96
ggtttccgga agggacca                                                  18
```

<210> SEQ ID NO 97
<211> LENGTH: 19
<212> TYPE: DNA
<213> ORGANISM: Artificial
<220> FEATURE:
<223> OTHER INFORMATION: FORWARD PRIMER

<400> SEQUENCE: 97
ggaggaagca gttgcaccc                                              19

<210> SEQ ID NO 98
<211> LENGTH: 19
<212> TYPE: DNA
<213> ORGANISM: Artificial
<220> FEATURE:
<223> OTHER INFORMATION: FORWARD PRIMER

<400> SEQUENCE: 98
ggaggaagca gttgcaccc                                              19

<210> SEQ ID NO 99
<211> LENGTH: 20
<212> TYPE: DNA
<213> ORGANISM: Artificial
<220> FEATURE:
<223> OTHER INFORMATION: FORWARD PRIMER

<400> SEQUENCE: 99
ggtcttcgga cgcacttctg                                             20

<210> SEQ ID NO 100
<211> LENGTH: 18
<212> TYPE: DNA
<213> ORGANISM: Artificial
<220> FEATURE:
<223> OTHER INFORMATION: FORWARD PRIMER

<400> SEQUENCE: 100
acaacgccac cggcacta                                               18

<210> SEQ ID NO 101
<211> LENGTH: 20
<212> TYPE: DNA
<213> ORGANISM: Artificial
<220> FEATURE:
<223> OTHER INFORMATION: FORWARD PRIMER

<400> SEQUENCE: 101
gagatggact cagcgcacaa                                             20

<210> SEQ ID NO 102
<211> LENGTH: 23
<212> TYPE: DNA
<213> ORGANISM: Artificial
<220> FEATURE:
<223> OTHER INFORMATION: FORWARD PRIMER

<400> SEQUENCE: 102
catatgtaaa cgattccgca cag                                         23

<210> SEQ ID NO 103
<211> LENGTH: 27
<212> TYPE: DNA
<213> ORGANISM: Artificial
<220> FEATURE:
<223> OTHER INFORMATION: FORWARD PRIMER -continued

<400> SEQUENCE: 103
acgtattaac caagaactca tggagac                                27

<210> SEQ ID NO 104
<211> LENGTH: 22
<212> TYPE: DNA
<213> ORGANISM: Artificial
<220> FEATURE:
<223> OTHER INFORMATION: FORWARD PRIMER3

<400> SEQUENCE: 104
gcacacgtgc tttgcagata ag                                    22

<210> SEQ ID NO 105
<211> LENGTH: 23
<212> TYPE: DNA
<213> ORGANISM: Artificial
<220> FEATURE:
<223> OTHER INFORMATION: FORWARD PRIMER

<400> SEQUENCE: 105
gaactgtctg gattgtccca tca                                   23

<210> SEQ ID NO 106
<211> LENGTH: 19
<212> TYPE: DNA
<213> ORGANISM: Artificial
<220> FEATURE:
<223> OTHER INFORMATION: REVERSE PRIMER

<400> SEQUENCE: 106
ccgtccggtt aagacctga                                        19

<210> SEQ ID NO 107
<211> LENGTH: 19
<212> TYPE: DNA
<213> ORGANISM: Artificial
<220> FEATURE:
<223> OTHER INFORMATION: REVERSE PRIMER

<400> SEQUENCE: 107
gccaccttgc aaacctgac                                        19

<210> SEQ ID NO 108
<211> LENGTH: 19
<212> TYPE: DNA
<213> ORGANISM: Artificial
<220> FEATURE:
<223> OTHER INFORMATION: REVERSE PRIMER

<400> SEQUENCE: 108
ccgtccggtt gagacctga                                        19

<210> SEQ ID NO 109
<211> LENGTH: 19
<212> TYPE: DNA
<213> ORGANISM: Artificial
<220> FEATURE:
<223> OTHER INFORMATION: REVERSE PRIMER

<400> SEQUENCE: 109
gccaccttgc aaacctgac                                        19

<210> SEQ ID NO 110

```
<211> LENGTH: 19
<212> TYPE: DNA
<213> ORGANISM: Artificial
<220> FEATURE:
<223> OTHER INFORMATION: REVERSE PRIMER

<400> SEQUENCE: 110
ccgtccggtt gagacctga                                              19

<210> SEQ ID NO 111
<211> LENGTH: 19
<212> TYPE: DNA
<213> ORGANISM: Artificial
<220> FEATURE:
<223> OTHER INFORMATION: REVERSE PRIMER

<400> SEQUENCE: 111
gccaccttgc aaacctgac                                              19

<210> SEQ ID NO 112
<211> LENGTH: 19
<212> TYPE: DNA
<213> ORGANISM: Artificial
<220> FEATURE:
<223> OTHER INFORMATION: REVERSE PRIMER

<400> SEQUENCE: 112
cgccacatcg gtagcatgt                                              19

<210> SEQ ID NO 113
<211> LENGTH: 25
<212> TYPE: DNA
<213> ORGANISM: Artificial
<220> FEATURE:
<223> OTHER INFORMATION: REVERSE PRIMER

<400> SEQUENCE: 113
gacgagtcca tatcatgcac tacaa                                       25

<210> SEQ ID NO 114
<211> LENGTH: 22
<212> TYPE: DNA
<213> ORGANISM: Artificial
<220> FEATURE:
<223> OTHER INFORMATION: REVERSE PRIMER

<400> SEQUENCE: 114
gccttccttg gtgagcttct tt                                          22

<210> SEQ ID NO 115
<211> LENGTH: 23
<212> TYPE: DNA
<213> ORGANISM: Artificial
<220> FEATURE:
<223> OTHER INFORMATION: REVERSE PRIMER

<400> SEQUENCE: 115
gcagaacatg acccaaggat aga                                         23

<210> SEQ ID NO 116
<211> LENGTH: 26
<212> TYPE: DNA
<213> ORGANISM: Artificial
<220> FEATURE:
<223> OTHER INFORMATION: REVERSE PRIMER

<400> SEQUENCE: 116
```
tcaaatactt ttgtagggct gctctc        26

<210> SEQ ID NO 117
<211> LENGTH: 22
<212> TYPE: DNA
<213> ORGANISM: Artificial
<220> FEATURE:
<223> OTHER INFORMATION: REVERSE PRIMER

<400> SEQUENCE: 117
gccctcaagc tcaaccataa ct        22

<210> SEQ ID NO 118
<211> LENGTH: 23
<212> TYPE: DNA
<213> ORGANISM: Artificial
<220> FEATURE:
<223> OTHER INFORMATION: REVERSE PRIMER

<400> SEQUENCE: 118
acagtaggcc cacaccaatg tac        23

<210> SEQ ID NO 119
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 119
ttcctcgagt caagtggctc t        21

<210> SEQ ID NO 120
<211> LENGTH: 24
<212> TYPE: DNA
<213> ORGANISM: Artificial
<220> FEATURE:
<223> OTHER INFORMATION: OLIGONUCLEOTIDE

<400> SEQUENCE: 120
ctgagagtgc accatatgga cata        24

<210> SEQ ID NO 121
<211> LENGTH: 22
<212> TYPE: DNA
<213> ORGANISM: Artificial
<220> FEATURE:
<223> OTHER INFORMATION: OLIGONUCLEOTIDE

<400> SEQUENCE: 121
ggatagtgtt gaacatacgt tt        22

<210> SEQ ID NO 122
<211> LENGTH: 31
<212> TYPE: DNA
<213> ORGANISM: Artificial
<220> FEATURE:
<223> OTHER INFORMATION: OLIGONUCLEOTIDE

<400> SEQUENCE: 122
tgtcgtataa tgcattgttt cttaccgaac a        31

<210> SEQ ID NO 123
<211> LENGTH: 56
<212> TYPE: DNA

```
<213> ORGANISM: Artificial
<220> FEATURE:
<223> OTHER INFORMATION: OLIGONUCLEOTIDE

<400> SEQUENCE: 123
ccgacaactg ttttgtggtg aattacaacc gattttaaca cagtcttgac cgtgca        56

<210> SEQ ID NO 124
<211> LENGTH: 14
<212> TYPE: DNA
<213> ORGANISM: Artificial
<220> FEATURE:
<223> OTHER INFORMATION: OLIGONUCLEOTIDE

<400> SEQUENCE: 124
tgttaggttc ggtt                                                       14

<210> SEQ ID NO 125
<211> LENGTH: 14
<212> TYPE: DNA
<213> ORGANISM: Artificial
<220> FEATURE:
<223> OTHER INFORMATION: OLIGONUCLEOTDIE

<400> SEQUENCE: 125
tgttaaaatc ggtt                                                       14

<210> SEQ ID NO 126
<211> LENGTH: 49
<212> TYPE: DNA
<213> ORGANISM: Artificial
<220> FEATURE:
<223> OTHER INFORMATION: OLIGONUCLEOTIDE

<400> SEQUENCE: 126
tgtcgtataa tgcattgttt cttttggaac atgcatgcgt cccatgcaa                 49

<210> SEQ ID NO 127
<211> LENGTH: 11
<212> TYPE: DNA
<213> ORGANISM: Artificial
<220> FEATURE:
<223> OTHER INFORMATION: OLIGONUCLEOTIDE

<400> SEQUENCE: 127
atgttcggta a                                                          11

<210> SEQ ID NO 128
<211> LENGTH: 11
<212> TYPE: DNA
<213> ORGANISM: Artificial
<220> FEATURE:
<223> OTHER INFORMATION: OLIGONUCLEOTIDE

<400> SEQUENCE: 128
atgttccaaa a                                                          11

<210> SEQ ID NO 129
<211> LENGTH: 12
<212> TYPE: DNA
<213> ORGANISM: Artificial
<220> FEATURE:
<223> OTHER INFORMATION: OLIGONUCLEOTIDE

<400> SEQUENCE: 129
tatgttaggt ac                                                         12
```

```
<210> SEQ ID NO 130
<211> LENGTH: 53
<212> TYPE: DNA
<213> ORGANISM: Artificial
<220> FEATURE:
<223> OTHER INFORMATION: Oligonucleotide

<400> SEQUENCE: 130
ccgctatgtt aggtacatta tgttaggtac ggatagtgtt gaacatacgg ttt            53

<210> SEQ ID NO 131
<211> LENGTH: 69
<212> TYPE: DNA
<213> ORGANISM: Artificial
<220> FEATURE:
<223> OTHER INFORMATION: OLIGONUCLEOTIDE
<220> FEATURE:
<221> NAME/KEY: n
<222> LOCATION: (20)..(49)
<223> OTHER INFORMATION: n=a or c or g or t
<220> FEATURE:
<221> NAME/KEY: misc_feature
<222> LOCATION: (20)..(49)
<223> OTHER INFORMATION: n is a, c, g, or t

<400> SEQUENCE: 131
ggatccctcg agctgcagcn nnnnnnnnnn nnnnnnnnnn nnnnnnnnng ctagccgatc    60
ggagctcgg                                                            69

<210> SEQ ID NO 132
<211> LENGTH: 11
<212> TYPE: DNA
<213> ORGANISM: Artificial
<220> FEATURE:
<223> OTHER INFORMATION: OLIGONUCLEOTIDE

<400> SEQUENCE: 132
gcattaggtt c                                                         11

<210> SEQ ID NO 133
<211> LENGTH: 7
<212> TYPE: DNA
<213> ORGANISM: Artificial
<220> FEATURE:
<223> OTHER INFORMATION: OLIGONUCLEOTIDE

<400> SEQUENCE: 133 gttaggt                                                               7

<210> SEQ ID NO 134
<211> LENGTH: 9
<212> TYPE: DNA
<213> ORGANISM: Artificial
<220> FEATURE:
<223> OTHER INFORMATION: OLIGONUCLEOTIDE

<400> SEQUENCE: 134 agttagtta                                                             9

<210> SEQ ID NO 135
<211> LENGTH: 14
<212> TYPE: DNA
<213> ORGANISM: Artificial
<220> FEATURE:
<223> OTHER INFORMATION: OLIGONUCLEOTIDE
```

```
<400> SEQUENCE: 135
tataacggtt tttt                                                    14

<210> SEQ ID NO 136
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 136
tcgagggaat aaaaacggtt atgatgt                                      27

<210> SEQ ID NO 137
<211> LENGTH: 28
<212> TYPE: DNA
<213> ORGANISM: Artificial
<220> FEATURE:
<223> OTHER INFORMATION: OLIGONUCLEOTIDE

<400> SEQUENCE: 137
tcgagggaat agggttggtg gatgatgt                                     28

<210> SEQ ID NO 138
<211> LENGTH: 28
<212> TYPE: DNA
<213> ORGANISM: Artificial
<220> FEATURE:
<223> OTHER INFORMATION: OLIGONUCLEOTIDE

<400> SEQUENCE: 138
tcgagggaat aaagttaggt tatgatgt                                     28

<210> SEQ ID NO 139
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 139
tcgagggaat aatttttggt ttgatgt                                      27

<210> SEQ ID NO 140
<211> LENGTH: 27
<212> TYPE: DNA
<213> ORGANISM: Artificial
<220> FEATURE:
<223> OTHER INFORMATION: OLIGONUCLEOTIDE

<400> SEQUENCE: 140
tcgagggaat aaaatttcaa atgatgt                                      27

<210> SEQ ID NO 141
<211> LENGTH: 21
<212> TYPE: DNA
<213> ORGANISM: Artificial
<220> FEATURE:
<223> OTHER INFORMATION: OLIGONUCLEOTIDE

<400> SEQUENCE: 141
gcgaggagtc tggtggcaac t                                            21

<210> SEQ ID NO 142
<211> LENGTH: 20
```

```
<212> TYPE: DNA
<213> ORGANISM: Artificial
<220> FEATURE:
<223> OTHER INFORMATION: OLIGONUCLEOTIDE

<400> SEQUENCE: 142
aagcagagca cggccggtaa                                              20

<210> SEQ ID NO 143
<211> LENGTH: 226
<212> TYPE: PRT
<213> ORGANISM: Festuca arundinacea

<400> SEQUENCE: 143
```

| Met | His | Gly | Ile | Gln | Ile | Tyr | Met | Val | Met | Val | Phe | Cys | Val | Leu | Thr |
|---|---|---|---|---|---|---|---|---|---|---|---|---|---|---|---|
| 1 | | | | 5 | | | | | 10 | | | | | 15 | |

| Arg | Leu | Leu | Ser | Thr | Arg | Thr | Val | Leu | Leu | Leu | Val | Gly | Val | Ala |
|---|---|---|---|---|---|---|---|---|---|---|---|---|---|---|
| | | | 20 | | | | | 25 | | | | | 30 | |

| Gly | Leu | Asn | Arg | Thr | Gly | Lys | Ser | Cys | Arg | Leu | Arg | Trp | Val | Asn | Tyr |
|---|---|---|---|---|---|---|---|---|---|---|---|---|---|---|---|
| | | | 35 | | | | | 40 | | | | | 45 | | |

| Leu | His | Pro | Asp | Leu | Lys | Arg | Gly | Arg | Met | Thr | Pro | Asp | Glu | Glu | Arg |
|---|---|---|---|---|---|---|---|---|---|---|---|---|---|---|---|
| | 50 | | | | | 55 | | | | | 60 | | | | |

| Leu | Val | Val | Glu | Leu | His | Ala | Lys | Trp | Gly | Asn | Arg | Trp | Ser | Arg | Ile |
|---|---|---|---|---|---|---|---|---|---|---|---|---|---|---|---|
| 65 | | | | | 70 | | | | | 75 | | | | | 80 |

| Ala | Lys | Ala | Met | Pro | Gly | Arg | Thr | Asp | Asn | Glu | Ile | Lys | Asn | Tyr | Trp |
|---|---|---|---|---|---|---|---|---|---|---|---|---|---|---|---|
| | | | | 85 | | | | | 90 | | | | | 95 | |

| Arg | Thr | His | Thr | Arg | Lys | Gln | Asp | Lys | Thr | Gln | Arg | Ser | Val | Ser | Ala |
|---|---|---|---|---|---|---|---|---|---|---|---|---|---|---|---|
| | | | 100 | | | | | 105 | | | | | 110 | | |

| Ser | Ala | Ser | Thr | Thr | Thr | Ser | Met | Ser | Ala | Ala | Ser | Pro | Ala | Thr | Ser |
|---|---|---|---|---|---|---|---|---|---|---|---|---|---|---|---|
| | | 115 | | | | | 120 | | | | | 125 | | | |

| Ser | Ser | Ser | Ser | Asn | Asn | Asn | Asp | Asp | Gln | Cys | His | His | Gly | Asp |
|---|---|---|---|---|---|---|---|---|---|---|---|---|---|---|
| | 130 | | | | | 135 | | | | | 140 | | | |

| Asp | Glu | Thr | Ala | Ala | Thr | Ala | Pro | Ser | Gln | Glu | Pro | Leu | Ile | Tyr | Thr |
|---|---|---|---|---|---|---|---|---|---|---|---|---|---|---|---|
| 145 | | | | | 150 | | | | | 155 | | | | | 160 |

| Gly | Gly | Ile | Gly | Met | Asp | Ser | Leu | Leu | Trp | Asn | Asp | Pro | Ile | Asp | Ser |
|---|---|---|---|---|---|---|---|---|---|---|---|---|---|---|---|
| | | | | 165 | | | | | 170 | | | | | 175 | |

| Tyr | Ala | Trp | Ser | Asn | Thr | Ala | Ala | Ala | Thr | Ala | Ser | Met | Met | Val | Val |
|---|---|---|---|---|---|---|---|---|---|---|---|---|---|---|---|
| | | | 180 | | | | | 185 | | | | | 190 | | |

| Pro | Ser | Pro | Val | Trp | Asp | Tyr | Cys | Cys | Ser | Asp | Ser | Leu | Trp | Gly |
|---|---|---|---|---|---|---|---|---|---|---|---|---|---|---|
| | | 195 | | | | | 200 | | | | | 205 | | |

| Thr | Ile | Asp | Asp | Glu | Val | Ala | Glu | Tyr | Lys | Lys | Met | Leu | Gly | Val | Ser |
|---|---|---|---|---|---|---|---|---|---|---|---|---|---|---|---|
| | | 210 | | | | | 215 | | | | | 220 | | | |

| Ala | Ser |
|---|---|
| 225 | |

```
<210> SEQ ID NO 144
<211> LENGTH: 238
<212> TYPE: PRT
<213> ORGANISM: Triticum aestivum

<400> SEQUENCE: 144
```

| Met | Val | Thr | Val | Gln | Asp | Glu | Met | Arg | Lys | Gly | Pro | Trp | Thr | Glu | Gln |
|---|---|---|---|---|---|---|---|---|---|---|---|---|---|---|---|
| 1 | | | | 5 | | | | | 10 | | | | | 15 | |

| Glu | Asp | Leu | Gln | Leu | Val | Cys | Thr | Val | Arg | Leu | Phe | Gly | Asp | His | Arg |
|---|---|---|---|---|---|---|---|---|---|---|---|---|---|---|---|
| | | | 20 | | | | | 25 | | | | | 30 | | |

| Trp | Asp | Phe | Val | Ala | Lys | Val | Ser | Gly | Leu | Asn | Arg | Thr | Gly | Lys | Ser |
|---|---|---|---|---|---|---|---|---|---|---|---|---|---|---|---|
| | | | 35 | | | | | 40 | | | | | 45 | | |

```
Cys Arg Leu Arg Trp Val Asn Tyr Leu His Pro Gly Leu Lys His Gly
 50                  55                  60

Arg Met Ser Pro Gln Glu His Leu Ile Ile Glu Leu His Ala Arg
 65                  70                  75                  80

Trp Gly Asn Arg Trp Ser Arg Ile Ala Arg Arg Leu Pro Gly Arg Thr
                 85                  90                  95

Asp Asn Glu Ile Lys Asn Tyr Trp Arg Thr His Met Arg Lys Lys Ala
                100                 105                 110

Gln Glu Arg Lys Ile Asp Met Ser Pro Ser Ser Ser Ser Ser Ser Phe
                115                 120                 125

Thr Tyr Gln Ser Cys Leu Leu Glu Thr Ala Pro Ile Ile Arg Met Asp
130                 135                 140

Gly Gly Ser Thr His Asn Gly Thr Thr Cys Phe Ser Ser Val Leu Lys
145                 150                 155                 160

Ser Asn Gln Ser Val Met Asp Gly Tyr Ser Met Asp Gln Ile Trp Lys
                165                 170                 175

Glu Ile Glu Ala Pro Ala Met Leu Pro Ile Asp Lys Ala Cys Ser
                180                 185                 190

Asn Leu Pro Cys Pro Leu Leu Pro Ser Pro Met Gly Asp Arg Tyr Cys
                195                 200                 205

Pro Pro Glu Val Val Trp Lys Met Asp Asn Gly Asp Leu Lys Met Leu
210                 215                 220

Ala Pro Gln Phe Gly Tyr Gly Asn Gly Glu Arg Ser Cys Tyr
225                 230                 235

<210> SEQ ID NO 145
<211> LENGTH: 238
<212> TYPE: PRT
<213> ORGANISM: Festuca pratensis

<400> SEQUENCE: 145

Met Val Thr Val Arg Glu Glu Thr Arg Lys Gly Leu Trp Thr Glu Gln
  1               5                  10                  15

Glu Asp Leu Gln Leu Val Cys Thr Val Arg Leu Phe Gly Glu Arg Arg
                 20                  25                  30

Trp Asp Phe Val Ala Lys Val Ser Gly Leu Asn Arg Thr Gly Lys Ser
                 35                  40                  45

Cys Arg Leu Arg Trp Val Asn Tyr Leu His Pro Gly Leu Lys Arg Gly
 50                  55                  60

Arg Met Thr Pro His Glu Glu Arg Leu Ile Leu Glu Leu His Ala Arg
 65                  70                  75                  80

Trp Gly Asn Arg Trp Ser Arg Ile Ala Arg Arg Leu Pro Gly Arg Thr
                 85                  90                  95

Asp Asn Glu Ile Lys Asn Tyr Trp Arg Thr His Met Arg Lys Lys Ala
                100                 105                 110

Gln Glu Arg Lys Lys Asn Met Ser Pro Ser Ser Ser Ser Ser Ser Leu
                115                 120                 125

Thr Tyr Gln Ser Cys His Pro Glu Thr Pro Ser Ile Leu Gly Ile Asp
130                 135                 140

Glu Gln Glu Leu His Gly Gly Ser Ser Cys Ile Thr Ser Ile Leu Lys
145                 150                 155                 160

Gly Thr Pro Ala Asp Met Asp Gly Tyr Leu Met Asp Gln Ile Trp Met
                165                 170                 175

Glu Ile Glu Ala Pro Ser Ala Pro Ser Phe His Asn Gly Lys Asp Ser
                180                 185                 190
```

```
Ala Tyr Ser Ser Pro Ser Gly Pro Leu Leu Pro Ser Pro Leu Trp Asp
            195                 200                 205

His Tyr Cys Pro Glu Glu His Leu Lys Ile Asp Asp Glu Ile Lys Met
    210                 215                 220

Ala Pro Gln Phe Gly Tyr Ser Lys Gly Met Gly Pro Cys Tyr
225                 230                 235

<210> SEQ ID NO 146
<211> LENGTH: 203
<212> TYPE: PRT
<213> ORGANISM: Dactylis glomerata

<400> SEQUENCE: 146

Gly Trp Arg Ala Gly Leu Asn Arg Thr Gly Lys Ser Cys Arg Leu Arg
1               5                   10                  15

Trp Val Asn Tyr Leu His Pro Asp Leu Lys Arg Gly Arg Met Asn Pro
            20                  25                  30

Asp Glu Glu Arg Leu Val Val Glu Leu His Ala Lys Trp Gly Asn Arg
        35                  40                  45

Trp Ser Arg Ile Ala Lys Ala Met Pro Gly Arg Thr Asp Asn Glu Ile
    50                  55                  60

Lys Asn Tyr Trp Arg Thr His Thr Arg Lys Gln Asp Lys Thr Gln Arg
65                  70                  75                  80

Ala Ser Thr Thr Ala Gly Ser Thr Thr Thr Ser Thr Thr Thr Ser Met
                85                  90                  95

Ser Ala Ala Ser Pro Thr Ala Ser Ser Ser Ser Ser Asn Asp Asn
            100                 105                 110

Asp Ala Asp Glu Gln Ser His Arg Ser Asp Lys Ala Glu Ala Ala Thr
        115                 120                 125

Val Val Ser Gln Glu Asn Gln Val Leu Tyr Thr Gly Ile Gly Met Asp
    130                 135                 140

Asn His Leu Phe Trp Asn Asp Ile Asp Met Gly Gly Ala Trp Thr Ser
145                 150                 155                 160

Val Ala Gly Met Gly Thr Ala Pro Cys Met Val Pro Ser Ser Pro Val
                165                 170                 175

Trp Asp Tyr Cys Cys Ser Asp Ser Leu Trp Gly Pro Val Asp Asp Glu
            180                 185                 190

Val Ala Glu Tyr Lys Lys Met Ile Gly Ala Ser
        195                 200

<210> SEQ ID NO 147
<211> LENGTH: 157
<212> TYPE: PRT
<213> ORGANISM: Pseudoroegneria spicata

<400> SEQUENCE: 147

Ala Lys Ala Met Pro Gly Arg Thr Asp Asn Glu Ile Lys Asn Tyr Trp
1               5                   10                  15

Arg Thr His Thr Arg Lys Leu His Lys Asp Thr Arg Ala Ala Ala Asp
            20                  25                  30

Gly Val Ala Ala Ser Ala Ser Thr Thr Ser Thr Ser Met Ser Ala
        35                  40                  45

Ala Ser Pro Ala Thr Thr Ser Ser Ser Ser Ser Thr Thr Asp Asn
    50                  55                  60

Asp Asn Leu Ser His His Gly His Gly Asp Gln Glu Thr Ala Ala Ser
65                  70                  75                  80
```

```
His Glu Gln Ala Asp His Gln Leu Leu Tyr Thr Ala Gly Ile Gly Met
                85                  90                  95

Asp Ser His Leu Leu Trp Asn Asp Ala Phe Met Asp Thr Tyr Ala Trp
            100                 105                 110

Gly Ala Ala Ala Pro Ser Met Ile Val Pro Pro Ser Ser Pro Val
        115                 120                 125

Trp Asp Tyr Cys Cys Ser Asp Ser Leu Trp Gly Ile Gly Asp Asp Glu
    130                 135                 140

Val Glu Tyr Lys Lys Met Leu Ala Val Ala Gly Ala Ser
145                 150                 155

<210> SEQ ID NO 148
<211> LENGTH: 10
<212> TYPE: PRT
<213> ORGANISM: Artificial
<220> FEATURE:
<223> OTHER INFORMATION: Motif in MYB13 DNA binding domain

<400> SEQUENCE: 148

Arg Lys Gly Pro Trp Thr Glu Gln Glu Asp
1               5                   10

<210> SEQ ID NO 149
<211> LENGTH: 6
<212> TYPE: PRT
<213> ORGANISM: Artificial
<220> FEATURE:
<223> OTHER INFORMATION: Motif in MYB13 DNA binding domain

<400> SEQUENCE: 149

Ala Lys Val Ser Gly Leu
1               5

<210> SEQ ID NO 150
<211> LENGTH: 14
<212> TYPE: PRT
<213> ORGANISM: Artificial
<220> FEATURE:
<223> OTHER INFORMATION: Motif in MYB13 DNA binding domain

<400> SEQUENCE: 150

Gly Lys Ser Cys Arg Leu Arg Trp Val Asn Tyr Leu His Pro
1               5                   10

<210> SEQ ID NO 151
<211> LENGTH: 15
<212> TYPE: PRT
<213> ORGANISM: Artificial
<220> FEATURE:
<223> OTHER INFORMATION: Motif in MYB13 DNA binding domain

<400> SEQUENCE: 151

Pro Gly Arg Thr Asp Asn Glu Ile Lys Asn Tyr Trp Arg Thr His
1               5                   10                  15

<210> SEQ ID NO 152
<211> LENGTH: 7
<212> TYPE: PRT
<213> ORGANISM: Artificial
<220> FEATURE:
<223> OTHER INFORMATION: Motif in wheat and barley MYB13 polypeptides

<400> SEQUENCE: 152

Ser Thr Thr Thr Ser Thr Ser
```

```
<210> SEQ ID NO 153
<211> LENGTH: 8
<212> TYPE: PRT
<213> ORGANISM: Artificial
<220> FEATURE:
<223> OTHER INFORMATION: Motif in wheat and barley MYB13 polypeptides

<400> SEQUENCE: 153

Ser Thr Thr Thr Thr Ser Thr Ser
1               5

<210> SEQ ID NO 154
<211> LENGTH: 9
<212> TYPE: PRT
<213> ORGANISM: Artificial
<220> FEATURE:
<223> OTHER INFORMATION: Motif in wheat and barley MYB13 polypeptides

<400> SEQUENCE: 154

Thr Thr Ser Ser Ser Ser Ser Ser Thr
1               5

<210> SEQ ID NO 155
<211> LENGTH: 6
<212> TYPE: PRT
<213> ORGANISM: Artificial
<220> FEATURE:
<223> OTHER INFORMATION: Motif in wheat and barley MYB13 polypeptides

<400> SEQUENCE: 155

Pro Pro Pro Ser Ser Pro
1               5

<210> SEQ ID NO 156
<211> LENGTH: 27
<212> TYPE: DNA
<213> ORGANISM: Artificial
<220> FEATURE:
<223> OTHER INFORMATION: Variant MYB13 binding site

<400> SEQUENCE: 156
tcccgtggga atttggtaga tattctt                                          27

<210> SEQ ID NO 157
<211> LENGTH: 27
<212> TYPE: DNA
<213> ORGANISM: Artificial
<220> FEATURE:
<223> OTHER INFORMATION: Variant MYB13 binding site

<400> SEQUENCE: 157
tatagctggg gtttggtggt aaagatg                                          27

<210> SEQ ID NO 158
<211> LENGTH: 27
<212> TYPE: DNA
<213> ORGANISM: Artificial
<220> FEATURE:
<223> OTHER INFORMATION: Variant MYB13 binding site

<400> SEQUENCE: 158
ctgtgctctt tttcggtagc gtagtgt                                          27

<210> SEQ ID NO 159
```

```
<211> LENGTH: 27
<212> TYPE: DNA
<213> ORGANISM: Artificial
<220> FEATURE:
<223> OTHER INFORMATION: Variant MYB13 binding site

<400> SEQUENCE: 159
agttgaagag ttttggtaaa tcaccgc                                          27

<210> SEQ ID NO 160
<211> LENGTH: 27
<212> TYPE: DNA
<213> ORGANISM: Artificial
<220> FEATURE:
<223> OTHER INFORMATION: Variant MYB13 binding site

<400> SEQUENCE: 160
agttgaagag ttttggtaaa tcaccac                                          27

<210> SEQ ID NO 161
<211> LENGTH: 27
<212> TYPE: DNA
<213> ORGANISM: Artificial
<220> FEATURE:
<223> OTHER INFORMATION: Variant MYB13 binding site

<400> SEQUENCE: 161
gttgaagtag ttttggtaaa tcaccac                                          27

<210> SEQ ID NO 162
<211> LENGTH: 27
<212> TYPE: DNA
<213> ORGANISM: Artificial
<220> FEATURE:
<223> OTHER INFORMATION: Variant MYB13 binding site

<400> SEQUENCE: 162
tcctcacatg gttaggtttt ttgtggt                                          27

<210> SEQ ID NO 163
<211> LENGTH: 27
<212> TYPE: DNA
<213> ORGANISM: Artificial
<220> FEATURE:
<223> OTHER INFORMATION: Variant MYB13 binding site

<400> SEQUENCE: 163
tccaataaag ttttggtaag ttttgct                                          27

<210> SEQ ID NO 164
<211> LENGTH: 27
<212> TYPE: DNA
<213> ORGANISM: Artificial
<220> FEATURE:
<223> OTHER INFORMATION: Variant MYB13 binding site

<400> SEQUENCE: 164
ggatccagcc gttcggtgat gcttggc                                          27

<210> SEQ ID NO 165
<211> LENGTH: 435
<212> TYPE: PRT
<213> ORGANISM: Triticum aestivum

<400> SEQUENCE: 165

Met Ala Thr Ala Ser Pro Arg Leu Leu Pro Leu Ala Leu Leu Leu Leu
```

-continued

```
1               5                   10                  15
Leu Leu Ala Val Ala His Ala Gly Thr Pro Arg Leu Val Leu Glu Pro
                20                  25                  30
Thr Leu Arg Leu Pro Ser Gln Arg Ala Ala Gly Gln Gly Asp Asp
                35                  40                  45
Gly Ser Val Gly Thr Arg Trp Ala Val Leu Val Ala Gly Ser Asn Gly
50                      55                  60
Tyr Gln Asn Tyr Arg His Gln Ala Asp Ile Cys His Ala Tyr Gln Ile
65                      70                  75                  80
Leu Lys Lys Gly Gly Leu Lys Asp Glu Asn Ile Ile Val Phe Met Tyr
                85                  90                  95
Asp Asp Ile Ala His Asn Arg Glu Asn Pro Arg Pro Gly Val Ile Ile
                100                 105                 110
Asn His Pro Gln Gly Gly Asp Val Tyr Ala Gly Val Pro Lys Asp Tyr
                115                 120                 125
Thr Gly Lys Glu Val Asn Val Lys Asn Leu Phe Ala Val Leu Leu Gly
                130                 135                 140
Asn Lys Thr Ala Val Ser Gly Gly Ser Gly Lys Val Val Asp Ser Gly
145                 150                 155                 160
Pro Asn Asp His Ile Phe Val Phe Tyr Ser Asp His Gly Gly Pro Gly
                165                 170                 175
Val Ile Gly Met Pro Thr Asn Pro Tyr Val Tyr Gly Asp Asp Leu Val
                180                 185                 190
Asp Val Leu Lys Lys Ser Met Leu Leu Gly Ser Tyr Lys Ala Trp Tyr
                195                 200                 205
Pro Ile Val Leu Cys Tyr Phe Ala Leu His Gly Leu Leu Leu Glu Ala
                210                 215                 220
Met Val Phe Tyr Leu Glu Ala Cys Glu Ala Gly Ser Val Phe Glu Gly
225                 230                 235                 240
Leu Leu Pro Asn Asp Ile Gly Val Tyr Ala Thr Thr Ala Ser Asp Ala
                245                 250                 255
Glu Glu Ser Ser Trp Glu Arg Ile Ala Leu Ala Ser Thr Pro Ala Leu
                260                 265                 270
Arg Arg Asn Met Thr Pro Ala Trp Ala Thr Cys Thr Ala Phe Leu Gly
                275                 280                 285
Trp Lys Thr Ala Val Asn Gln Arg Asp Ala Asp Leu Val Tyr Phe Trp
                290                 295                 300
His Lys Tyr Arg Lys Leu Ala Glu Ser Ser Pro Glu Lys Asn Asp Ala
305                 310                 315                 320
Arg Lys Gln Leu Leu Glu Met Thr Ser His Arg Ser His Ile Asp Asn
                325                 330                 335
Ser Val Glu Leu Ile Gly Asn Leu Leu Phe Gly Phe Ala Asp Gly Pro
                340                 345                 350
Met Val Leu Lys Thr Val Arg Pro Ala Gly Glu Pro Leu Val Asp Asp
                355                 360                 365
Trp Ser Cys Leu Lys Ser Thr Val Arg Ala Phe Glu Ser Gln Cys Gly
                370                 375                 380
Ser Leu Ala Gln Tyr Gly Met Lys His Met Arg Ser Phe Ala Asn Ile
385                 390                 395                 400
Cys Asn Ala Gly Val Leu Pro Glu Ala Met Val Lys Val Ala Ala Gln
                405                 410                 415
Ala Cys Lys Ser Ile Pro Thr Asn Pro Trp Ser Ala Thr His Lys Gly
                420                 425                 430
```

Phe Ser Ala
    435

<210> SEQ ID NO 166
<211> LENGTH: 1308
<212> TYPE: DNA
<213> ORGANISM: Triticum aestivum

<400> SEQUENCE: 166

```
atggcgacgg cgtcaccccg cctccttccg ctcgcgctgc tgctcctcct gctcgccgtg      60
gcgcacgccg gcaccccacg gctggtcctg gagcccaccc ttcggctgcc gtcgcagcgc     120
gcggcggccg ggcaggggga cgatggctcc gtcgggacca ggtgggccgt cctcgtcgcc     180
ggctccaacg gctaccagaa ctaccgccac caggcagata tttgccacgc ctaccagatc     240
ttgaagaagg gtggtctcaa ggatgagaac atcattgtct tcatgtacga cgatattgcg     300
cacaaccggg agaacccaag gccgggcgtc atcatcaacc accccaaggt tggagatgtc     360
tatgctgggg tccctaagga ctacactggg aaggaggtta atgtcaagaa cttgtttgct     420
gtcctgctcg gtaataaaac cgctgtgagt ggtgggagtg gcaaagtcgt ggacagtggt     480
cctaatgatc acattttgt gttttacagt gaccatgggg tcctggggt cattgggatg     540
cccaccaatc catacgttta cggtgacgat cttgtagatg tcctgaagaa agcatgctg     600
ctaggaagct acaaagcctg gtaccccatc gtcctttgtt attttgctct gcatggtttg     660
ctgcttgaag caatggtatt ttaccttgaa gcctgtgaag ccgggagtgt cttcgagggg     720
cttctgccga tgacatcgg tgtctacgcg accaccgcgt cggacgcgga ggagagcagt     780
tgggaacgta ttgccctggc gagtacccca gccctccgcc ggaatatgac acctgcttgg     840
gcgacctgta cagcatttct tggatggaag acagctgtta atcagaggga tgctgatctt     900
gtttacttct ggcacaagta ccggaaattg gctgagagtt cccctgagaa aaacgatgcc     960
cggaagcaat gctcgaaat gacgagtcat agatcgcata tcgacaatag cgtcgagctg    1020
attggaaaacc ttctgtttgg ttttgcggat ggtccaatgg ttctaaagac tgttcgccca    1080
gccggtgagc tcttgttga tgactggagt tgtctcaagt ctacggtgcg tgcttttgaa    1140
tcacaatgtg gctcgctggc acagtatgga atgaaacaca tgcggtcctt tgcaaacatc    1200
tgcaatgccg cgctccttcc tgaagcgatg gtgaaggtcg ctgctcaggc atgcaagagc    1260
atcccaacca acccctggag tgccacacac aagggtttta gtgcttaa                 1308
```

<210> SEQ ID NO 167
<211> LENGTH: 323
<212> TYPE: PRT
<213> ORGANISM: Triticum aestivum

<400> SEQUENCE: 167

Met Ala Ala Lys Arg Glu Leu Val Val Ser Phe Gly Glu Met Leu Ile
1               5                   10                  15

Asp Phe Val Pro Thr Val Ala Gly Val Ser Leu Ala Glu Ala Pro Ala
            20                  25                  30

Phe Val Lys Ala Pro Gly Gly Ala Pro Ala Asn Val Ala Ile Ala Val
        35                  40                  45

Ala Arg Leu Gly Gly Gly Ala Ala Phe Val Gly Lys Leu Gly Asp Asp
    50                  55                  60

Glu Phe Gly Arg Met Leu Ala Lys Ile Leu Arg Asp Asn Gly Val Asp
65                  70                  75                  80

```
Ala Gly Gly Val Val Phe Asp Ser Gly Ala Arg Thr Ala Leu Ala Phe
                85                  90                  95

Val Thr Leu Arg Ala Asp Gly Glu Arg Glu Phe Met Phe Tyr Arg Asn
            100                 105                 110

Pro Ser Ala Asp Met Leu Leu Thr Ala Asp Glu Leu Lys Val Asp Val
            115                 120                 125

Ile Lys Arg Ala Ala Val Phe His Tyr Gly Ser Ile Ser Leu Ile Ala
            130                 135                 140

Glu Pro Cys Arg Thr Ala His Leu His Ala Met Lys Val Ala Lys Glu
145                 150                 155                 160

Ala Gly Ala Leu Leu Ser Tyr Asp Pro Asn Leu Arg Glu Ala Leu Trp
                165                 170                 175

Pro Ser Leu Glu Glu Ala Arg Thr Lys Ile Leu Ser Ile Trp Asp Gln
            180                 185                 190

Ala Asp Ile Val Lys Val Ser Glu Val Glu Leu Glu Phe Leu Thr Gly
            195                 200                 205

Ile Asn Ser Val Glu Asp Asp Val Ala Met Lys Leu Trp Arg Pro Thr
            210                 215                 220

Phe Lys Leu Met Leu Ile Thr Leu Gly Asp Gln Gly Cys Lys Tyr Tyr
225                 230                 235                 240

Thr Lys Asp Phe Arg Gly Ala Val Pro Ser Tyr Lys Val Gln Gln Val
            245                 250                 255

Asp Thr Thr Gly Ala Gly Asp Ala Phe Ile Gly Ser Leu Leu Arg Lys
            260                 265                 270

Ile Val Gln Asp Pro Ser Ala Leu Gln Asp Lys Thr Lys Leu Glu Gly
            275                 280                 285

Ala Ile Lys Leu Val His Ala Cys Gly Ala Ile Thr Ala Thr Lys Lys
            290                 295                 300

Gly Ala Ile Pro Ser Leu Pro Lys Glu Asp Glu Val Leu Arg Leu Met
305                 310                 315                 320

Glu Lys Ala

<210> SEQ ID NO 168
<211> LENGTH: 972
<212> TYPE: DNA
<213> ORGANISM: Triticum aestivum

<400> SEQUENCE: 168
atggcggcaa agcgcgagct ggtggtcagc ttcggggaga tgctgataga cttcgtgccg      60
acggtggccg gggtgtcgct ggcggaggcg ccggccttcg tcaaggcgcc cggggggcgcc    120 ccggccaacg tcgccatcgc cgtcgcgcgc ctcggcggcg gggccgcctt cgtcggcaag    180
ctcggcgacg acgagttcgg ccgcatgctc gccaaaatcc tccgcgacaa cggcgtcgac    240
gccggcggcg tcgtcttcga ctcgggcgcg cgcaccgcgc tcgccttcgt cacgctccgc    300
gccgacgggg agcgcgagtt catgttctac cgcaaccccca gcgccgacat gctcctcacc    360
gccgacgagc tcaaggtcga cgtcatcaag agggctgcag tcttccacta tggatcaata    420
agcttgattg ccgagccttg ccggacagcg catctgcacg ccatgaaggt tgccaaagag    480 gccgcgcgc ttctctcgta tgacccgaac ctgagggagg cattgtggcc atcccttgag    540
gaggctcgca ccaagatctt gagcatctgg gaccaggcag acattgtcaa ggtcagcgag    600
gtcgagctcg agttttttgac tggcatcaac tcggtggagg acgatgtcgc catgaagctg    660
tggcgcccta cctttaagct catgcttatc actcttggag atcaaggatg caagtactat    720
```

```
accaaggatt tccgtggagc tgtcccatcc tacaaggtac agcaagtcga tacgacaggt      780
gctggtgatg catttattgg ttctctgctc cgaaaaattg tccaggatcc atcggcattg      840
caagataaga caaagcttga gggggcgatc aaattagtcc atgcatgtgg agcaatcacc      900
gccacgaaga aaggggcaat cccttcgttg cccaaggaag acgaggtgtt gcggctgatg      960
gagaaggcgt ag                                                           972
```

METHODS OF CONTROLLING FRUCTAN SYNTHESIS IN PLANTS

CROSS-REFERENCE TO RELATED APPLICATIONS

This application is a §371 national stage of PCT International Application No. PCT/AU2012/000942, filed Aug. 10, 2012, claiming the benefit of U.S. Provisional Application No. 61/523,050, filed Aug. 12, 2011, the contents of each of which are hereby incorporated by reference in their entirety.

REFERENCE TO SEQUENCE LISTING

This application incorporates-by-reference nucleotide and/or amino acid sequences which are present in the file named "14 1031 2251_83212_A_PCT_US_Substitute_Sequence_Listing_JR.txt," which is 80.7 kilobytes in size, and which was created Oct. 30, 2014 in the IBM-PC machine format, having an operating system compatibility with MS-Windows, which is contained in the text file filed Oct. 31, 2014 as part of this application.

FIELD OF THE INVENTION

The present invention relates to plants with increased levels of water soluble carbohydrates, particularly fructan, in the stem and leaf sheath. The present invention also provides methods of identifying and/or producing these plants. In particular, the present invention relates to a novel class of polypeptides designated MYB13 which upregulate the expression of enzymes involved in fructan synthesis. The present invention further relates to a novel promoter element that can be used to express genes predominantly in the stem and leaf sheath during the early reproductive stage of a plant.

BACKGROUND OF THE INVENTION

Temperate cereals such as wheat and barley deposit temporary carbon reserves in the stem and leaf sheath at the early reproductive stage in the form of water soluble carbohydrates (WSC). WSC in wheat stem is composed of fructans, sucrose and hexoses with fructans being the major component at anthesis (Xue et al., 2008b; Ruuska et al., 2006, 2008) and is an important reserve carbon source for grain yield (Bonnett and Incoll, 1992; Schnyder, 1993). WSC can accumulate in wheat stems to more than 40% of total stem dry weight (Housley, 2000). WSC mobilises from the stem during the later phase of grain filling and can potentially contribute to about 20% of grain yield under normal conditions (Wardlaw and Willenbrink, 2000). The stem WSC becomes more important for grain yield in cereal crops in drought and heat-prone environments (van Herwaarden et al., 1998; Wardlaw and Willenbrink, 2000; Barnabas et al., 2008). Variation in stem WSC concentrations among wheat genotypes is one of the genetic factors influencing grain weight and yield in drought- and heat-prone environments in Northern Australia (Xue et al., 2008b).

Fructans are soluble linear or branched β-2,1- or β-2,6-linked fructosyl-oligosaccharides and are recognised as one of the major forms of carbon reserve in about 15% of higher plant species (Hendry, 1993; Vijn and Smeekens, 1999; Van Laere and Van den Ende, 2002; Van den Ende et al., 2011). Fructans deposited in the stem and leaf sheath of temperate cereals act as short-term carbon reserve, while fructan accumulation in some dicots and perennial grasses for longer term storage (Valluru and Van den Ende, 2008). Although the primary role of fructans in plants is to bridge gaps between the excess and deficit of photosynthetic carbon relative to the carbon demand, fructans are also used for osmoregulation during flower opening (Le Roy et al., 2007), protection of plants from drought and cold stresses through membrane stabilisation (Valluru and Van den Ende, 2008; Kawakami et al., 2008; Livingston et al., 2009; Van den Ende and Valluru, 2009) and serve as antioxidant (Van den Ende and Valluru 2009; Bolouri-Moghaddam et al., 2010).

Fructans are synthesised from sucrose in vacuoles of cells by a group of fructosyltransferses belonging to plant glycoside hydrolase family 32 enzymes (Ritsema and Smeekens, 2003; Chalmers et al., 2005; Altenbach et al., 2009; Van den Ende et al., 2009). Fructans in cereals are mainly of the graminan type, that is predominantly β-2,6-linked fructosyl-units with short β-2,1-linked branches (Ritsema and Smeekens, 2003; Chalmers et al., 2005). The β-2,6-linked fructan is synthesized by the consecutive action of sucrose:sucrose 1-fructosyltransferase (1-SST) and sucrose:fructan 6-fructosyltransferase (6-SFT). The enzyme responsible for the synthesis of β-2,1-linked branchs in graminan is fructan:fructan 1-fructosyltransferase (1-FFT) (Kawakami and Yoshida, 2005).

1-SST, 6-SET and 1-FFT cDNAs from wheat have been characterised (Kawakami and Yoshida, 2002, 2005). The enzyme 6G-FFT, which couples fructosyl residues to either the terminal glucose via a β-2,6-linkage or a terminal fructose via a β-2,1-linkage (Ritsema et al., 2003, 2005), is known to be absent in barley (Lasseur et al., 2011). The structure of cereal fructans suggests that 1-SST and 6-SFT are the more important enzymes involved in fructan synthesis in cereals. This appears to be reflected by the relative mRNA abundance of 1-SST, 6-SFT and 1-FFT genes in wheat stems. The Affymetrix array hybridisation signals of 1-SST and 6-SFT transcripts in wheat stems at anthesis are about 5-50 times higher than that of 1-FFT (Xue et al., 2008b).

Fructan synthesis in plants is known to be regulated by metabolic signals such as the concentration of sugars, particularly sucrose, and developmental stimuli (Blacklow et al., 1984; Müller et al., 2000; Maleux and Van den Ende, 2007; Ruuska et al., 2008; Kusch et al., 2009), as well as environmental factors such as drought and low temperature (De Roover et al., 2000; Wei and Chatterton 2001; Hisano et al., 2008; del Viso et al., 2009; Rao et al., 2011). Several studies have indicated that expression of fructosyltransferase genes in cereals is regulated by sucrose and stem developmental signals (Müller et al., 2000; Martinez-Noel et al., 2001; Koroleva et al., 2001; Nagaraj et al., 2001, 2004; Lu et al., 2002; Martinez-Noel et al., 2006; Ruuska et al., 2008). It appears that up-regulation of fructosyltransferase genes by sucrose coupled with their up-regulation at the early reproductive stage and down-regulation at the mid grain filling stage provides fine tuning in the regulation of fructan accumulation in temperate cereals. As a result, excess sucrose can be deposited as a temporary carbon reserve at the early reproductive stage when the photosynthesis capacity of the plant exceeds its carbon demand. The stored fructan mobilises through the action of fructan exohydrolases (Van den Ende et al., 2003, 2005; Kawakami et al., 2005; Van Riet et al., 2006) when the sink (grain) demand for carbon is higher than its photosynthesis capacity at the mid and late grain filling stage.

To understand how fructosyltransferases are regulated, recent studies have identified some molecular components in sucrose-mediated induction of fructan synthesis in plants such as phosphatase type 2A, protein kinases, small GTPases and phosphatidylinositol 3-kinase (Martinez-Noel et al., 2001, 2006, 2007, 2009, 2010; Kusch et al., 2009; Ritsema et al., 2009). These signalling molecules are required for the up-regulation of fructosyltransferase genes by sucrose (Ritsema et al., 2009). To further dissect the molecular basis of the high WSC trait, a genome-wide expression analysis was performed using Affymetrix wheat genome array in the stems of recombinant inbred Serix Babax (SB) lines of wheat (*T. aestivum* L.) varying in stem WSC concentrations. These studies showed that the mRNA and enzyme levels of 1-SST and 6-SFT in wheat stems at anthesis are positively correlated with WSC and fructan concentrations among SB lines (Xue et al., 2008b).

Trans-acting factors involved in sucrose or developmental regulation of fructan synthesis are still unknown. Elucidation of trans-acting factors and gene regulatory networks controlling fructan accumulation is important to develop methods of identifying and producing plants with improved levels of fructan.

SUMMARY OF THE INVENTION

The present inventors have identified a new subfamily of MYB polypeptides. This new subfamily of MYB polypeptides, designated herein MYB13 polypeptides, can be used, inter alia, to enhance fructan levels in transgenic plants.

In a first aspect, the present invention provides a transgenic plant comprising an exogenous polynucleotide encoding a MYB13 polypeptide, wherein the polynucleotide is operably linked to a promoter capable of directing expression of the polynucleotide in a cell of the plant.

In an embodiment, the MYB13 polypeptide comprises a MYB DNA binding domain which comprises one or more, preferably all four, of the following motifs;

|      |              | (SEQ ID NO: 148) |
| ---- | ------------ | ---------------- |
| i)   | RKGPWTEQED,  |                  |

|      |        | (SEQ ID NO: 149) |
| ---- | ------ | ---------------- |
| ii)  | AKVSGL,|                  |

|       |                  | (SEQ ID NO: 150) |
| ----- | ---------------- | ---------------- |
| iii)  | GKSCRLRWVNYLHP,  |                  |
| and   |                  |                  |

|      |                   | (SEQ ID NO: 151) |
| ---- | ----------------- | ---------------- |
| iv)  | PGRTDNEIKNYWRTH.  |                  |

In a further embodiment, the MYB13 polypeptide comprises amino acids having a sequence as provided in any one of SEQ ID NOs: 1 to 4, 13 to 17 or 143 to 147, a biologically active fragment thereof, or an amino acid sequence which is at least 30%, more preferably at least 50%, more preferably at least 75%, more preferably at least 90%, more preferably at least 95%, and even more preferably at least 97%, identical to any one or more of SEQ ID NOs: 1 to 4, 13 to 17 or 143 to 147. More preferably, the MYB13 polypeptide comprises amino acids having a sequence as provided in any one of SEQ ID NOs: 1 to 4, a biologically active fragment thereof, or an amino acid sequence which is at least 30%, more preferably at least 50%, more preferably at least 75%, more preferably at least 90%, more preferably at least 95%, and even more preferably at least 97%, identical to any one or more of SEQ ID NOs: 1 to 4.

In another embodiment, the MYB13 polypeptide comprises a MYB DNA binding domain which comprises amino acids having a sequence as provided as amino acids about 27 to about 130 of SEQ ID NO: 1, a biologically active fragment thereof, or an amino acid sequence which is at least 70%, more preferably at least 75%, more preferably at least 80%, more preferably at least 90%, more preferably at least 95%, and even more preferably at least 97%, identical to amino acids about 27 to about 130 of SEQ ID NO: 1.

In another embodiment, the MYB13 polypeptide comprises a MYB DNA binding domain which comprises amino acids having a sequence as provided in any one of SEQ ID NOs: 18 to 24, a biologically active fragment thereof, or an amino acid sequence which is at least 70%, more preferably at least 75%, more preferably at least 80%, more preferably at least 90%, more preferably at least 95%, and even more preferably at least 97%, identical to any one or more of SEQ ID NOs: 18 to 24.

In another embodiment, the MYB13 polypeptide comprises a domain which comprises amino acids having a sequence as provided as amino acids 131 to 260 of SEQ ID NO: 1, a biologically active fragment thereof, or an amino acid sequence which is at least 30%, more preferably at least 50%, more preferably at least 75%, more preferably at least 90%, more preferably at least 95%, and even more preferably at least 97%, identical to amino acids 131 to 260 of SEQ ID NO: 1.

In a further embodiment, the MYB13 polypeptide binds a promoter element comprising a sequence provided as one or more of SEQ ID NOs 45, 73 and 74. More preferably, the promoter element is present in a plant gene encoding one or more of sucrose:sucrose 1-fructosyltransferase (1-SST), sucrose:fructan 6-fructosyltransferase (6-SFT), fructan:fructan 1-fructosyltransferase (1-FFT), γ-vacuolar processing enzyme (γ-VPE) or fructokinase 1 (FK1).

In yet another embodiment, the transgenic plant has, preferably when grown under stress conditions such as water-stressed conditions at least some point during flowering and/or anthesis,
  i) an enhanced level of fructan in the stem and/or leaf sheath when compared to an isogenic plant lacking the exogenous polynucleotide,
  ii) an increased level of one or more of sucrose:sucrose 1-fructosyltransferase (1-SST) activity, sucrose:fructan 6-fructosyltransferase (6-SFT) activity, fructan:fructan 1-fructosyltransferase (1-FFT) activity, γ-vacuolar processing enzyme (γ-VPE) activity or fructokinase 1 (FK1) activity in the stem and/or leaf sheath when compared to an isogenic plant lacking the exogenous polynucleotide,
  iii) an increased level of expression in the stem and/or leaf sheath of an endogenous gene(s) encoding one or more of 1-SST, 6-SFT, 1-FFT γ-VPE and FK1 when compared to an isogenic plant lacking the exogenous polynucleotide,
  iv) a higher grain yield and/or average grain size when compared to an isogenic plant lacking the exogenous polynucleotide,
  v) an increased level of fructan in the seed of the plant when compared to seed from an isogenic plant lacking the exogenous polynucleotide,
  vi) more tolerance to stress conditions than an isogenic plant lacking the exogenous polynucleotide, or
  vii) a combination of two or more of the features of i) to vi).

Examples of stress conditions include, but are not limited to, water stress, heat stress, cold stress, salt stress, disease, or a combination of two or more thereof. Preferably, the stress conditions are water stress and/or heat stress.

In a preferred embodiment, the plant is a cereal plant such as, but not limited to, wheat, rye, oats or barley.

Examples of suitable promoters include one or more of, but not limited to, a sucrose-responsive promoter, a promoter that is expressed in stems and/or leaf sheath at least some point during flowering and/or anthesis, or a promoter that is preferentially expressed in the seed and/or the endosperm.

Preferably, the transgenic plant is homozygous for the exogenous polynucleotide.

Preferably, the transgenic plant is growing in a field.

Also provided is a population of at least 100 plants of the invention growing in a field.

In a further aspect, the present invention provides a chimeric vector comprising a polynucleotide comprising nucleotides having
  i) a sequence as provided in any one of SEQ ID NOs: 5 to 8,
  ii) a sequence which is at least 30% identical to any one or more of SEQ ID NOs: 5 to 8, or
  iii) a sequence which hybridizes to i) and/or ii) under stringent conditions, wherein the polynucleotide is operably linked to a promoter capable of directing expression of the polynucleotide in a cell.

In a preferred embodiment, the cell is a stem or leaf sheath plant cell.

Preferably, the polynucleotide encodes a MYB13 polypeptide. In an embodiment, the polynucleotide comprises a sequence encoding a MYB13 polypeptide as defined herein such as, but not limited to, a MYB13 polypeptide comprising amino acids having a sequence as provided in any one of SEQ ID NOs: 1 to 4, 13 to 17 or 143 to 147.

In yet a further aspect, the present invention provides a recombinant cell comprising an exogenous polynucleotide comprising nucleotides having
  i) a sequence as provided in any one of SEQ ID NOs: 5 to 8,
  ii) a sequence which is at least 30% identical to any one or more of SEQ ID NOs: 5 to 8, or
  iii) a sequence which hybridizes to i) and/or ii) under stringent conditions, wherein the polynucleotide is operably linked to a promoter capable of directing expression of the polynucleotide in the cell.

The cell of the above two aspects can be any cell such as, but not limited to, a yeast cell, bacterial cell or a plant cell. Preferably, the cell is a plant cell. More preferably, a plant stem or leaf sheath cell.

In a further aspect, the present invention provides a method of producing a transgenic plant of the invention, the method comprising the steps of
  i) introducing a polynucleotide having
    a) a sequence as provided in any one of SEQ ID NOs: 5 to 8,
    b) a sequence which is at least 30% identical to any one or more of SEQ ID NOs: 5 to 8, or
    c) a sequence which hybridizes to a) and/or b) under stringent conditions, and/or a vector comprising said polynucleotide into a cell of a plant,
  ii) regenerating a transgenic plant from the cell, and
  iii) optionally harvesting seed from the plant, and/or
  iv) optionally producing one or more progeny plants from the transgenic plant, thereby producing the transgenic plant.

In another aspect, the present invention provides a method of producing a transgenic plant of the invention, the method comprising the steps of
  i) crossing two parental plants, wherein at least one is a transgenic plant of the invention,
  ii) screening one or more progeny plants from the cross for the presence or absence of the exogenous polynucleotide, and
  iii) selecting a progeny plant which comprise the exogenous polynucleotide, thereby producing the transgenic plant.

Preferably, step iii) comprises selecting progeny plants which are homozygous for the exogenous polynucleotide.

Preferably, step iii) comprises analysing the phenotype of the plant or one or more progeny plants thereof for at least one of the features defined herein such as fructan levels, 1-SST levels, 6-SFT levels, FFT-1 levels, γ-VPE levels, FK1 levels, grain yield and average grain size.

In an embodiment, the method further comprises the step of analysing the plant for at least one other genetic marker.

Also provided is a transgenic plant produced using the method of the invention.

In a further aspect, the present invention provides for the use of a polynucleotide having
  i) a sequence as provided in any one of SEQ ID NOs: 5 to 8,
  ii) a sequence which is at least 30% identical to any one or more of SEQ ID NOs: 5 to 8, or
  iii) a sequence which hybridizes to i) and/or ii) under stringent conditions, and/or a vector comprising said polynucleotide, to produce a recombinant cell and/or a transgenic plant.

In yet further aspect, the present invention provides a method for identifying a transgenic plant of the invention, the method comprising the steps of
  i) obtaining a nucleic acid sample from a plant, and
  ii) screening the sample for the presence or absence of the exogenous polynucleotide,
wherein presence of the exogenous polynucleotide indicates that the plant is a transgenic plant of the invention.

In an embodiment, the method further comprises growing the plant, preferably under stress conditions, and analysing the phenotype of the plant, preferably for at least one of the features defined herein such as fructan levels, 1-SST levels, 6-SFT levels, 1-FFT levels, γ-VPE levels, FK1 levels, grain yield and average grain size.

In another embodiment, the method further comprises producing a plant from a seed before step i).

In another aspect, the present invention provides a method of enhancing or maintaining the yield of seed from a crop of plants, the method comprising
  i) growing in a field a crop of transgenic plants of the invention, and/or a population of the invention,
  ii) harvesting seed from the plants, and
  iii) optionally processing the seed into a product which is not capable of germinating.

Preferably, the crop and/or plant is grown under stress conditions and/or there is the possibility the crop and/or plant will be exposed to stress conditions.

The present inventors have also identified a new promoter element which is bound by a MYB polypeptide.

Thus, in a further aspect the present invention provides a transgenic plant comprising an exogenous polynucleotide comprising nucleotides having a sequence provided as one or more of SEQ ID NOs 45, 73 and 74, wherein the polynucleotide is operably linked to a gene of interest.

In an embodiment, the exogenous polynucleotide comprises at least two copies of the defined sequence. In another embodiment, the exogenous polynucleotide comprises one, two or three copies of the defined sequence.

Preferably, the polynucleotide can be bound by a MYB13 polypeptide.

The gene of interest can be any gene such as, but not limited to, a gene encoding a protein involved in water soluble carbohydrate synthesis such as a 1-SST gene or 6-SFT gene.

Also provided is a population of at least 100 plants of the invention growing in a field.

In another aspect, the present invention provides a chimeric vector comprising a polynucleotide comprising nucleotides having a sequence provided as one or more of SEQ ID NOs 45, 73 and 74, wherein the polynucleotide is operably linked to a gene of interest.

In a further aspect, the present invention provides a recombinant cell comprising an exogenous polynucleotide comprising nucleotides having a sequence provided as one or more of SEQ ID NOs 45, 73 and 74, wherein the polynucleotide is operably linked to a gene of interest.

The cell can be any cell such as, but not limited to, a yeast cell, bacterial cell or a plant cell. Preferably, the cell is a plant cell. More preferably, a plant stem or leaf sheath cell.

In a further aspect, the present invention provides a method of producing a transgenic plant of the invention, the method comprising the steps of
  i) introducing a polynucleotide having a sequence provided as one or more of SEQ ID NOs 45, 73 and 74, wherein the polynucleotide is operably linked to a gene of interest, and/or a vector comprising said polynucleotide, into a cell of a plant,
  ii) regenerating a transgenic plant from the cell, and
  iii) optionally harvesting seed from the plant, and/or
  iv) optionally producing one or more progeny from the transgenic plant, thereby producing the transgenic plant.

In another aspect, the present invention provides a method of producing a transgenic plant of the invention, the method comprising the steps of
  i) crossing two parental plants, wherein at least one is a transgenic plant of the invention,
  ii) screening one or more progeny plants from the cross for the presence or absence of the exogenous polynucleotide, and
  iii) selecting a progeny plant which comprise the exogenous polynucleotide, thereby producing the transgenic plant.

Also provided is a transgenic plant produced using the method of the invention.

Also provided is the use of a polynucleotide having a sequence provided as one or more of SEQ ID NOs 45, 73 and 74, or a vector comprising said polynucleotide, to produce a recombinant cell and/or a transgenic plant.

In a further aspect, the present invention provides a method for identifying a transgenic plant of the invention; the method comprising the steps of
  i) obtaining a nucleic acid sample from a plant, and
  ii) screening the sample for the presence or absence of the exogenous polynucleotide,
wherein presence of the exogenous polynucleotide indicates that the plant is a transgenic plant of the invention.

In another aspect, the present invention provides a plant part of a plant of the invention.

In a preferred embodiment, the plant part is a seed that comprises the exogenous polynucleotide.

In a further embodiment, the seed is unable to germinate. For instance, the seed has been polished or heat treated.

In a further aspect, the present invention provides a method of producing a plant part, the method comprising,
  a) growing a plant of the invention,
  b) harvesting the plant part, and
  c) optionally wherein the plant part is a seed, processing the seed into a product which is not capable of germinating.

In an embodiment, at least some stage of step a) is performed under stress conditions.

In an embodiment, the plant part is seed.

In another aspect, the present invention provides a method of producing flour, wholemeal, starch or other product obtained from seed, the method comprising;
  a) obtaining the seed of the invention, and
  b) processing the seed to produce the flour, wholemeal, starch or other product.

Also provided is a product produced from a plant of the invention, or part thereof. Preferably, the part is a seed.

In one embodiment, the product is a food product or beverage product. Examples of food products include, but are not limited to, flour, starch, leavened or unleavened breads, pasta, noodles, animal fodder, breakfast cereals, snack foods, cakes, malt, beer, pastries and foods containing flour-based sauces. Examples of beverage products include, but are not limited to, beer or malt.

In another embodiment, the product is a non-food product. Examples of non-food products include, but are not limited to, films, coatings, adhesives, building materials and packaging materials.

In an embodiment, the product is fructan.

In a further aspect the present invention provides a method of preparing a food product of the invention, the method comprising mixing seed, or flour, wholemeal or starch from the seed, with another food ingredient.

In yet another aspect, the present invention provides a method of preparing malt, comprising the step of germinating seed of the invention.

Also provided is the use of a transgenic plant of the invention, or part thereof, as animal feed, or to produce feed for animal consumption or food for human consumption.

In a further aspect, the present invention provides a method of identifying from a population of plants a plant which has, preferably when grown under stress conditions such as water-stressed conditions at least some point during flowering and/or anthesis, one or more of the following features when compared to another plant in the population;
  i) an enhanced level of fructan in the stem and/or leaf sheath,
  ii) an increased level of one or more of sucrose:sucrose 1-fructosyltransferase (1-SST) activity, sucrose: fructan 6-fructosyltransferase (6-SFT) activity, fructan: fructan 1-fructosyltransferase (1-FFT) activity, γ-vacuolar processing enzyme (γ-VPE) activity and fructokinase 1 activity (FK1) in the stem and/or leaf sheath,
  iii) an increased level of expression in the stem and/or leaf sheath of an endogenous gene(s) encoding one or more of 1-SST, 6-SFT, 1-FFT, γ-VPE and FK1,
  iv) a higher grain yield and/or average grain size,
  v) an increased level of fructan in the seed, or
  vi) more tolerance to stress conditions,
the method comprising detecting a nucleic acid molecule of the plant, wherein the nucleic acid molecule is linked to, and/or comprises at least a part of, an allele of a gene encoding a MYB13 polypeptide which confers one or more of said features.

In an embodiment, the method comprises:
i) hybridising a second nucleic acid molecule to said nucleic acid molecule which is obtained from said plant,
ii) optionally hybridising at least one other nucleic acid molecule to said nucleic acid molecule which is obtained from said plant; and
iii) detecting a product of said hybridising step(s) or the absence of a product from said hybridising step(s).

In an embodiment, the second nucleic acid molecule is used as a primer to reverse transcribe or replicate at least a portion of the nucleic acid molecule.

In an embodiment, the nucleic acid is detected using a technique selected from the group consisting of: restriction fragment length polymorphism analysis, amplification fragment length polymorphism analysis, microsatellite amplification and/or nucleic acid sequencing.

In another embodiment, the method analyses expression levels of the allele.

In another aspect, the present invention provides a method of obtaining a plant, the method comprising;
i) crossing two plants of the same species of which at least one plant comprises an allele of a gene encoding a MYB13 polypeptide which confers, preferably when grown under stress conditions such as water-stressed conditions at least some point during flowering and/or anthesis, one or more of the following features;
   a) an enhanced level of fructan in the stem and/or leaf sheath when compared to an isogenic plant lacking the allele,
   b) an increased level of one or more of sucrose:sucrose 1-fructosyltransferase (1-SST) activity, sucrose:fructan 6-fructosyltransferase (6-SFT) activity, fructan:fructan 1-fructosyltransferase (1-FFT) activity, γ-vacuolar processing enzyme (γ-VPE) activity and fructokinase 1 (FK1) activity in the stem and/or leaf sheath when compared to an isogenic plant lacking the allele,
   c) an increased level of expression in the stem and/or leaf sheath of an endogenous gene(s) encoding one or more of 1-SST, 6-SFT, 1-FFT, γ-VPE and FK1 when compared to an isogenic plant lacking the allele,
   d) a higher grain yield and/or average grain size when compared to an isogenic plant lacking the allele,
   e) an increased level of fructan in the seed of the plant when compared to seed from an isogenic plant lacking the allele, or
   f) more tolerance to stress conditions than an isogenic plant lacking the allele,
ii) screening progeny plants from the cross for the presence or absence of said allele by the method of the invention,
wherein progeny with said allele have one or more of said features when compared to progeny lacking said allele.

In an embodiment of the two above aspects, the method further comprises the step of selecting a plant with the desired genotype or of analysing the plant for at least one other genetic marker.

In yet a further aspect, the present invention provides a method of introducing an allele of a gene encoding a MYB13 polypeptide into the genome of a plant lacking said allele, the method comprising;
i) crossing a first parent plant with a second parent plant, wherein the second plant comprises an allele of a gene encoding a MYB13 polypeptide confers, preferably when grown under stress conditions such as water-stressed conditions at least some point during flowering and/or anthesis, one or more of the following features;
   a) an enhanced level of fructan in the stem and/or leaf sheath when compared to an isogenic plant lacking the allele,
   b) an increased level of one or more of sucrose:sucrose 1-fructosyltransferase (1-SST) activity, sucrose:fructan 6-fructosyltransferase (6-SFT) activity, fructan:fructan 1-fructosyltransferase (1-FFT) activity, γ-vacuolar processing enzyme (γ-VPE) activity and fructokinase 1 (FK1) activity in the stem and/or leaf sheath when compared to an isogenic plant lacking the allele,
   c) an increased level of expression in the stem and/or leaf sheath of an endogenous gene(s) encoding one or more of 1-SST, 6-SFT, 1-FFT, γ-VPE and FK1 when compared to an isogenic plant lacking the allele,
   d) a higher grain yield and/or average grain size when compared to an isogenic plant lacking the allele,
   e) an increased level of fructan in the seed of the plant when compared to seed from an isogenic plant lacking the allele, or
   f) more tolerance to stress conditions than an isogenic plant lacking the allele, and
ii) backcrossing the progeny of the cross of step i) with plants of the same genotype as the first parent plant for a sufficient number of times to produce a plant with a majority of the genotype of the first parent but comprising said allele,
wherein progeny plants are screened for the presence or absence of said allele by the method of the invention.

In a further aspect, the present invention provides a process for identifying a polynucleotide encoding a MYB13 polypeptide comprising:
i) obtaining a polynucleotide operably linked to a promoter, the polynucleotide encoding a polypeptide comprising amino acids having a sequence as provided in any one of SEQ ID NOs: 1 to 4, 13 to 17 or 143 to 147, a biologically active fragment thereof, or an amino acid sequence which is at least 30% identical to any one or more of SEQ ID NOs: 1 to 4, 13 to 17 or 143 to 147,
ii) introducing the polynucleotide into a plant,
iii) determining whether the plant, preferably when grown under stress conditions such as water-stressed conditions at least some point during flowering and/or anthesis, has one or more of the following features;
   a) an enhanced level of fructan in the stem and/or leaf sheath,
   b) an increased level of one or more of sucrose:sucrose 1-fructosyltransferase (1-SST) activity, sucrose:fructan 6-fructosyltransferase (6-SFT) activity, fructan:fructan 1-fructosyltransferase (1-FFT) activity, γ-vacuolar processing enzyme (γ-VPE) activity and fructokinase 1 (FK1) activity in the stem and/or leaf sheath,
   c) an increased level of expression in the stem and/or leaf sheath of an endogenous gene(s) encoding one or more of 1-SST, 6-SFT, 1-FFT, γ-VPE and FK1,
   d) a higher grain yield and/or average grain size,
   e) an increased level of fructan in the seed, or
   f) more tolerance to stress conditions,
relative to an isogenic plant lacking the polynucleotide, and
iv) optionally, selecting a polynucleotide which when expressed confers one or more of said features.

Preferably, the polynucleotide encodes a polypeptide comprising amino acids having a sequence as provided in any one of SEQ ID NOs: 1 to 4, a biologically active fragment thereof, or an amino acid sequence which is at least 30% identical to any one or more of SEQ ID NOs: 1 to 4.

Preferably, the polynucleotide encodes a polypeptide comprising amino acids having a sequence as provided as amino acids 27 to 130 of SEQ ID NO: 1, a biologically active fragment thereof, or an amino acid sequence which is at least 30% identical to amino acids 27 to 130 of SEQ ID NO: 1.

In a preferred embodiment, the plant is a cereal plant such wheat, oats, rye or barley.

In an embodiment, the polypeptide is a plant polypeptide or mutant thereof.

In a further embodiment, step ii) further comprises stably integrating the polynucleotide operably linked to a promoter into the genome of the plant.

In another aspect, the present invention provides fructan produced from a plant or part thereof of the invention.

Also provided is the use of fructan of the invention in a food as a sweetening agent, a low calorie additive, a bulking agent, a dietary fibre, a texturizing agent, a preservative, a probiotic agent or the like or any combination of one or more thereof.

In another aspect, the present invention provides a method for preparing a food or beverage, comprising mixing fructan of the invention with another food or beverage ingredient.

In yet another aspect, the present invention provides a method for providing fructan to improve one or more indicators of health in a mammal, wherein the method comprises administering, to the mammal, a plant, plant part, food product, beverage product and fructan of the invention.

In an embodiment, the fructan is in a pharmaceutical composition further comprising one or more acceptable carriers.

In a further embodiment, the one or more indicators of health is an increased number of beneficial intestinal bacteria, reduced number of aberrant crypt foci, increased mineral absorption, reduced level of insulin, reduced glycaemic index, reduced glycaemic load, reduced blood glucose, reduced blood pressure, reduced body weight, reduced blood cholesterol level, increased HDL cholesterol level, increased bone density, increased calcium levels, more frequent bowel movement, or improved blood serum cardiovascular profile.

In yet another aspect, the present invention provides a method for ameliorating one or more symptoms of a condition associated with low levels of dietary fructan in a subject, said method comprising administering orally to the subject one or more of a plant, plant part, food product, beverage product and fructan of the invention for a time and under conditions sufficient to ameliorate one or more symptoms.

In an embodiment, the condition is selected from the group consisting of diabetes, obesity, heart disease, hypertension, constipation, osteoporesis and cancer.

In a further embodiment, the subject is a human.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. The nucleotide sequence alignment of three MYB13 genes isolated from *Triticum aesticum* cv. Babax. The sequences shown in upper-case letters are from the translation start codon to the stop codon of correctly spliced transcripts (short-form transcripts) of TaMYB13-1 (JF288934), TaMYB13-2 (JN191346) and TaMYB13-3 (JN191347). An unspliced intron (lower-case sequence) present in each long-form transcript (TaMYB13-1, JN191348; TaMYB13-2, JF288935; TaMYB13-3, JF288936) is also shown. The sequences for transcript-specific primers used for quantitative real-time PCR, as listed in Table 2, are indicated in bold except the anti-sense primer common for the unspliced forms of three TaMYB13 genes that is indicated by an arrow. Short form cDNAs for TaMYB13-1, -2 and -3 provided as SEQ ID NOs 5 to 7 respectively, with long forms provided as SEQ ID NOs 9 to 11 respectively.

FIG. 2. Transactivation of fructosyltransferase promoter-driven reporter genes by TaMYB13 in wheat leaves.

(a) Transactivation of fructosyltransferase promoter-driven reporter genes. Xylanase A (XynA) is a reporter for quantification of the expression levels of reporter genes (Hv6-SFTSXR Ta6-SFT1SXR and Ta1-SSTSXR). HvD8MYB13R is an effector gene, driven by a constitutive barley promoter (HvDhn8s). Transactivation was analysed using transient expression assays with which constructs were bombarded into excised wheat leaves on filter paper immersed in 50 mM sucrose and 10 mM potassium phosphate, pH6.5. Values are means±SD of 3-4 biological replicates. Ubi1 promoter-driven GUS+ was used as a control gene for normalisation of transformation efficiency. Relative expression levels of the reporter gene are expressed as the relative ratio of XynA to GUS activity. The activity ratio of the xylanase reporter construct alone was arbitrarily set as 1.

(b) Fructosyltransferase promoter truncation and point-mutation analysis. Relative promoter activity of the truncated or mutated promoter-driven XynA reporter constructs with or without co-bombardment of HvD8MYB13R was quantified as in (a). The promoter activity of Ta6-SFT1SXR or Ta1-SSTSXR reporter construct without HvD8MYB13R was arbitrarily set as 1. Values are means±SD of 4 biological replicates. The nucleotide sequences of TaMYB13-binding sites in the Ta6-SFT1 and Ta1-SST promoters are shown in FIG. 11. Mutated TaMYB13-binding site in Ta6-SFT1SXR-mS1 and Ta1-SSTSXR-ΔS1mS2 is indicated by a triangle. In Ta6-SFT1-SS duplicated Hv6-SFT-s1 (TATGTTAGG-TAC—SEQ ID NO:89)) sites were indicated by two unfilled boxes. TATA, TATA box.

*$P<0.01$ for differences between two experimental groups using Student's t-test.

FIG. 3. Positive correlation between the MYB (Ta.12834.1.S1_s_at) mRNA level and WSC, fructan concentration or fructosyltransferase mRNA levels in the stem of field-grown SB lines. Relative mRNA levels are expressed as Affymetrix array hybridisation signal. Sixteen biological samples were used for analyses and derived from 8 SB lines with two replicated plots.

(a) Correlation between the Ta.12834.1.S1_s_at MYB mRNA level and WSC or fructan concentration. DW, dry weight.

(b) Correlation in expression between the Ta.12834.1.S1_s_at MYB and three fructosyltransferases. **P<0.01.

FIG. 4. Open reading frames (ORF) and amino acid sequence alignment of three TaMYB13 genes. The upper panel shows ORFs encoded by correctly spliced transcript forms. The lower panel shows the first ORFs encoded by the unspliced transcript forms. The amino acid residues in the lower-case letters are encoded by the sequences in the unspliced introns. Proteins encoded by short form cDNAs for TaMYB13-1, -2 and -3 provided as SEQ ID NOs 1 to 3 respectively, with long forms provided as SEQ ID NOs 25 to 27 respectively.

FIG. 5. Amino acid sequence alignments of TaMYB13-1 and its closest homologues.

(a) Alignment of TaMYB13-1 (JF288934) (SEQ ID NO:1) with HvMYB13 (SEQ ID NO:4). The MYB domain is underlined. HvMYB13 was assembled from the following barley ESTs: BF626054, GH211178, BJ482674, BJ484007, BU991607, BF253478 and BQ765490.

(b) MYB domain alignment of TaMYB13-1 (SEQ ID NO:22) with HvMYB13 (SEQ ID NO:23) and its closest homologues in rice and *Arabidopsis*. AtMYB48 (AT3G46130.1) (SEQ ID NO:18); AtMYB59 (AT5G59780.3) (SEQ ID NO:19); Os11g47460.1 (LOC_Os11g47460.1) (SEQ ID NO:20); Os12g37970.1 (LOC_Os12g37970.1) (SEQ ID NO:21); Os01g74410.1 (LOC_Os01g74410.1) (SEQ ID NO:24).

FIG. 6. Amino acid sequence alignment and identities between TaMYB13-1 and its closest homologues in *Arabidopsis* and rice (SEQ ID NOs 13 to 21). *Arabidopsis* and rice MYB genes were identified through blastp search in the Plant Transcription Factor database (pintfdb.bio.uni-potsdam.de/v2.0/).

Figure 7:
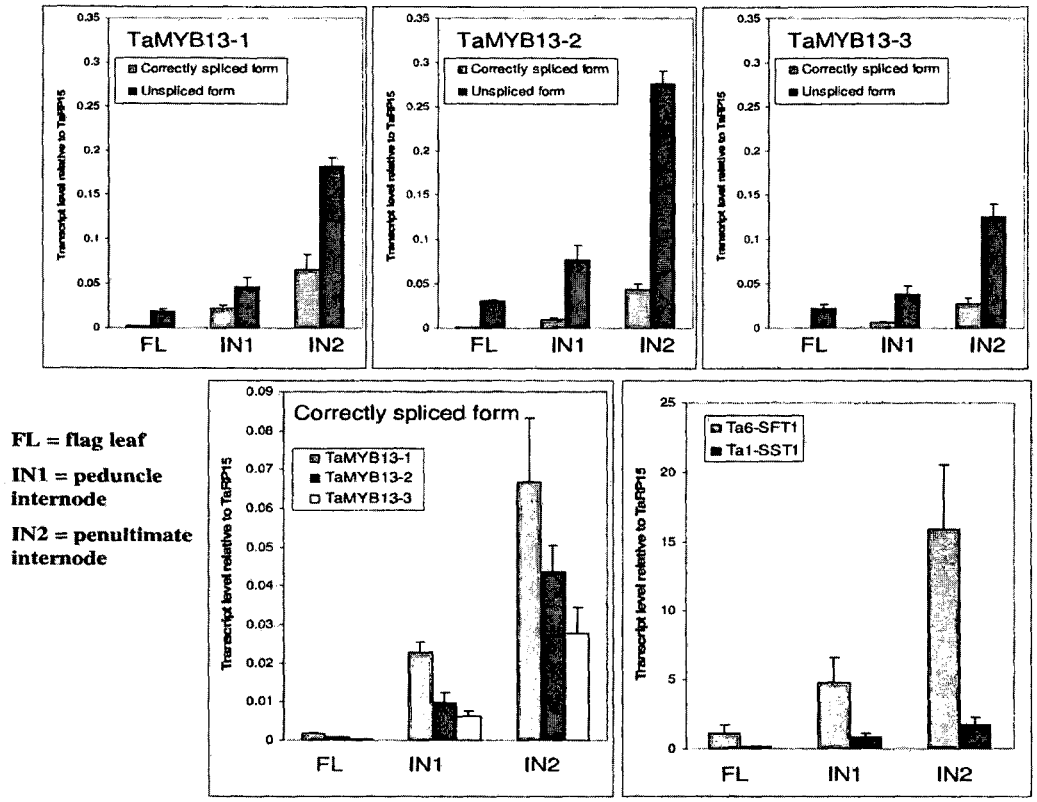

FIG. 7. Relative transcript abundance of TaMYB13-1, TaMYB13-2 and TaMYB13-3, Ta6-SFT1 and Ta1-SST1 in wheat leaves and stem at anthesis. Both short (correctly spliced) and long (unspliced) transcript forms were analysed using transcript-specific primers for each TaMYB13 gene as illustrated in FIG. 1. Flag leaf and internode samples were derived from wheat genotype SB169 at anthesis grown in controlled environment conditions. Relative transcript abundance among genes was calculated using the method of determination of the apparent expression level of each gene relative to an internal reference gene, TaRP15 (Stephenson et al., 2007 and Kam et al., 2008). Values in Panel (a) are means±SD of 3 biological replicates. Correlation coefficients between TaMYB13 and frucotsyltransferase in Panel (b) are derived from 9 biological samples (3 replicates each organ: flag leaf, peduncle and penultimate internodes). * Statistically significant at P<0.01.

Figure 8:
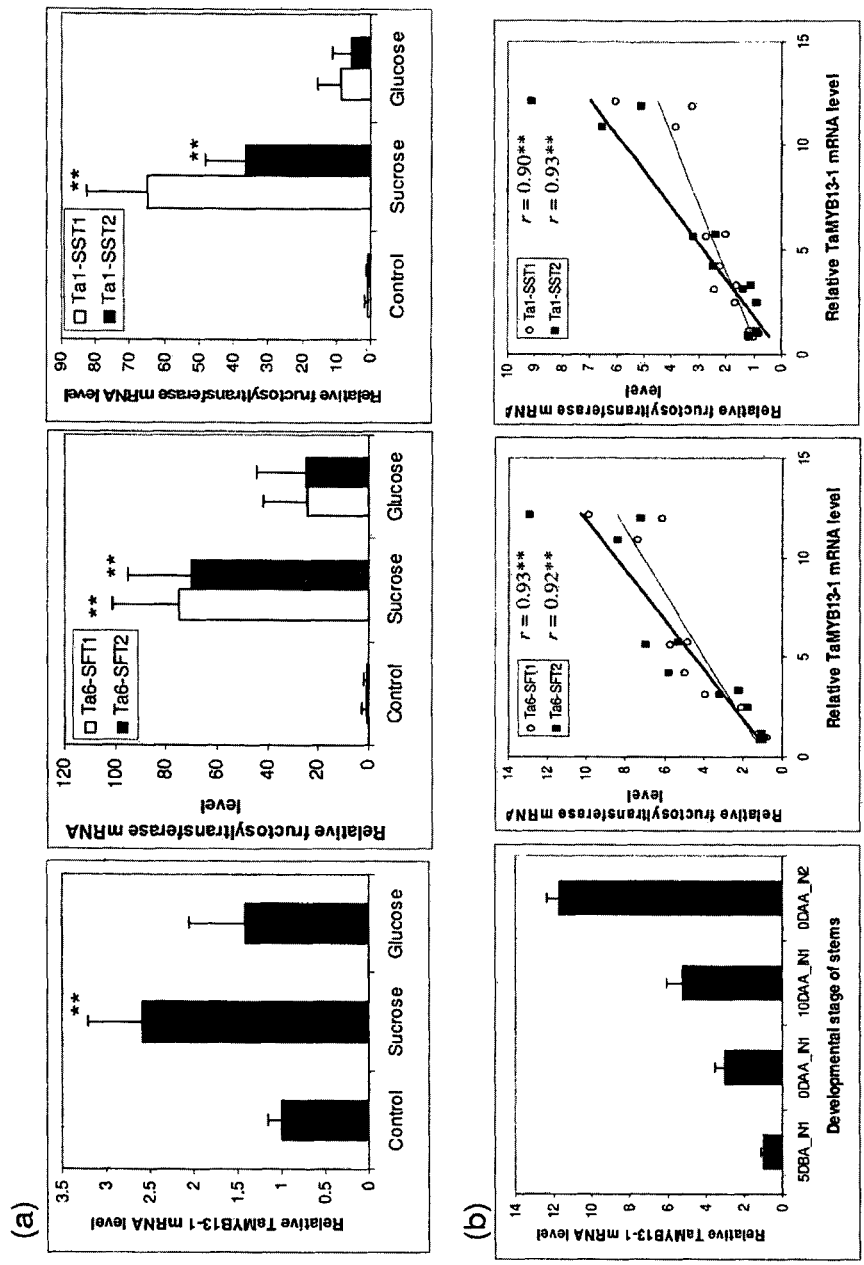

FIG. 8. Changes in expression of TaMYB13-1 and fuctosyltransferases in wheat leaves in response to sugar treatments and in wheat stem during stem development. Expression levels were analysed using quantitative RT-PCR. Primers specific for the correctly spliced form of TaMYB13-1 was used.

(a) In response to sugar treatment. **P=or <0.01 for differences between treatment and control using Student's t-test.

(b) Developmental changes in the stem. 5DBA_IN1, internode 1 (peduncle) samples at 5 days before anthesis; 0DAA_IN1, internode 1 at anthesis, 10DAA-IN1, internode 1 at 10 days after anthesis, 0DAA_IN2, internode 2 (penultimate internode) at anthesis. **P<0.01.

FIG. 9. TaMYB13 DNA-binding sequences determined using in vitro binding site selection. All these selected oligonucleotides contain functional TaMYB13-binding sites as verified in DNA-binding assays. The nucleotides in the core binding sequence are in bold. The logo of the TaMYB13 binding sequence profile was generated using the MEME program (meme.sdsc.edu/meme/cgi-bin/meme.cgi). Sequences provided as SEQ ID NOs 28 to 45 in the same order as present in the Figure.

Figure 10:
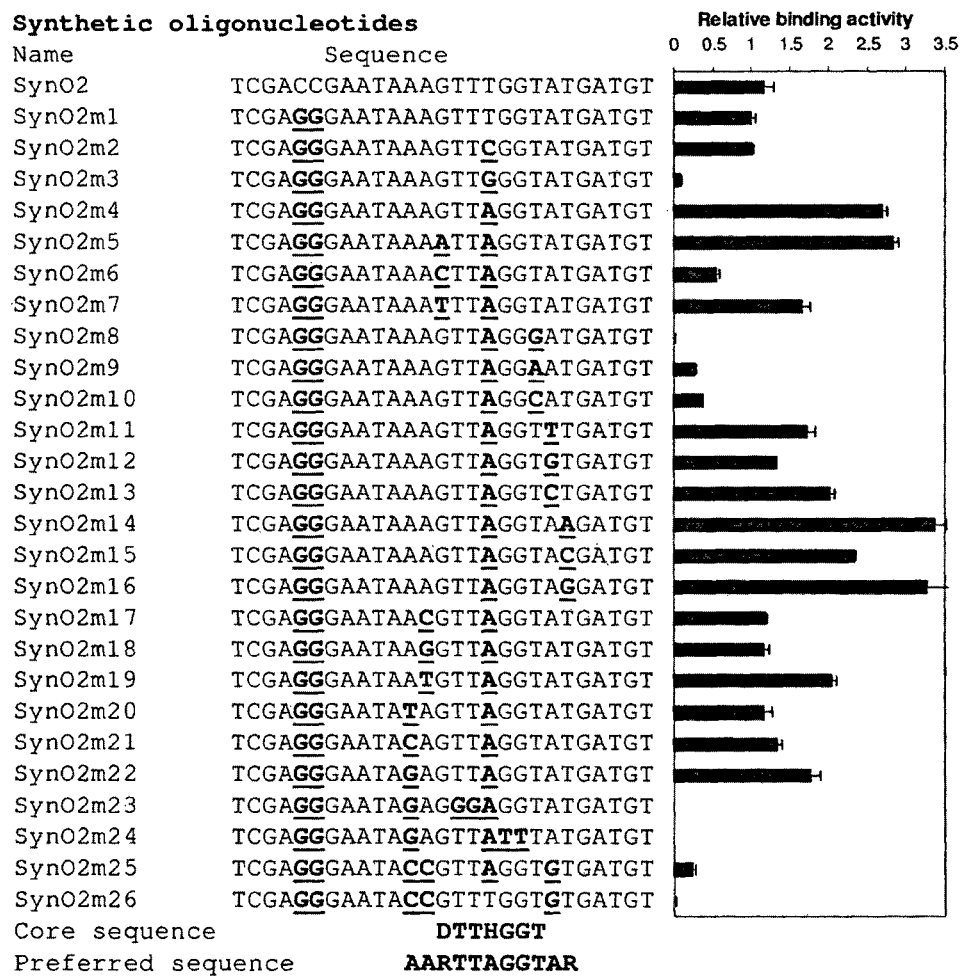

FIG. 10. Defining the DNA-binding sequence specificity of TaMYB13 using base substitution mutagenesis. One of the two TaMYB13-binding sites (in different orientations) in SynO2 was made dysfunctional by replacing ACCGAAT (=ATTCGGT in the reverse complementary strand) with AGGGAAT in SynO2 m1. Bases that were substituted are unlined. The values for the relative TaMYB13-binding activity of these oligonucleotides are shown on the right and are means±SD of three assays. The defined core TaMYB13-binding sequence by this analysis is DTTHGGT, where D=AGt and H=Atc (the preferred bases in capital letters). R=AG. Sequences provided as SEQ ID NOs 46 to 74 in the same order as present in the Figure.

FIG. 11. TaMYB13-binding sites in the promoter regions of fructosyltransferase genes in barley and wheat.

(a) DTTHGGT motifs in barley and wheat fructosyltransferase promoters and TaMYB13-1 binding activity. Start positions are relative to the translation start codon. GenBank accession numbers of these promoters are AJ306962 (Hv6-SFT), HQ738530 (Ta6-SFT1), HQ738531 (Ta6-SFT2) and FJ228689 (Ta1-SST). DTTHGGT motifs are in bold. TaMYB13 binding activity is expressed as relative to that of SynO2. Each value is the mean±SD of 3-4 replicated assays. Sequences provided as SEQ ID NOs 75 to 87 in the same order as present in the Figure.

(b) TaMYB13 binding to Hv6-SFT-s1 and Ta1-SST-s2 is shown as bright fluorescence as a result of the hydrolysis of MUC by the cellulase activity of CELD-fused TaMYB13 binding to the biotin-labelled oligonucleotides immobilised in streptavidin-coated wells. Control sequence without a TaMYB13 binding site is 5'-GAGAATTTGCCGTT-TATCTAGAAATTACCT (SEQ ID NO:88).

Figure 12:
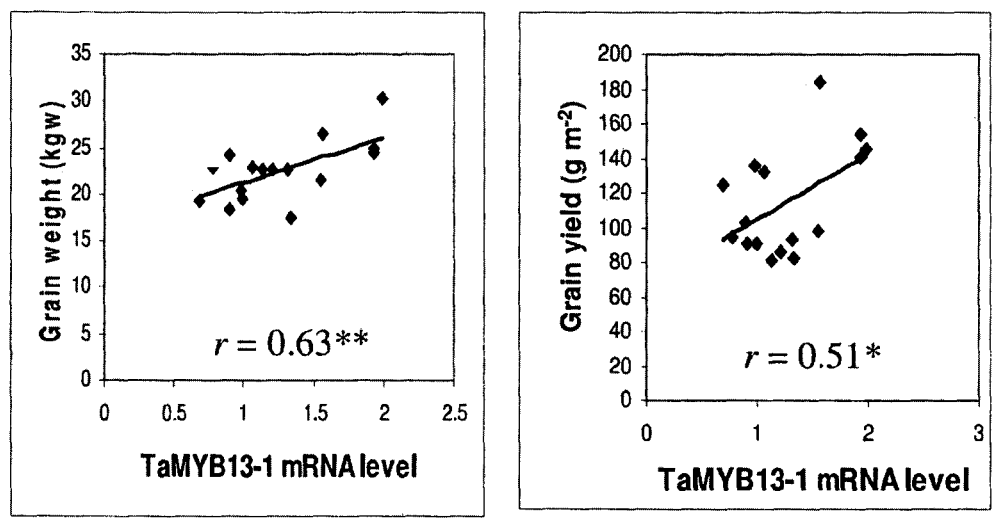

FIG. 12. Expression levels of TaMYB13-1 are positively correlated with grain weight and yield among 16 SB lines grown in the field under rain-fed conditions. Relative expression levels of TaMYB13-1 among 16 SB lines were measured in the stems of field grown plants at anthesis using quantitative RT-PCR. Kgw is thousand grain weight. *P<0.05; **P<0.01.

Figure 13:
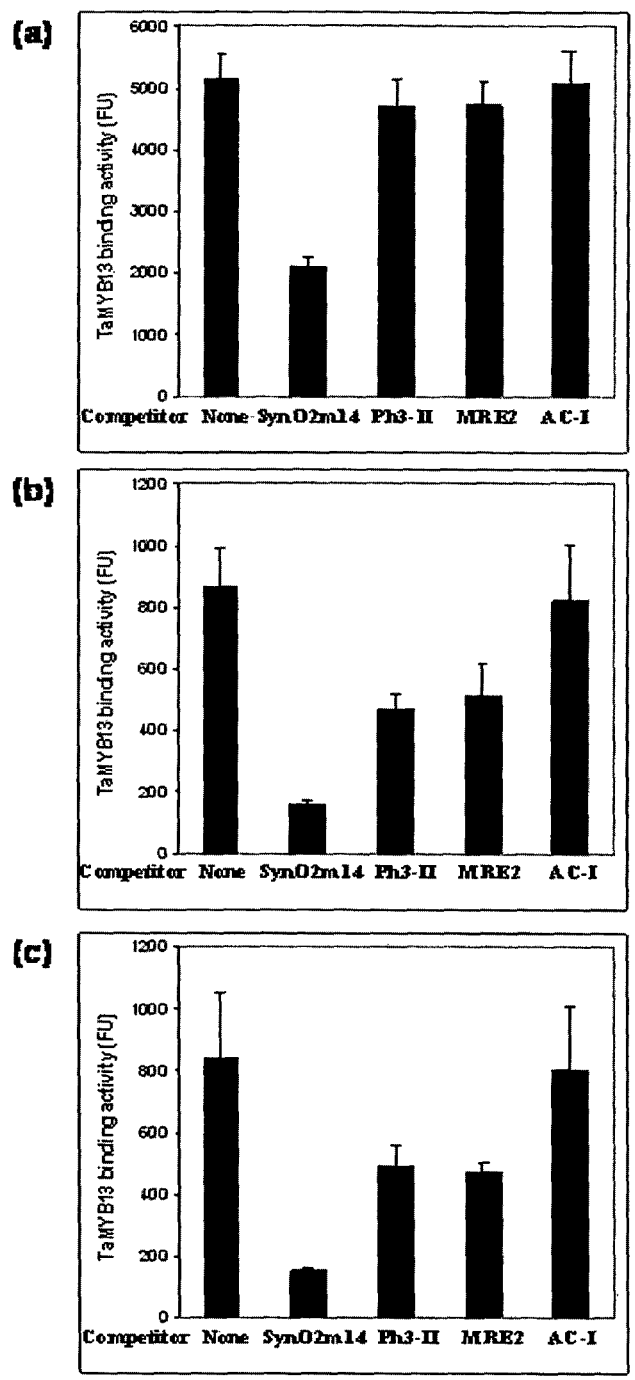

FIG. 13. Competition analysis of TaMYB13 binding activity to various elements. Three biotin-labelled probes were analysed: (a) SynO2m14 (a preferred TaMYB13-binding sequence, 5'-TCGAGGGAATAAAGTTAGG-TAAGATGT (SEQ ID NO:60)), (b) MYB.Ph3-II (Ph3-II, 5'-TCGAGGGAATAAAGTTAGTTATGATGT (SEQ ID NO:90)) and (c) MRE2 (5'-TCGAGGGAATTATAACG-GTTTTTTGAT (SEQ ID NO:91)). The binding sequences are in bold. Four non-labelled oligonucleotides [SynO2m14, Ph3-II, MRE2 and AC-I (5'-TCGAGGGAATAAGGTAG-GTGGATGATGT (SEQ ID NO:92))] at the concentration of 2.5 times higher than that of a biotin-labelled probe were used as competitors. Relative TaMYB13 binding activity values are fluorescence units (FU) and presented as means±SD of three replicated assays.

Figure 14:
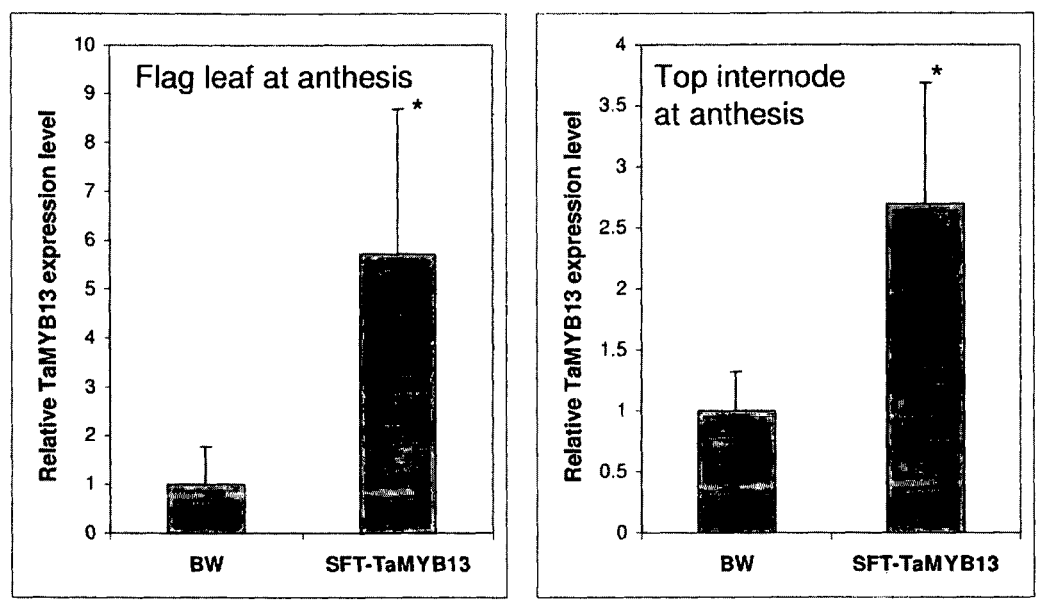

FIG. 14. Relative TaMYB13 expression levels in Bobwhite (BW) (n=3) and T2 transgenic lines carrying a barley 6-SFT promoter-driven TaMYB13 construct (SFT-TaMYB13) (n 5-7). *P<0.05.

Figure 15:
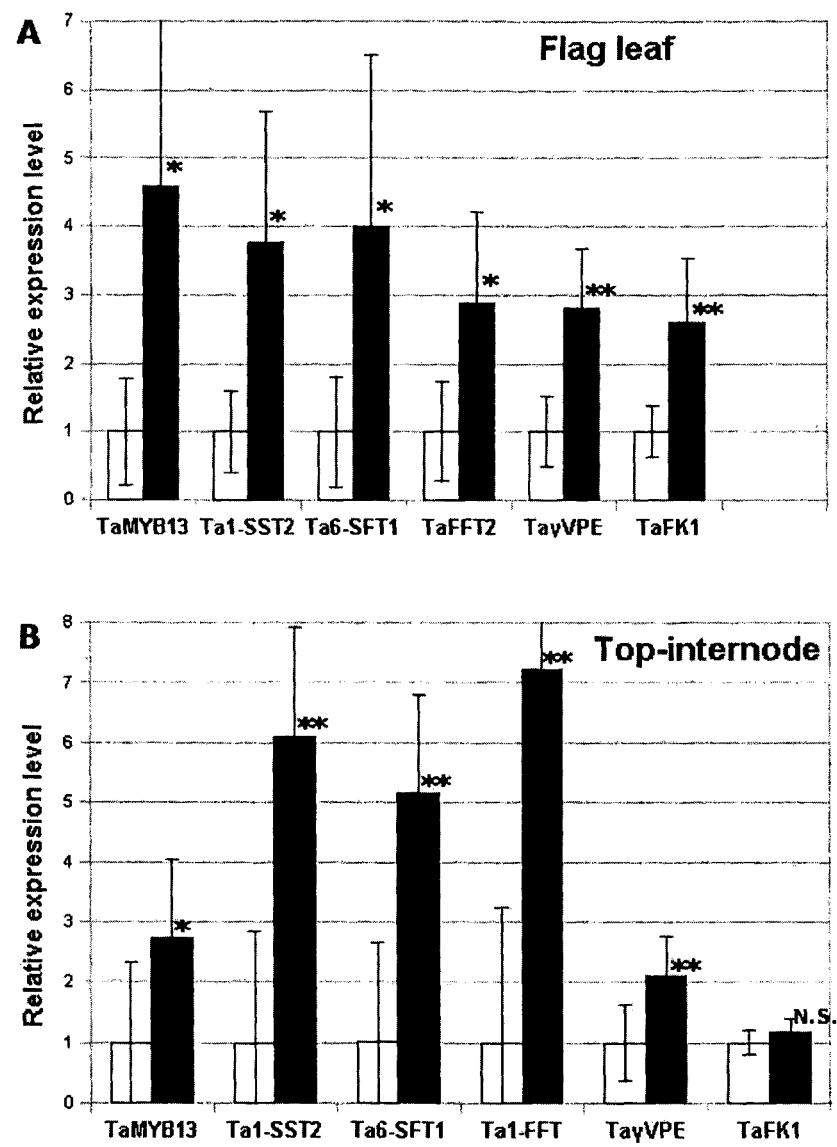

FIG. 15. Relative expression levels of TaMYB13 and its target genes in Bobwhite control plants (white bars) and TaMYB13 transgenic lines (black bars). A. Relative expression levels of TaMYB13 and its target genes in flag leaves harvested at anthesis. B. Relative expression levels of TaMYB13 and its target genes in the top-internode harvested at anthesis. The expression of the Bobwhite control plants was set at 1, and was normalised against the internal control genes TaRP15 and TaRPII36. *P<0.05; **P<0.01.

Figure 16:
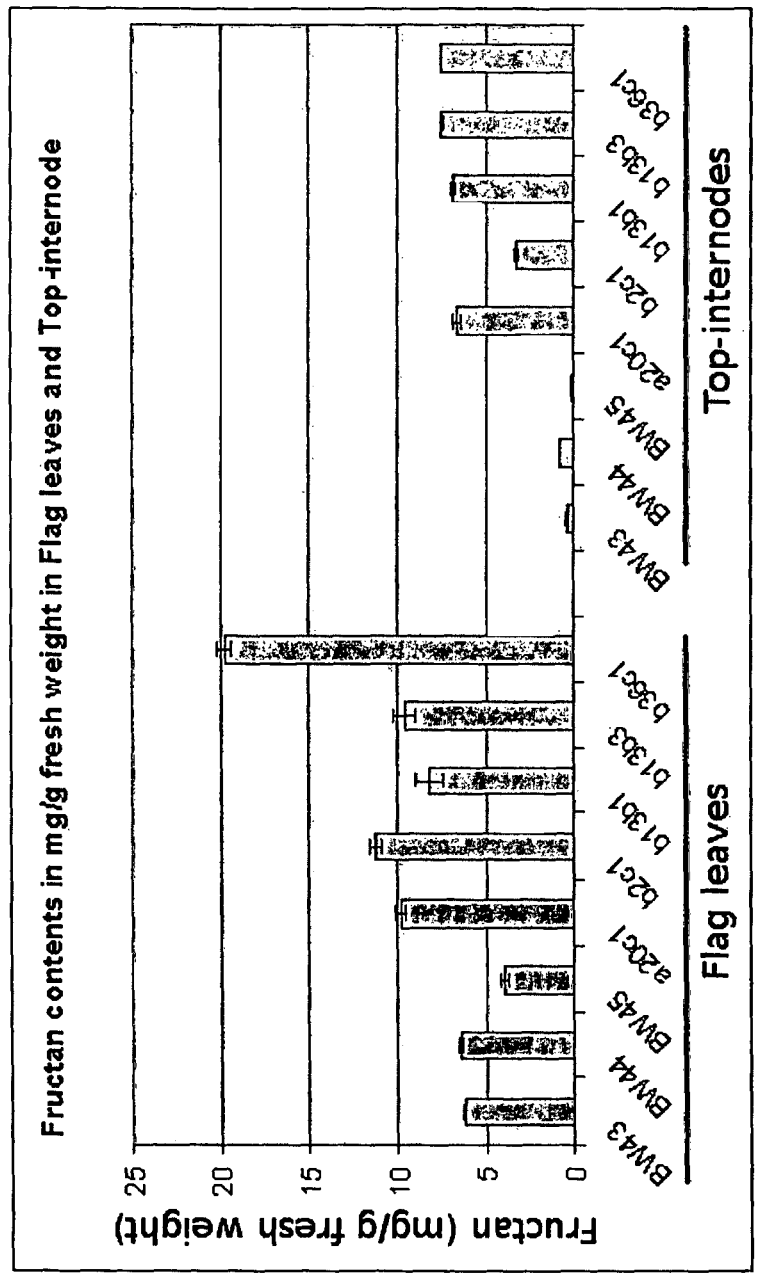

FIG. 16. Fructan concentrations in the flag leaf and top-internode of transgenic plants over-expressing TaMYB13 and Bobwhite control plants (BW43/44/45). Samples were collected at anthesis. The increase in fructan concentration was significant in both flag leaf and top-internode samples (P<0.01).

Figure 17:
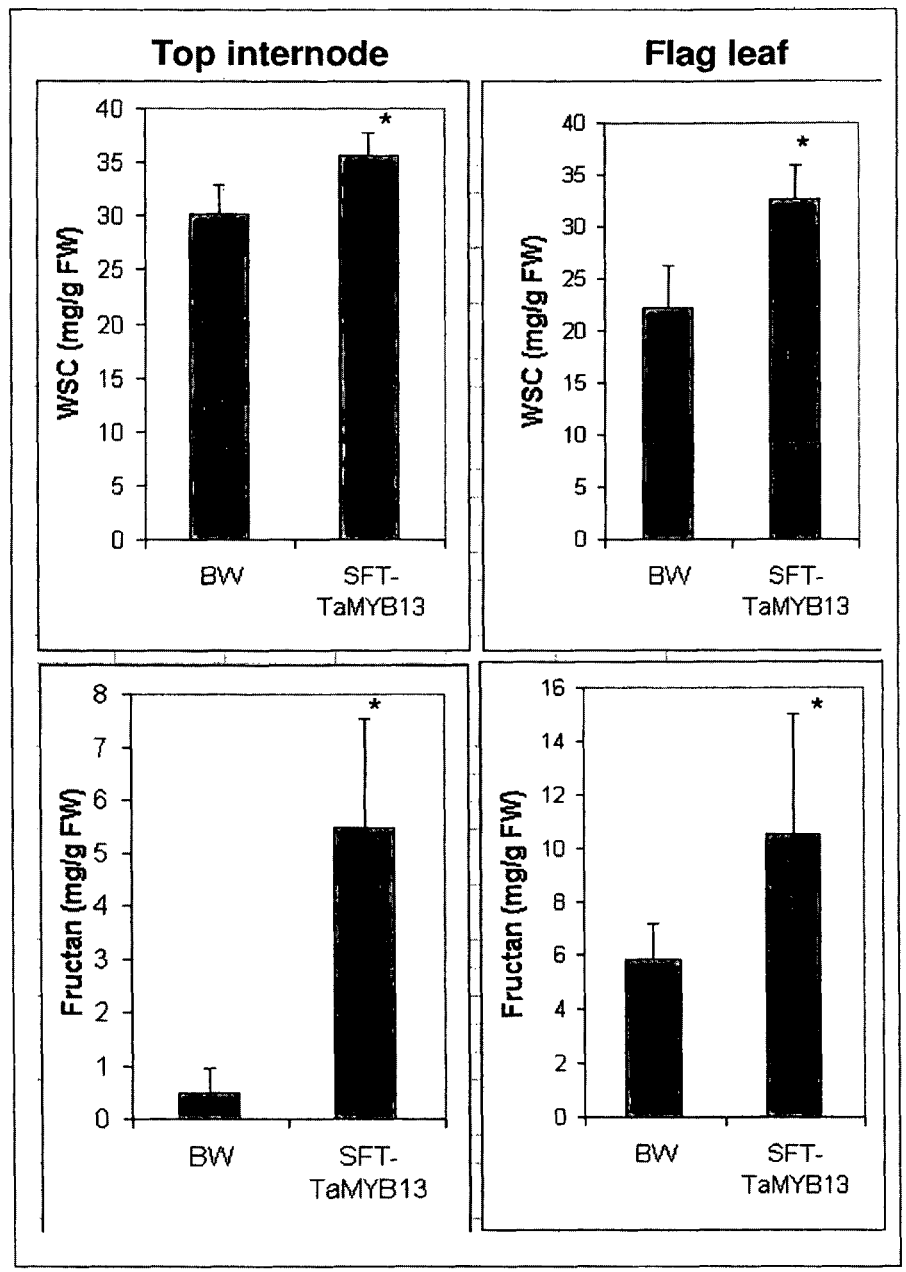

FIG. 17. WSC and fructan concentrations in the top internode and flag leaf of Bobwhite (BW) (n=3) and T2 transgenic lines carrying a barley 6-SFT promoter-driven TaMYB13 construct (SFT-TaMYB13) (n 6-7) at anthesis. *P=or <0.05.

Figure 18:
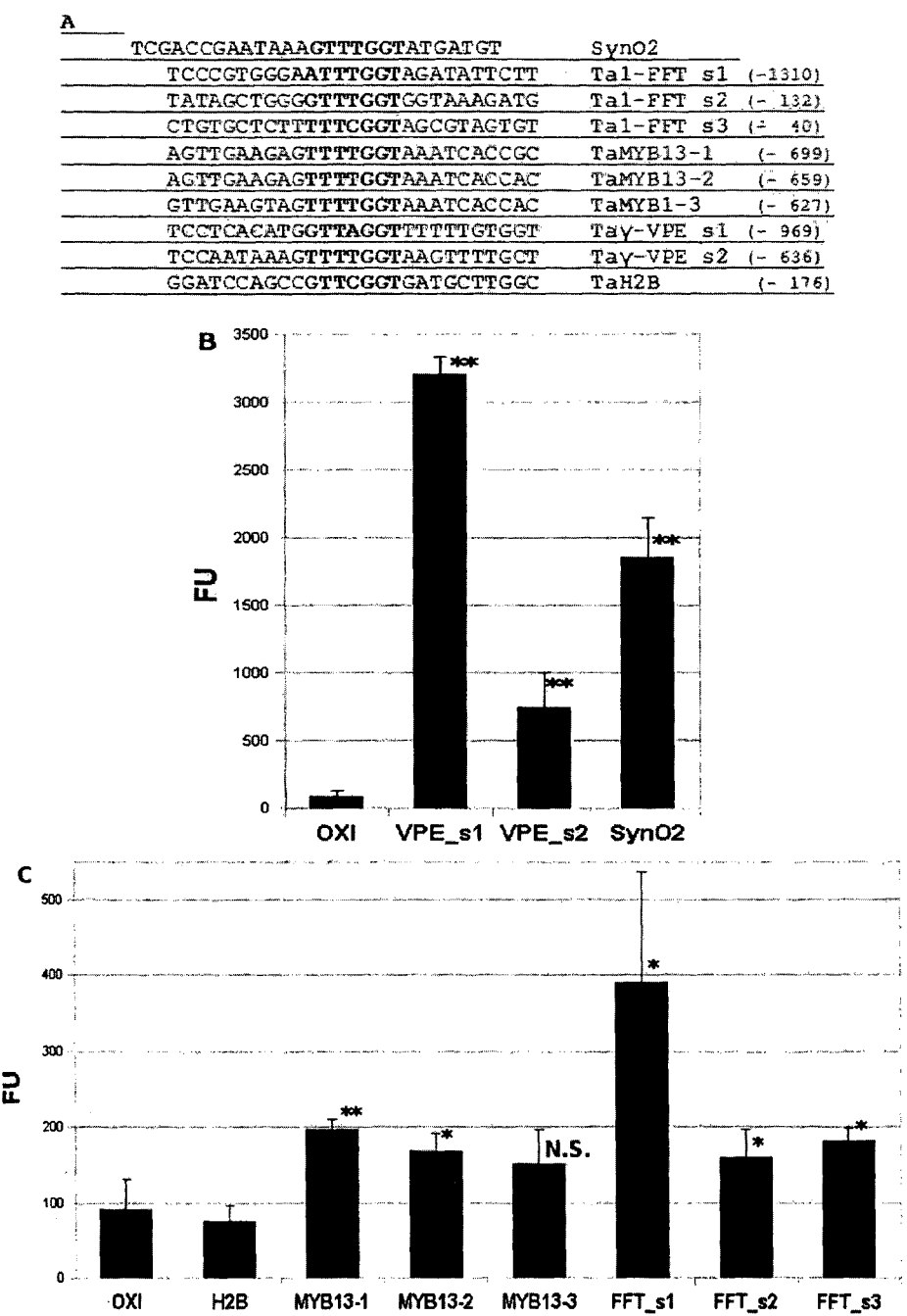

FIG. 18. In vitro DNA-binding assays using TaMYB13 DNA-binding motifs found in target genes up-regulated in transgenic plants over-expressing TaMYB13. A, TaMYB13 DNA-binding sequences found in the upstream regulatory regions of TaMYB13 target genes. B, in vitro DNA-binding assays determining the binding of TaMYB13 to the motifs found in the upstream regulatory regions of Taγ-VPE and the positive control SynO2. C, in vitro DNA-binding assays determining the binding of TaMYB13 to the motifs found in the upstream regulatory regions of TaH2B, TaMYB13-1/2/3, Ta1-FFT s1, s2, s3. Fluorescence released from the cleavage of methylumbelliferyl β-D-cellulobioside (MUC) by CEL-D fused to TaMYB13 was measured after 3 hours of incubation at 40° C. Displayed values are averages of 3 replicates. Oxi is the negative control, not containing TaMYB13 binding motifs, *P<0.05; **P<0.01; N.S. not significant. Sequence of SynO2 provided as SEQ ID NO:26, others are SEQ ID NOs 156 to 164 in the order provided.

Figure 19:
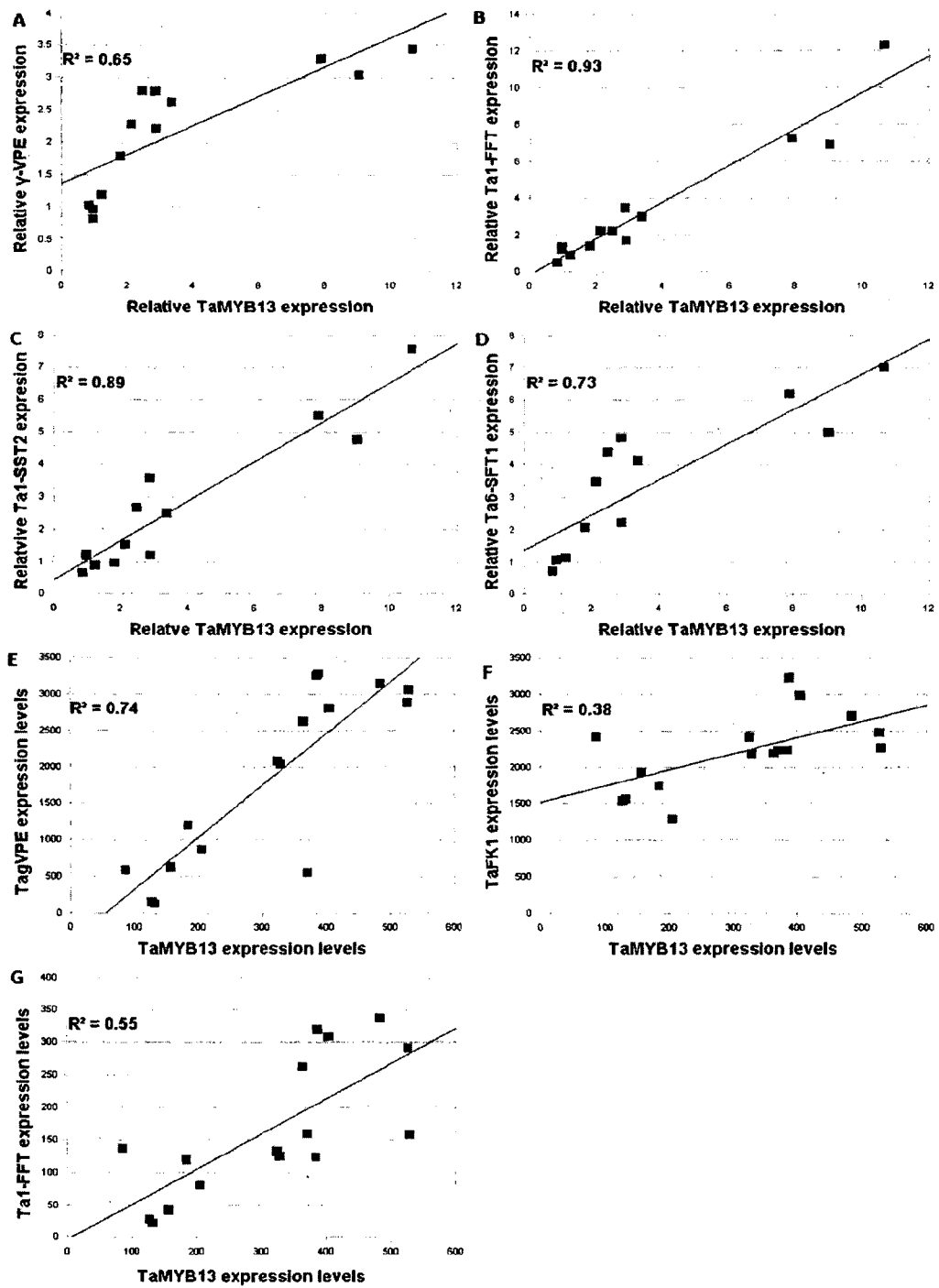

FIG. 19. Correlation in expression between TaMYB13 and its target genes in developing stems (A-D) and in recombinant inbred lines (E-G).

Figure 20:
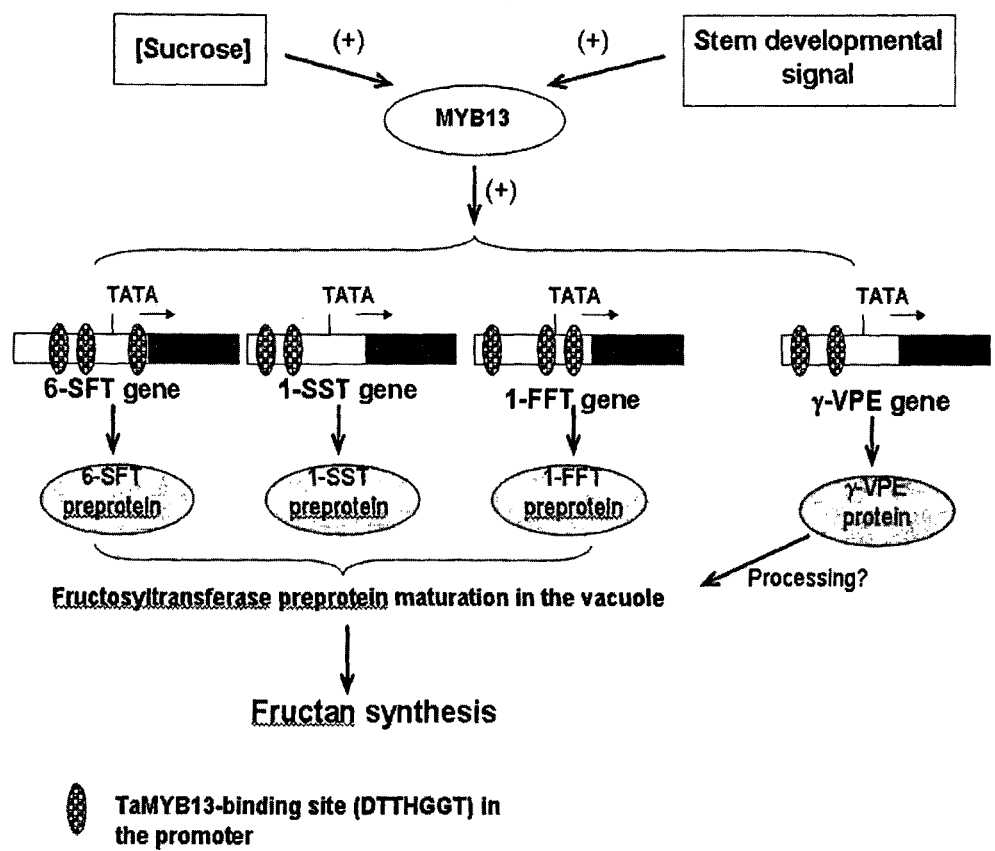

FIG. 20. Illustration of a proposed sucrose and stem developmental signal-mediated MYB13 regulatory pathway for fructan synthesis in temperate cereals. The MYB13-binding sites in 1-FFT, γ-VPE, 6-SFT1 and 1-SST promoters are indicated.

KEY TO THE SEQUENCE LISTING

SEQ ID NO:1—Wheat MYB13-1.
SEQ ID NO:2—Wheat MYB13-2.
SEQ ID NO:3—Wheat MYB13-3.
SEQ ID NO:4—Barley MYB13.
SEQ ID NO:5—Nucleotide sequence encoding wheat MYB13-1.
SEQ ID NO:6—Nucleotide sequence encoding wheat MYB13-2.
SEQ ID NO:7—Nucleotide sequence encoding wheat MYB13-3.
SEQ ID NO:8—Nucleotide sequence encoding barley MYB13.
SEQ ID NO:9—Unspliced variant of nucleotide sequence encoding wheat MYB13-1.
SEQ ID NO:10—Unspliced variant of nucleotide sequence encoding wheat MYB13-2.
SEQ ID NO:11 Unspliced variant of nucleotide sequence encoding wheat MYB13-3.
SEQ ID NO:12—Unspliced variant of nucleotide sequence encoding barley MYB13.
SEQ ID NO:13—Rice MYB13 homologue designated LOC_Os11g47460.1.
SEQ ID NO:14—Rice MYB13 homologue designated LOC_Os12g37970.1.
SEQ ID NO:15—*Arabidopsis thaliana* MYB13 homologue designated AT3G46130.1.
SEQ ID NO:16—*Arabidopsis thaliana* MYB13 homologue designated AT5G59780.3.
SEQ ID NO:17—Rice MYB13 homologue designated LOC_Os01g74410.1.
SEQ ID NO:18—DNA binding domain of *Arabidopsis thaliana* MYB13 homologue designated AT3G46130.1.
SEQ ID NO:19—DNA binding domain of *Arabidopsis thaliana* MYB13 homologue designated AT5G59780.3.
SEQ ID NO:20—DNA binding domain of rice MYB13 homologue designated LOC_Os11g47460.1.
SEQ ID NO:21—DNA binding domain of rice MYB13 homologue designated LOC_Os12g37970.1.
SEQ ID NO:22—DNA binding domain of wheat MYB13-1.
SEQ ID NO:23—DNA binding domain of barley MYB13.
SEQ ID NO:24—DNA binding domain of rice MYB13 homologue designated LOC_Os01g74410.1.
SEQ ID NO:25—Protein encoded by unspliced cDNA of wheat MYB13-1.
SEQ ID NO:26—Protein encoded by unspliced cDNA of wheat MYB13-2.
SEQ ID NO:27—Protein encoded by unspliced cDNA of wheat MYB13-3.
SEQ ID NOs 28 to 44 and 156 to 164—Variants of wheat MYB13-1 binding sites.
SEQ ID NO:45—Consensus MYB13 polypeptide binding site.
SEQ ID NOs 46 to 72—Synthetic oligonucleotides used in binding studies.
SEQ ID NO:73—Core MYB13 polypeptide binding site.
SEQ ID NO:74—Preferred MYB13 polypeptide binding site.
SEQ ID NOs 75 to 87—Regions of 6-SFT and 1-SST genes comprising MYB13 binding sites.
SEQ ID NOs 88 to 142—Oligonucleotides.
SEQ ID NO:143—*Festuca arundinacea* MYB13 homologue designated DT704689.
SEQ ID NO:144—Wheat MYB13 homologue designated TaMYB807.
SEQ ID NO:145—*Festuca pratensis* MYB13 homologue designated G0861792.1.
SEQ ID NO:146—*Dactylis glomerata* MYB13 homologue designated HO165053.
SEQ ID NO:147—*Pseudoroegneria spcata* MYB13 homologue designated FF341046.
SEQ ID NOs 148 to 151—Motifs in MYB13 DNA binding domain.
SEQ ID NOs 152 to 155—Motifs in wheat and barley MYB13 polypeptides.
SEQ ID NO: 165—Wheat γ-vacuolar processing enzyme.
SEQ ID NO: 166—Nucleotide sequence encoding wheat γ-vacuolar processing enzyme.
SEQ ID NO: 167—Wheat fructokinase 1.

SEQ ID NO: 168—Nucleotide sequence encoding wheat fructokinase 1.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, plant biology, food processing, plant processing, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−20%, more preferably +/−10%, more preferably +/−5%, even more preferably +/−1%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention relates, in part, to the use of isolated polynucleotides and polypeptides. By "isolated" we mean that the molecule has generally been separated from other molecules with which it is associated or linked in its native state and/or is present as a result of a non-naturally occurring source (for example through the expression of a transgene). This term can include purified molecules as well as recombinant molecules. Preferably, the isolated molecule is at least 90% free from other components with which it is naturally associated.

MYB13 Polypeptides

MYB polypeptides comprise a MYB DNA binding domain that is conserved amongst animals, plants, and yeasts, and which typically consists of one, two or three domains (referred to in the art as R1, R2 and R3 domains) which are each about 50-53 amino acids long and encode three α-helices, with the second and third helices forming a helix-turn-helix (HTH) structure which intercalates in the major groove of DNA (Du et al., 2009; Feller et al., 2011).

As used herein, the term "MYB13 polypeptide" means a polypeptide comprising a MYB DNA binding domain linked to a C-terminal domain which has at least 30% amino acid sequence identity to amino acids 131-260 of SEQ ID NO: 1. The DNA binding domain is thought to interact directly with promoter elements and provides specificity to the interaction, while the C-terminal domain is typically a transcriptional activation domain. In an embodiment, the MYB13 polypeptide consists of an N-terminal region of about 20-30 amino acids linked to the MYB DNA binding domain, in turn linked to a C-terminal domain. The N-terminal region typically comprises 4 or 5 lysine residues and has a net positive charge at neutral pH. In a particularly preferred embodiment, the MYB13 polypeptide comprises a MYB DNA binding domain which comprises one or more, preferably all four, of the following motifs; i) RKGPWTE-QED (SEQ ID NO:148), ii) AKVSGL (SEQ ID NO:149), iii) GKSCRLRWVNYLHP (SEQ ID NO:150), and iv) PGRTDNEIKNYWRTH (SEQ ID NO:151). Preferably, when two or more of the motifs are present they are in the order i) to iv) when considering the amino acid sequence as N-terminus to C-terminus. In a further particularly preferred embodiment, the MYB13 polypeptide comprises a MYB DNA binding domain which comprises amino acids having a sequence as provided as amino acids 27 to 130 of SEQ ID NO: 1, a biologically active fragment thereof, or an amino acid sequence which is at least 75% identical to amino acids 27 to 130 of SEQ ID NO: 1. In a preferred embodiment, the MYB DNA binding domain of a MYB13 polypeptide is 102 to 106 amino acids in length, preferably 103 or 104 amino acids in length. In yet a further embodiment, the MYB13 polypeptide comprises, in the C-terminal domain, one or more, preferably all four, of the following motifs; i) STTTSTS (SEQ ID NO: 152), ii) STTTTSTS (SEQ ID NO:153), iii) TTSSSSSST (SEQ ID NO:154), and iv) PPPSSP (SEQ ID NO:155). In a preferred embodiment, a "MYB13 polypeptide" is a "MYB13 transcription factor".

MYB transcription factors are one of the most abundant classes of transcription factors in plants. In a particularly preferred embodiment, a "MYB13 transcription factor" of the invention is able to bind, and promote the expression of, a gene, for example, a gene encoding one or more of a plant, more preferably a cereal plant, sucrose:sucrose 1-fructosyl-transferase (1-SST), a sucrose: fructan 6-fructosyltransferase (6-SFT), a fructan:fructan 1-fructosyltransferase (1-FFT), a γ-vacuolar processing enzyme (γ-VPE) activity and a fructokinase 1 (FK1). In a further preferred embodiment, a MYB13 polypeptide/transcription factor binds a promoter element of a gene comprising the sequence DTTHGGT (SEQ ID NO: 73) and/or the sequence AART-TAGGTAR (SEQ ID NO: 74) and/or the sequence NNTTNGGTN (SEQ ID NO:45) (nucleotides referred to as D, H and R have their standard meaning in the art). A MYB13 polypeptide/transcription factor useful for the invention comprises amino acids having a sequence as provided in any one of SEQ ID NOs: 1 to 4, 13 to 17 or 143 to 147, a biologically active fragment thereof, or an amino acid sequence which is at least 30%, more preferably at least 50%, more preferably at least 75%, more preferably at least 90%, more preferably at least 95% and even more preferably at least 97%, identical to any one or more of SEQ ID NOs: 1 to 4, 13 to 17 or 143 to 147. More preferably, a MYB13 polypeptide/transcription factor useful for the invention comprises amino acids having a sequence as provided in any one of SEQ ID NOs: 1 to 4, a biologically active fragment thereof, or an amino acid sequence which is at least 30%, more preferably at least 50%, more preferably at least 75%, more preferably at least 90%, more preferably at least 95% and even more preferably at least 97%, identical to any one or more of SEQ ID NOs: 1 to 4.

The terms "polypeptide" and "protein" are generally used interchangeably.

Transgenic plants and host cells of the invention may comprise an exogenous polynucleotide encoding a MYB polypeptide of the invention. In these instances, the plants and cells produce a recombinant MYB polypeptide. The term "recombinant" in the context of a polypeptide refers to the polypeptide when produced by a cell, or in a cell-free expression system, in an altered amount or at an altered rate compared to its native state. Typically, the cell comprises a non-endogenous gene that causes an altered amount of the polypeptide to be produced. In an embodiment, a "recombinant polypeptide" is a polypeptide made by the expression of an exogenous (recombinant) polynucleotide in a cell, preferably a plant cell.

The % identity of a polypeptide is determined by GAP (Needleman and Wunsch, 1970) analysis (GCG program) with a gap creation penalty=5, and a gap extension penalty=0.3. The query sequence is at least 100 amino acids in length, and the GAP analysis aligns the two sequences over a region of at least 100 amino acids, especially when aligning MYB13 DNA binding domains. More preferably, the query sequence is at least 200 amino acids in length, and the GAP analysis aligns the two sequences over a region of at least 200 amino acids More preferably, the query sequence is at least 250 amino acids in length, and the GAP analysis aligns the two sequences over a region of at least 250 amino acids. Even more preferably, the GAP analysis aligns two sequences over their entire length.

As used herein, a "biologically active" fragment is a portion of a polypeptide useful for the invention which maintains a defined activity of the full-length polypeptide such as binding the promoter region of one or more of a plant, preferably a cereal plant, 1-SST gene, 6-SFT gene, 1-FFT gene, γ-VPE gene and a FK1 gene and promoting or enhancing transcription of said gene(s). Preferably, the fragment at least comprises a MYB13 DNA binding domain. Biologically active fragments can be any size as long as they maintain the defined activity but are preferably at least 150, at least 200 or at least 250 amino acid residues long. Preferably, the biologically active fragment maintains at least 10%, at least 50%, at least 75% or at least 90%, of the activity of the full length protein.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 40%, more preferably at least 50%, more preferably at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides useful for the present invention can be prepared by introducing appropriate nucleotide changes into a polynucleotide encoding the polypeptide. Such mutants include, for example, deletions, insertions or substitutions of residues within the amino acid sequence. A combination of deletion, insertion and substitution can be made to arrive at the final construct, provided that the final peptide product possesses the desired characteristics. Preferred amino acid sequence mutants have only one, two, three, four or less than 10 amino acid changes relative to the reference wildtype polypeptide.

Mutant (altered) polypeptides can be prepared using any technique known in the art, for example, using directed evolution or rational design strategies (see below). Products derived from mutated/altered DNA can readily be screened using techniques described herein to determine if they possess MYB13 transcription activity such as by using the method as described in Example 6.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. Sites of interest include those not in an active site, such as a DNA binding domain, and those which are not highly conserved between different species. These sites, especially those falling within a sequence of at least three other identically conserved sites can generally be substituted in a relatively conservative or non-conservative manner. Examples of conservative substitutions are shown in Table 1 under the heading of "exemplary substitutions".

TABLE 1

Exemplary substitutions.

| Original Residue | Exemplary Substitutions |
| --- | --- |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In a preferred embodiment a mutant/variant polypeptide has one or two or three or four conservative amino acid changes when compared to a naturally occurring polypeptide, or up to 10 or 15 or 20 amino acid changes relative to a reference sequence such as, for example, any one or more of SEQ ID NOs: 1 to 4, 13 to 17 or 143 to 147, more preferably amino acids having a sequence as provided in any one or more of SEQ ID NOs: 1 to 4. Details of conservative amino acid changes are provided in Table 1. As the skilled person would be aware, such minor changes can reasonably be predicted not to alter the activity of the polypeptide when expressed in a recombinant cell.

The primary amino acid sequence of MYB13 polypeptides can be used to design variants/mutants thereof based on comparisons with closely related molecules (see FIG. 6). As the skilled addressee will appreciate, residues highly conserved amongst closely, related MYB polypeptides are less likely to be able to be altered, especially with non-conservative substitutions, and activity maintained than less conserved residues. In a preferred embodiment, the changes are not in one or more of the motifs which are highly conserved between the different MYB13 polypeptides, particularly those in the R2 and R3 regions of the DNA binding domain (Du et al., 2009; Feller et al., 2011). In a preferred embodiment, the MYB13 DNA binding domain comprises at least one, preferably all four, of the following motifs;

i) RKGPWTEQED, (SEQ ID NO: 148)

ii) AKVSGL, (SEQ ID NO: 149)

iii) GKSCRLRWVNYLHP, (SEQ ID NO: 150)
and iv) PGRTDNEIKNYWRTH. (SEQ ID NO: 151)

If one or more of the motifs has a mutation, it is preferred that altered amino acid is a conservative change (see Table 1) and/or can be found in a corresponding position of at least one related protein, such as that provided in FIG. 6.

Also included within the scope of the invention are polypeptides of the present invention which are differentially modified in vitro or in vivo during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, which may be useful in assays for determining the level of MYB13 polypeptide expression levels or binding to antibodies etc. The polypeptides may be post-translationally modified in a cell, for example by phosphorylation, which may modulate its activity. These modifications may serve to increase the stability and/or bioactivity of the polypeptide useful for the invention.

Directed Evolution

In directed evolution, random mutagenesis is applied to a protein, and a selection regime is used to pick out variants that have the desired qualities, for example, increased activity. Further rounds of mutation and selection are then applied. A typical directed, evolution strategy involves three steps:

1) Diversification:

The gene encoding the protein of interest is mutated and/or recombined at random to create a large library of gene variants. Variant gene libraries can be constructed through error prone PCR (see, for example, Leung, 1989; Cadwell and Joyce, 1992), from pools of DNaseI digested fragments prepared from parental templates (Stemmer, 1994a; Stemmer, 1994b; Crameri et al., 1998; Coco et al., 2001) from degenerate oligonucleotides (Ness et al., 2002, Coco, 2002) or from mixtures of both, or even from undigested parental templates (Zhao et al., 1998; Eggert et al., 2005; Jézéquek et al., 2008) and are usually assembled through PCR. Libraries can also be made from parental sequences recombined in vivo or in vitro by either homologous or non-homologous recombination (Ostermeier et al., 1999; Volkov et al., 1999; Sieber et al., 2001). Variant gene libraries can also be constructed by sub-cloning a gene of interest into a suitable vector, transforming the vector into a "mutator" strain such as the E. coli XL-1 red (Stratagene) and propagating the transformed bacteria for a suitable number of generations. Variant gene libraries can also be constructed by subjecting the gene of interest to DNA shuffling (i.e., in vitro homologous recombination of pools of selected mutant genes by random fragmentation and reassembly) as broadly described by Harayama (1998).

2) Selection:

The library is tested for the presence of mutants (variants) possessing the desired property using a screen or selection. Screens enable the identification and isolation of high-performing mutants by hand, while selections automatically eliminate all nonfunctional mutants. A screen may involve screening for the presence of known conserved amino acid motifs. Alternatively, or in addition, a screen may involve expressing the mutated polynucleotide in a host organism or part thereof and assaying the level of activity.

3) Amplification:

The variants identified in the selection or screen are replicated many fold, enabling researchers to sequence their DNA in order to understand what mutations have occurred.

Together, these three steps are termed a "round" of directed evolution. Most experiments will entail more than one round. In these experiments, the "winners" of the previous round are diversified in the next round to create a new library. At the end of the experiment, all evolved protein or polynucleotide mutants are characterized using biochemical methods.

Rational Design

A protein can be designed rationally, on the basis of known information about protein structure and folding. This can be accomplished by design from scratch (de novo design) or by redesign based on native scaffolds (see, for example, Hellinga, 1997; and Lu and Berry, Protein Structure Design and Engineering, Handbook of Proteins 2, 1153-1157 (2007)). Protein design typically involves identifying sequences that fold into a given or target structure and can be accomplished using computer models. Computational protein design algorithms search the sequence-conformation space for sequences that are low in energy when folded to the target structure. Computational protein design algorithms use models of protein energetics to evaluate how mutations would affect a protein's structure and function. These energy functions typically include a combination of molecular mechanics, statistical (i.e. knowledge-based), and other empirical terms. Suitable available software includes IPRO (Interative Protein Redesign and Optimization), EGAD (A Genetic Algorithm for Protein Design), Rosetta Design, Sharpen, and Abalone.

Polynucleotides and Genes

The present invention refers to various polynucleotides. As used herein, a "polynucleotide" or "nucleic acid" or "nucleic acid molecule" means a polymer of nucleotides, which may be DNA or RNA or a combination thereof, and includes mRNA, cRNA, cDNA, tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which covalently joins the nucleotide sequence and its complement. Basepairing as used herein refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid".

The present invention involves modification of gene activity and the construction and use of chimeric genes and vectors. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A genomic form or clone of a gene containing the transcribed region may be interrupted with non-coding sequences termed "introns" or "intervening regions" or "intervening sequences." An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or for integration into the host genome.

As used herein, a "chimeric gene" refers to any gene that is not a native gene in its native location. Typically, a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations.

Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, artificially mutating genes in cells and artificially altering or modulating the regulation of a gene in a cell or organisms to which these acts have been done or their progeny.

Furthermore, the term "exogenous" in the context of a polynucleotide (nucleic acid) refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

The % identity of a polynucleotide is determined by GAP (Needleman and Wunsch, 1970) analysis (GCG program) with a gap creation penalty=5, and a gap extension penalty=0.3. The query sequence is at least 300 nucleotides in length, and the GAP analysis aligns the two sequences over a region of at least 300 nucleotides, especially when aligning polynucleotides encoding a MYB13 DNA binding domains. Preferably, the query sequence is at least 600 nucleotides in length, and the GAP analysis aligns the two sequences over a region of at least 600 nucleotides. Even more preferably, the query sequence is at least 750 nucleotides in length and the GAP analysis aligns the two sequences over a region of at least 750 nucleotides. Even more preferably, the GAP analysis aligns two sequences over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 40%, more preferably at least 50%, more preferably at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In a further embodiment, the present invention relates to polynucleotides which are substantially identical to those specifically described herein. As used herein, with reference to a polynucleotide the term "substantially identical" means the substitution of one or a few (for example 2, 3, or 4) nucleotides whilst maintaining at least one activity of the native protein encoded by the polynucleotide. In addition, this term includes the addition or deletion of nucleotides which results in the increase or decrease in size of the encoded native protein by one or a few (for example 2, 3, or 4) amino acids whilst maintaining at least one activity of the native protein encoded by the polynucleotide.

Polynucleotides useful for the present invention include those which hybridize under stringent conditions to one or more sequences provided as SEQ ID NOs: 5 to 8. As used herein, stringent conditions are those that (1) employ low ionic strength and high temperature for washing, for example, 0.015 M NaCl/0.0015 M sodium citrate/0.1% NaDodSO$_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Polynucleotides useful for the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

Nucleic Acid Constructs

The present invention includes nucleic acid constructs comprising the polynucleotides useful for the invention, and vectors and host cells containing these, methods of their production and use, and uses thereof. The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame, A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, such as a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of an organism such as a plant. The term constitutive as used herein does not necessarily indicate that a gene is expressed at the same level in all cell types, but that the gene is expressed in a wide range of cell types, although some variation in level is often detectable.

In a preferred embodiment, if a constitutive promoter is used for the invention it results in high levels of mRNA transcribed from the exogenous polynucleotide such that the level of a specific MYB13 polypeptide that is produced in at least a part of the plant is at least about 2 fold or 5 fold or 10 fold or 15 fold or 20 fold higher when compared to an isogenic plant lacking the exogenous polynucleotide. Non-limiting methods for assessing promoter activity are disclosed by Medberry et al. (1992, 1993), Sambrook et al. (1989, supra) and U.S. Pat. No. 5,164,316. Examples of constitutive promoters which may result in these levels of mRNA production include, but are not limited to, the core promoter of the Rsyn7 promoter and other constitutive promoters disclosed in WO99/43838 and U.S. Pat. No. 6,072,050; the core CaMV 35S promoter (Odell et al., 1985) or its enhanced versions; rice actin (McElroy et al., 1990); ubiquitin (Christensen et al., 1989 and 1992); pEMU (Last et al., 1991); MAS (Velten et al., 1984); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

"Selective expression" as used herein refers to expression almost exclusively in specific organs of, for example, the plant, such as, for example, endosperm, embryo, leaves, or root. In a preferred embodiment, a promoter is expressed selectively or preferentially in the stem and/or leaf sheath at least some point during flowering and/or anthesis. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the plastid, cytosol, vacuole, or apoplastic space may be achieved by the inclusion in the structure of the gene product of appropriate signals, eg. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in, for example, a plant. Typically, the promoter is expressed at a level 10-fold higher in the specific tissue or organ than in other tissues or organs.

In an embodiment, the promoter is at least capable of expressing the polypeptide in stems and/or leaves and/or leaf sheath. Examples of such promoters which can be used include those described in Yamamoto et al. (1994 and 1997), Kwon et al. (1994), Gotor et al. (1993), Orozco et al. (1993), Stahl et al. (2004), Nomura et al. (2000), Kwon et al., (1994), Conley et al. (1994), Zaidi et al. (2005), Matsuoka et al. (1993), Stockhaus et al. (1987 and 1989), and US 20050034192.

Expression in the seed and/or endosperm is particularly advantageous when it is desirable to increase the level of fructan in these tissues, thus also increasing the level of soluble fibre. As outlined herein, fructan has a wide variety of medical, food, and feed applications, meaning that plants of the invention will be a valuable source for the production of fructan. Thus, in another embodiment, the promoter is at least capable of expressing the polypeptide in the seed and/or endosperm. Preferred promoters for preferential expression of an exogenous polynucleotide in seeds (seed-specific expression), particularly in the endosperm of cereal grains, include i) promoters from genes encoding enzymes involved in carbohydrate biosynthesis and accumulation in seeds, and ii) promoters from genes encoding seed storage proteins. Seed specific promoters which are suitable include the *Phaseolus vulgaris* phaseolin promoter (U.S. Pat. No. 5,504,200), the *Brassica* Bce4 promoter (WO 91/13980), the legumin. LeB4 promoter from *Vicia faba* (Baumlein et al., 1992), the wheat low molecular weight glutenin promoter (Colot et al., 1987), the promoter expressing α-amylase in wheat seeds (Stefanov et al., 1991), and the hordein promoter (Brandt et al., 1985), as well as the promoter of a ABA8'OH gene (WO 2007/045040), and promoters which lead to the seed-specific expression in monocots such as maize, barley, wheat, rye, rice and the like. Notable promoters which are suitable are the promoters described in WO 99/16890 such as promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene. In an embodiment, the seed specific promoter is preferentially expressed in defined parts of the seed such as the embryo, cotyledon(s) or most preferably the endosperm. Examples of such specific promoters include, but are not limited to, the pea legumin promoter (Perrin et al., 2000), the bean phytohemagglutnin promoter (Perrin et al., 2000), the conlinin 1 and conlinin 2 promoters for the genes encoding the flax 2S storage proteins (Cheng et al., 2010), the BnGLP promoter of the globulin-like protein gene of *Brassica napus*, and the LPXR promoter of the peroxiredoxin gene from *Linum usitatissimum*. Another example of a promoter which is differentially expressed in the endosperm of developing cereals is the high molecular weight glutenin Bx17 gene promoter.

"Inducible promoters" selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, infection or drought, phytohormones, wounding, or chemicals such as ethanol, jasmonate, salicylic acid, or safeners. As used herein, a "plant stress inducible promoter" is any inducible promoter that is functional in a plant, and hence this term is not limited to promoters derived from a plant.

Suitable inducible promoters for use in expressing the above-described nucleic acids in a plant include promoters that are induced by drought, ABA, salinity, heat or other stresses often associated with water stress. Inducible promoters useful for the invention include the following: the Adh1 promoter which is inducible by hypoxia or cold stress, the Hsp70 promoter which is inducible by heat stress, the PPDK promoter which is inducible by light, the *Zea mays* RAB17 drought inducible promoter induced by ABA (Vilardell, et al., 1990; Busk et al., 1997), the barley drought inducible promoter HvDhn4s (Xiao and Xue, 2001), and the DREB2A and DREB2B promoters induced by dehydration (Liu et al., 1998). Additional drought inducible promoters are disclosed in U.S. Pat. No. 7,314,757.

In an embodiment, the promoter is a sucrose responsive promoter. Examples include promoter elements of genes encoding sucrose synthases and sucrose transporters. For instance, the promoter can be the maize sucrose synthase-I promoter (Yang and Russell, 1990), a rice α-amylase promoter (Huang et al., 1990; Hwang et al., 1998), or the potato patatin promoter (Grierson et al., 1994)

In a preferred embodiment, the plant stress inducible promoter is a drought inducible promoter, examples of which are provided above.

Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from an octopine synthase (ocs) gene or nopaline synthase (nos) gene of *Agrobacterium tumefaciens* (Bevan et al., 1983). Suitable 3' non-translated sequences may also be derived from plant genes such as the ribulose-1,5-bisphosphate carboxylase (ssRUBISCO) gene, although other 3' elements known to those of skill in the art can also be employed.

As the DNA sequence inserted between the transcription initiation site and the start of the coding sequence, i.e., the untranslated 5' leader sequence (5'UTR), can influence gene expression if it is translated as well as transcribed, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi (1987).

Vectors

The present invention includes use of vectors for manipulation or transfer of genetic constructs. By "chimeric vector" is meant a nucleic acid molecule, preferably a DNA molecule derived, for example, from a plasmid, bacteriophage, or plant virus, into which a nucleic acid sequence may be inserted or cloned. A vector preferably is double-stranded DNA and contains one or more unique restriction sites and may be capable of autonomous replication in a defined host cell including a target cell or tissue or a progenitor cell or tissue thereof, or capable of integration into the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., 1985), which may be employed in calcium-sensitive bioluminescence detection; a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably; the nucleic acid construct is stably incorporated into the genome of, for example, the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The level of MYB13 polypeptide can be elevated by increasing the level of expression of a nucleotide sequence that codes for the protein in a plant cell. The level of expression of a gene may be elevated by increasing the copy number per cell, for example by introducing a synthetic genetic construct comprising the coding sequence and a promoter that is operably connected thereto and that is functional in the cell. A plurality of transformants may be selected and screened for those with a favourable level and/or specificity of transgene expression arising from influences of endogenous sequences in the vicinity of the transgene integration site. A favourable level and pattern of transgene expression is one which results in a substantial enhancement of tolerance to stress conditions. Alternatively, a population of mutagenized seed or a population of plants from a breeding program may be screened for individual lines with increased levels of production of a MYB13 polypeptide as defined herein.

Recombinant Cells

Another embodiment of the present invention includes a recombinant cell comprising a host cell transformed with one or more recombinant molecules as defined herein, or progeny cells thereof. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules can remain extrachromosomal or can integrate into one or more sites within a chromosome of the transformed (i.e., recombinant) cell in such a manner that their ability to be expressed is retained. Preferred host cells are plant cells, more preferably the host cell is a cereal cell such as a wheat cell or a barley cell.

Transgenic Plants

The term "plant" as used herein as a noun refers to whole plants and refers to any member of the Kingdom Plantae, but as used as an adjective refers to any substance which is present in, obtained from, derived from, or related to a plant, such as, for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these, particularly stems and/or leaf sheaths having one or more of enhanced levels of fructan, increased level of sucrose:sucrose 1-fructosyltransferase (1-SST) activity, increased level of sucrose:fructan 6-fructosyltransferase (6-SFT) activity, increased level of fructan:fructan 1-fructosyltransferase (1-FFT) activity, increased level of γ-vacuolar processing enzyme (γ-VPE) activity or increased level of fructokinase 1 (FK1) activity, when compared to an isogenic plant lacking the exogenous polynucleotide.

As used herein, the term "seed" refers to "mature seed" of a plant, which is either ready for harvesting or has been harvested from the plant, such as is typically harvested commercially in the field, or as "developing seed" which occurs in a plant after fertilisation and prior to seed dormancy being established and before harvest.

A "transgenic plant" as used herein refers to a plant that contains a nucleic acid construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants". Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

In an embodiment, a transgenic plant of the invention has, preferably when grown under stress conditions such as water-stressed conditions at least some point during flowering and/or anthesis,
 i) an enhanced level of fructan in the stem and/or leaf sheath when compared to an isogenic plant lacking the exogenous polynucleotide,
 ii) an increased level of one or more of sucrose:sucrose 1-fructosyltransferase (1-SST) activity, sucrose:fructan 6-fructosyltransferase (6-SFT) activity, fructan:fructan 1-fructosyltransferase (1-FFT) activity, γ-vacuolar processing enzyme (γ-VPE) activity and fructokinase 1 (FK1) activity in the stem and/or leaf sheath when compared to an isogenic plant lacking the exogenous polynucleotide,
 iii) an increased level of expression in the stem and/or leaf sheath of an endogenous gene(s) encoding one or more of 1-SST, 6-SFT, 1-FFT, γ-VPE and FK1 when compared to an isogenic plant lacking the exogenous polynucleotide,
 iv) a higher grain yield and/or average grain size when compared to an isogenic plant lacking the exogenous polynucleotide,
 v) an increased level of fructan in the seed of the plant when compared to seed from an isogenic plant lacking the exogenous polynucleotide,
 vi) more tolerance to stress conditions than an isogenic plant lacking the exogenous polynucleotide, or
 vii) a combination of two or more of the features of i) to vi).

As the skilled person would appreciate, when the phenotype of a transgenic plant of the invention is compared with an isogenic plant the comparisons are conducted when the plants are grown under the same conditions.

Preferably, the increased levels in ii) and iii) are in the top internode and/or flag leaf, preferably at anthesis.

As used herein, "sucrose:fructan 6-fructosyltransferase", "6-SFT" and variants thereof refers to an enzyme (EC 2.4.1.10) which catalyses the following reaction

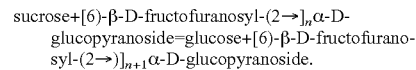

Other names by which this enzyme is known in the art include levansucrase, β-2,6-fructan:D-glucose 1-fructosyltransferase, β-2,6-fructosyltransferase, sucrose 6-fructosyltransferase, sucrose:2,6-β-D-fructan 6-β-D-fructosyltransferase, and sucrose:(2→6)-β-D-fructan 6-β-D-fructosyltransferase. In an embodiment, the sucrose:fructan 6-fructosyltransferase comprises amino acids having a sequence as provided in Accession No. BAB82469, a biologically active fragment thereof, or an amino acid sequence which is at least 30%, more preferably at least 50%, more preferably at least 75%, more preferably at least 90%, and even more preferably at least 95%, identical to amino acids having a sequence as provided in Accession No. BAB82469. In one embodiment, the transgenic plant has at least a 2 fold, more preferably at least a 5 fold, higher level of expression of 6-SFT, preferably in the flag leaf at anthesis, when compared to an isogenic plant lacking the exogenous polynucleotide.

As used herein, "sucrose:sucrose 1-fructosyltransferase", "1-SST" and variants thereof refers to an enzyme (EC 2.4.1.99) which catalyses the following reaction

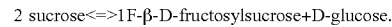

Other names by which this enzyme is known in the art include sucrose 1F-fructosyltransferase, sucrose:sucrose 1F-β-D-fructosyltransferase, and sucrose:sucrose 1(F)-beta-D-fructosyltransferase. In an embodiment, the sucrose:sucrose 1-fructosyltransferase comprises amino acids having a sequence as provided in Accession No. BAB82470, a biologically active fragment thereof, or an amino acid sequence which is at least 30%, more preferably at least 50%, more preferably at least 75%, more preferably at least 90%, and even more preferably at least 95%, identical to amino acids having a sequence as provided in Accession No. BAB82470. In another embodiment, the transgenic plant has at least a 2 fold, more preferably at least a 4 fold, higher level of expression of 1-SST, preferably in the flag leaf at anthesis, compared to an isogenic plant lacking the exogenous polynucleotide.

As used herein, "fructan:fructan 1-fructosyltransferase", "1-FFT" and variants thereof refers to an enzyme (EC 2.4.1.100) which catalyses the following reaction

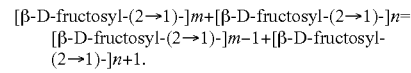

Other names by which this enzyme is known in the art include 1,2-β-D-fructan IF-fructosyltransferase, 1,2-β-D-fructan:1,2-β-D-fructan 1F-β-D-fructosyltransferase and 1,2-β-fructan 1F-fructosyltransferase. In an embodiment, the fructan:fructan 1-fructosyltransferase comprises amino acids having a sequence as provided in Accession No. ACH73191, a biologically active fragment thereof, or an amino acid sequence which is at least 30%, more preferably at least 50%, more preferably at least 75%, more preferably at least 90%, and even more preferably at least 95%, identical to amino acids having a sequence as provided in Accession No. ACH73191. In a further embodiment, the transgenic plant has at least a 2 fold, more preferably at least a 3 fold, higher level of expression of 1-FFT, preferably in the flag leaf at anthesis, when compared to an isogenic plant lacking the exogenous polynucleotide.

As used herein, "γ-vacuolar processing enzyme", "γ-VPE" or variants thereof refer to a cysteine protease typically present in the vacuole of plants. In an embodiment, the γ-vacuolar processing enzyme comprises amino acids having a sequence as provided in SEQ ID NO: 165, a biologically active fragment thereof, or an amino acid sequence which is at least 30%, more preferably at least 50%, more preferably at least 75%, more preferably at least 90%, and even more preferably at least 95%, identical to amino acids having a sequence as provided in SEQ ID NO:165. In a further embodiment, the transgenic plant has at least a 1.5 fold, more preferably at least a 2.5 fold, higher level of expression of γ-vacuolar processing enzyme (γ-VPE), preferably in the flag leaf at anthesis, when compared to an isogenic plant lacking the exogenous polynucleotide.

As used herein, "fructokinase 1", "FK1", or variants thereof refer to an enzyme that catalyzes the transfer of a phosphate group from ATP (the substrate) to fructose. In an embodiment, the fructokinase 1 comprises amino acids having a sequence as provided in SEQ ID NO: 167, a biologically active fragment thereof, or an amino acid sequence which is at least 30%, more preferably at least 50%, more preferably at least 75%, more preferably at least 90%, and even more preferably at least 95%, identical to amino acids having a sequence as provided in SEQ ID NO:167. In a further embodiment, the transgenic plant has at least a 1.5 fold, more preferably at least a 2.5 fold, higher level of expression of fructokinase 1 (FK1), preferably in the flag leaf at anthesis, when compared to an isogenic plant lacking the exogenous polynucleotide.

In yet a further embodiment, the transgenic plant has at least a 2 fold, more preferably at least a 5 fold, higher level of fructan, preferably in the flag leaf at anthesis, when compared to an isogenic plant lacking the exogenous polynucleotide.

In yet a further embodiment, the transgenic plant has at least a 1.2 fold, more preferably at least a 1.4 fold, higher level of fructan, preferably in the top internode at anthesis, when compared to an isogenic plant lacking the exogenous polynucleotide.

In a further embodiment, the transgenic plant has at least a 1%, more preferably at least a 2%, higher grain yield when compared to an isogenic plant lacking the exogenous polynucleotide.

In yet another embodiment, the transgenic plant produces grain which has at least a 1%, more preferably at least a 2%, higher average grain weight when compared to grain from an isogenic plant lacking the exogenous polynucleotide.

In an embodiment, the phenotype is determined using experiments in a glass house (controlled environment), for example such as that used in Example 9. These may be performed under stressed or non-stressed conditions.

As used herein, the term "compared to an isogenic plant" refers to a plant which is isogenic relative to the transgenic plant but without the transgene (exogenous polynucleotide) of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

In an embodiment, the expression levels of the polynucleotide is at least 2 fold, or at least 5 fold, or at least 9 fold higher, than in an isogenic plant lacking the exogenous polynucleotide.

Plants contemplated for use in the practice of the present invention include both monocotyledons and dicotyledons. Target plants include, but are not limited to, the following: cereals (for example, wheat, barley, rye, oats, rice, maize, sorghum and related crops); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape or other Brassicas, mustard, poppy, olives, sunflowers, safflower, flax, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers). In an embodiment, the plant, when in a non-transgenic state, endogenously has the capacity to produce fructans in the stem and/or leaf sheath. Examples include, but are not limited to, wheat, triticale, oats, barley, and plants of the Genera *Lolium, Festuca, Pseudoroegneria, Poa, Psathyrostachys, Haynaldia, Heteranthelium, Phleum, Bromus, Dactylis, Allium* and *Helianthus*. Preferably, the plant is a cereal plant, more preferably wheat, triticale, oats or barley, even more preferably wheat or barley.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. A preferred species of hexaploid wheat is *T. aestivum* ssp *aestivum* (also termed "breadwheat"). Tetraploid wheat includes *T. durum* (also referred to herein as *durum* wheat or *Triticum turgidum* ssp. *durum*), *T. dicoccoides, T. dicoccum, T. polonicum*, and interspecies cross thereof. In addition, the term "wheat" includes potential progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squar-* rosa or *Aegilops tauschii*) for the D genome. Particularly preferred progenitors are those of the A genome, even more preferably the A genome progenitor is *T. monococcum*. A wheat cultivar for use in the present invention may belong to, but is not limited to, any of the above-listed species. Also encompassed are plants that are produced by conventional techniques using *Triticum* sp. as a parent in a sexual cross with a non-*Triticum* species (such as rye [*Secale cereale*]), including but not limited to Triticale.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. This would generally be to modulate the production of at least one protein defined herein in the desired plant or plant organ. Transgenic plant parts include all parts and cells of said plants comprising the transgene such as, for example, cultured tissues, callus and protoplasts.

The term progeny is used to refer to direct progeny of a plant produced by a method of the invention such as inserting an exogenous polynucleotide and generating a plant or crossing two plants one of which has been genetically modified as described herein, as well as indirect progeny such as second, third, fourth etc generation progeny.

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

As used herein, the "other genetic markers" may be any molecules which are linked to a desired trait of a plant. Such markers are well known to those skilled in the art and include molecular markers linked to genes determining traits such disease resistance, yield, plant morphology, grain quality, other dormancy traits such as grain colour, gibberellic acid content in the seed, plant height, flour colour and the like. Examples of such genes are stem-rust resistance genes Sr2 or Sr38, the stripe rust resistance genes Yr10 or Yr17, the nematode resistance genes such as Cre1 and Cre3, alleles at glutenin loci that determine dough strength such as Ax, Bx, Dx, Ay, By and Dy alleles, the Rht genes that determine a semi-dwarf growth habit and therefore lodging resistance.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. No. 4,945,050 and U.S. Pat. No. 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. A particle delivery system suitable for use with the present invention is the helium acceleration PDS-1000/He gun is available from Bio-Rad Laboratories. For the bombardment, immature embryos or derived target cells such as scutella or calli from immature embryos may be arranged on solid culture medium.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. No. 5,451,513, U.S. Pat. No. 5,545,818, U.S. Pat. No. 5,877,402, U.S. Pat. No. 5,932,479, and WO 99/05265.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. No. 5,177,010, U.S. Pat. No. 5,104,310, U.S. Pat. No. 5,004,863, U.S. Pat. No. 5,159,135). Further, the integration of the T-DNA is a relatively precise process resulting in few rearrangements. The region of DNA to be transferred is defined by the border sequences, and intervening DNA is usually inserted into the plant genome.

*Agrobacterium* transformation vectors are capable of replication in *E. coli* as well as *Agrobacterium*, allowing for convenient manipulations as described (Klee et al., Plant DNA Infectious Agents, Hohn and Schell, (editors), Springer-Verlag, New York, (1985): 179-203). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, Breeding Methods for Cultivar Development, J. Wilcox (editor) American Society of Agronomy; Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., Methods for Plant Molecular Biology, Academic Press, San Diego, (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011); *Brassica* (U.S. Pat. No. 5,463,174); peanut (Cheng et al., 1996); and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, WO 97/048814, U.S. Pat. No. 5,589,617, U.S. Pat. No. 6,541,257, and other methods are set out in WO 99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts. The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed "embryo rescue", used in combination with DNA extraction at the three leaf stage and analysis of at least one MYB13 gene or allele that confers a phenotype as defined herein, allows rapid selection of plants carrying the desired trait, which may be nurtured to maturity in the greenhouse or field for subsequent further backcrossing to the recurrent parent.

Any molecular biological technique known in the art can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to alleles of (for example) a MYB13 encoding gene which confers at least one phenotype as defined herein. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al., (2001).

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (M. J. McPherson and S. G Moller (editors), BIOS Scientific Publishers Ltd, Oxford, (2000)). PCR can be performed on cDNA obtained from reverse transcribing mRNA isolated from plant cells expressing a MYB13 gene or allele which confers at least one phenotype as defined herein. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al., (supra) and Sambrook et al., (supra). Sequencing can be carried out by any suitable method, for example, dideoxy sequencing, chemical sequencing or variations thereof. Direct sequencing has the advantage of determining variation in any base pair of a particular Sequence.

Stress Conditions

As used herein, the term "stress conditions" refers to any environmental factor(s) that prevents a plant fulfilling its genetic potential. The stress may be constant or transient (for example, at least 7 or at least 14 or at least 21 days). Examples of stress conditions include, but are not limited to, water stress (drought), salt stress, heat stress, cold stress, freezing stress, radiation stress, oxidative stress, heavy metal tolerance, disease such as a fungal infection, a bacterial infection, a viral infection, or a combination of two or more thereof. In a preferred embodiment, the stress condition is at least water stress (in some instances combined with heat stress). "Drought" is defined herein as the limited availability of water to the plants such that the grain yield in the field is less than 2.5 tonnes/hectare, where water stress is the main limitation to yield. In Australia, this corresponds to an annual rainfall of about 350 mm per year, although the timing of rainfall and therefore water availability to the crop during the season is also important, both prior to planting, during growth and particularly during the grain-filling period. However, it would be appreciated that even with rainfall of greater than 350 mm per year, some extent of water stress to growth and yield can and does occur, even when grain yields of about 6-7 tonnes/hectare are achieved.

As used herein, the phrase "more tolerance to stress conditions" or variations thereof are considered relative terms. A transgenic plant with enhanced tolerance to stress conditions is defined as a plant better survival, growth and/or yield characteristics (such as greater shoot and/or root biomass, greater root length, better water use efficiency and/or greater seed yield) when compared to an isogenic plant lacking the exogenous polynucleotide.

As used herein, "relative yield index" is defined as yield of transgenic/yield of non-transgenic under conditions which are water-limiting at least in part. In fact, essentially all wheat grown in Australia under non-irrigated conditions is water limited. The average wheat yield in Australia is 2.5 tonnes/hectare, while wheat can produce 15 tonne/ha. The present invention will help bridge this gap.

In one embodiment, a transgenic plant of the invention has "enhanced tolerance to water stress" (also referred to as "enhanced tolerance to drought") when compared to an isogenic plant lacking the exogenous polynucleotide. Water stress (also referred to as drought or water limitation) refers to a decrease in water availability to a plant that, especially when prolonged (for example for more than 14 days) but also for shorter periods of time (for example for 2-14 days) in particular if combined with another stress such as heat stress (>32° C. for cool-season cereals and grass species), can cause damage to the plant or prevent its successful growth (e.g., limiting plant growth or seed yield). "Drought tolerance" or "tolerance to water stress" is a trait of a plant to survive under drought conditions over prolonged periods of time without exhibiting substantial physiological or physical deterioration, or to exhibit greater survival or less deterioration than a wild-type (control) plant. "Increased drought tolerance" of a plant is measured relative to a reference or control plant, and is a trait of the plant to survive or have improved probability of surviving under drought conditions over prolonged periods of time, without exhibiting the same degree of physiological or physical deterioration relative to the reference or control plant grown under similar drought conditions. Typically, when a transgenic plant comprising an exogenous polynucleotide in its genome exhibits increased drought tolerance relative to a reference or control plant, the reference or control plant does not comprise in its genome the exogenous polynucleotide.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color, leaf area size, biomass, dry matter or leaf senescence. Other techniques for evaluating drought tolerance include measuring chlorophyll fluorescence, photosynthetic rates and gas exchange rates. The Examples below describe some representative protocols and techniques for simulating drought conditions and/or evaluating drought tolerance.

In another embodiment, a transgenic plant of the invention has. "enhanced tolerance to saline and/or sodic soils" when compared to an isogenic plant lacking the exogenous polynucleotide. A saline soil is defined as having a high concentration of soluble salts, high enough to affect plant growth. Salt concentration in a soil is measured in terms of its electrical conductivity. As used herein a "saline soil" has an $EC_e$ of at least 1 dS/m, more preferably at least 2 dS/m, more preferably at least 3 dS/m, and even more preferably at least 4 dS/m. $EC_e$ is the electrical conductivity of the 'saturated paste extract', that is, of the solution extracted from a soil sample after being mixed with sufficient water to produce a saturated paste. Sodic soils have a low concentration of soluble salts, but a high percent of exchangeable Na; that is, Na⁺ forms a high percent of all cations bound to the negative charges on the clay particles that make up the soil complex. Sodicity is defined in terms of the threshold ESP (exchangable sodium percentage) that causes degradation of soil structure. As used herein a "sodic soil" has an ESP greater than 5, more preferably an ESP greater than 7, more preferably an ESP greater than 9, more preferably an ESP greater than 11, more preferably an ESP greater than 13, and even more preferably an ESP greater than 15. A plant with enhanced tolerance to saline and/or sodic soils is defined as a plant which is more capable of growing, and/or reproducing, in saline and/or sodic conditions when compared to a plant with the same, or similar, genotype but lacking the exogenous polynucleotide.

In a further embodiment, a transgenic plant of the invention has enhanced tolerance to an infection such as by a fungus, bacteria or virus. In a preferred embodiment, a transgenic plant of the invention has enhanced tolerance to a fungal infection. Examples of such fungal infections include, but are not limited to, those by *Fusarium graminearum* (which causes head blight), *Erysiphe graminis* f sp. *tritici* (which causes powdery mildew), *Bipolaris sorokiniana* (which causes spot blotch), *Puccinia graminis* f sp. *tritici* (which causes stem rust), *Puccinia striiformis* (which causes stripe rust) and *Puccinia recondita* f sp. *tritici* (which causes leaf rust).

In an embodiment, when grown under stress conditions, for example water stress, a plant of the invention has a greater seed yield when compared to an isogenic plant lacking the exogenous polynucleotide. This many be assessed, for example, by growing plants in a controlled environment, such as a glasshouse, with a defined amount of water and plastic covering the soil to prevent water loss through evaporation. In an embodiment, water stress is commenced at the early booting stage with plants of the invention having a greater grain (seed) yield per plant than the control plants.

In a further embodiment, when grown under stress conditions, for example water stress, the expression of at least one endogenous gene in a plant of the invention is enhanced when compared to an isogenic plant lacking the exogenous polynucleotide, wherein the endogenous gene encodes; 1-SST, 6-SFT, 1-FFT, γ-VPE or FK1. Expression of these genes can be detected using standard procedures in the art, for example RT-PCR using the primers outlined herein.

Tilling

Plants of the invention can be produced using the process known as TILLING (Targeting Induced Local Lesions IN Genomes) for detection of mutations in genes other than the exogenous polynucleotide. In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide, polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools' of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Plant/Grain Processing

Grain/seed of the invention, preferably cereal grain and more preferably wheat grain, or other plant parts of the invention, each of which comprise increased levels of fructan relative to wild-type grain or other plant parts, can be processed to produce a food ingredient, food or non-food product using any technique known in the art, or to produce isolated fructan.

Applications of fructans are diverse and include medical, food, and feed applications, as well as a raw material for the production of industrial polymers and high-fructose syrup. Regardless of size, fructose polymers are not metabolized by humans and animals. Fructans can enhance animal health and performance because they are selectively fermented by beneficial organisms such as *Bifidibacterium* in the large intestine of animals including humans, at the expense of pathogenic organisms such as *E. coli* and *Salmonella*, resulting in altered fatty acid profiles, increased nutrient absorption, and a reduction of blood cholesterol. Also, fructans have a sweet taste and are increasingly used as low-calorie sweeteners and as functional food ingredients.

In one embodiment, the product is whole grain flour such as, for example, an ultrafine-milled whole grain flour, or a flour made from about 100% of the grain. The whole grain flour includes a refined flour constituent (refined flour or refined flour) and a coarse fraction (an ultrafine-milled coarse fraction), comprising the increased level of fructan.

Refined flour may be flour which is prepared, for example, by grinding and bolting cleaned grain such as wheat or barley grain. The particle size of refined flour is described as flour in which not less than 98% passes through a cloth having openings not larger than those of woven wire cloth designated "212 micrometers (U.S. Wire 70)". The coarse fraction includes at least one of: bran and germ. For instance, the germ is an embryonic plant found within the grain kernel. The germ includes lipids, fiber, vitamins, protein, minerals and phytonutrients, such as flavonoids. The bran includes several cell layers and has a significant amount of lipids, fiber, vitamins, protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and therefore is typically removed with the bran and germ during the milling process. The aleurone layer contains proteins, vitamins and phytonutrients, such as ferulic acid.

Further, the coarse fraction may be blended with the refined flour constituent. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.—ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. Stabilization is a process that uses steam, heat, radiation, or other treatments to inactivate the enzymes found in the bran and germ layer. Flour that has been stabilized retains its cooking characteristics and has a longer shelf life.

In additional embodiments, the whole grain flour, the coarse fraction, the refined flour or isolated fructan may be a component (ingredient) of a food product and may be used to increase the fructan level of the food product relative to the use of the corresponding wild-type ingredient. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In alternative embodiments, the whole grain flour, refined flour, coarse fraction or isolated fructan may be a component of a nutritional supplement. For instance, the nutritional supplement may be a product that is added to the diet containing one or more additional ingredients, typically including: vitamins, minerals, herbs, amino acids, enzymes, antioxidants, herbs, spices, probiotics, extracts, prebiotics and fiber. The whole grain flour, refined flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. The supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour or a multi-grain coarse fraction. For example, bran and germ from one type of grain may be ground and blended with ground endosperm or whole grain cereal flour of another type of cereal. Alternatively bran and germ of one type of grain may be ground and blended with ground endosperm or whole grain flour of another type of grain. It is contemplated that the present invention encompasses mixing any combination of one or more of bran, germ, endosperm, and whole grain flour of one or more grains. This multi-grain approach may be used to make custom flour and capitalize on the qualities and nutritional contents of multiple types of cereal grains to make one flour.

It is contemplated that the whole grain flour, coarse fraction and/or grain products of the present invention may be produced by any milling process known in the art. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. After grinding, the grain is discharged and conveyed to a sifter. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

Malting

A malt-based beverage, provided by the present invention involves alcohol beverages (including distilled beverages) and non-alcohol beverages that are produced by using malt as a part or whole of their starting material. Examples include beer, happoshu (low-malt beer beverage), whisky, low-alcohol malt-based beverages (e.g., malt-based beverages containing less than 1% of alcohols), and non-alcohol beverages.

Malting is a process of controlled steeping and germination followed by drying of the grain such as barley and wheat grain. This sequence of events is important for the synthesis of numerous enzymes that cause grain modification, a process that principally depolymerizes the dead endosperm cell walls and mobilizes the grain nutrients. In the subsequent drying process, flavour and colour are produced due to chemical browning reactions. Although the primary use of malt is for beverage production, it can also be utilized in other industrial processes, for example as an enzyme source in the baking industry, or as a flavouring and colouring agent in the food industry, for example as malt or as a malt flour, or indirectly as a malt syrup, etc.

In one embodiment, the present invention relates to methods of producing a malt composition. The method preferably comprises the steps of:
  (i) providing grain, such as barley or wheat grain, of the invention,
  (ii) steeping said grain,
  (iii) germinating the steeped grains under predetermined conditions and
  (iv) drying said germinated grains.

For example, the malt may be produced by any of the methods described in Hoseney (Principles of Cereal Science and Technology, Second Edition, 1994: American Association of Cereal. Chemists, St. Paul, Minn.). However, any other suitable method for producing malt may also be used with the present invention, such as methods for production of specialty malts, including, but limited to, methods of roasting the malt.

Malt is mainly used for brewing beer, but also for the production of distilled spirits. Brewing comprises wort production, main and secondary fermentations and post-treatment. First the malt is milled, stirred into water and heated. During this "mashing", the enzymes activated in the malting degrade the starch of the kernel into fermentable sugars. The produced wort is clarified, yeast is added, the mixture is fermented and a post-treatment is performed.

Fructan

Plants of the invention can be used for the production of fructan. Such production from grain which can be readily produced in broadacre agriculture will be cost-effective relative to existing methods of fructan production, for example, involving the extraction of inulins from chicory.

Fructans are polymers of fructose which are synthesized from sucrose and used as storage or reserve carbohydrates by many plants. They consist of fructosyl residues polymerized to sucrose, and therefore comprise fructosyl units in addition to one glucose unit. In view of this composition, they are highly soluble in water. The linkages between the fructosyl-residues are either exclusively of the β(1-2) type forming a linear molecule (inulin) in which the fructosyl residues are attached to the fructosyl residue of the sucrose starter, or of the β(2-6) type (levan), or both linkage types occur in branched fructans (graminans). Graminans which consist of β(2-6)-linked fructose units with β(1-2) branches and are therefore more complex structures can also be present in cereals, and can be mixed with levans.

Fructans are non-starch carbohydrates with potentially beneficial effects as a food ingredient on human health (Tungland and Meyer, 2002; Ritsema and Smeekens, 2003). The human digestive enzymes α-glucosidase, maltase, isomaltase and sucrase are not able to hydrolyse fructans because of the β-configuration of the fructan linkages. Furthermore, humans and other mammals lack the fructan exohydrolase enzymes that break down fructans and therefore dietary fructans avoid digestion in the small intestine and reach the large intestine intact. However, bacteria there are able to ferment fructans and thereby utilize them as, for example, an energy or carbon source for growth and production of short-chain fatty acids (SCFA). Dietary fructans therefore are able to stimulate the growth of beneficial bacteria such as bifidobacteria in the colon, which aids in prevention of bowel disorders such as constipation and infection by pathogenic gut bacteria. Dietary fructan also enhances nutrient absorption from diets, particularly calcium and iron, possibly via production of SCFA which in turn reduce luminal pH and modify calcium speciation and hence solubility, or exert a direct effect on the mucosal transport pathway, thereby improving the mineralization of bone and reducing the risk of iron deficiency anaemia. In addition, a high-fructan diet can improve the health of patients with diabetes and reduce the risk of colonic cancers by suppressing aberrant crypt foci which are precursors of colon cancer (Kaur and Gupta, 2002).

Large scale extraction of fructan can be achieved by milling the grain to wholemeal flour and then extracting the total sugars including fructans from the flour into water. This may be done at ambient temperature and the mixture then centrifuged or filtered. The supernatant is then heated to about 80° C. and centrifuged to remove proteins, then dried down. Alternatively, the extraction of flour can be done using 80% ethanol, with subsequent phase separation using water/chloroform mixtures, and the aqueous phase containing sugars and fructan dried and redissolved in water. Sucrose in the extract prepared either way may be removed enzymatically by the addition of α-glucosidase, and then hexoses (monosaccharides) removed by gel filtration to produce fructan fractions of various sizes. This would produce a fructan enriched fraction of at least 80% fructan.

EXAMPLES

Example 1

Materials and Methods

Plant Materials and Growth Conditions

Samples from Field Experiments

Recombinant inbred SB lines of *Triticum aestivum* L from the Seri M82 and Babax cross were grown under rain-fed conditions (Xue et al., 2008b). Top two internodes (peduncle and penultimate internode) with leaf sheath attached were harvested at anthesis for the measurement of Water soluble carbohydrates (WSC) and fructan concentrations and expression analysis. Each sample consisted of 5 stems randomly picked from several locations of each plot.

Samples from Controlled Environmental Room Experiments

Wheat plants were grown in a controlled-environment room under night/day conditions of 16-h light (500 μmol $m^{-2}s^{-1}$), 14/18° C. and 90/60% relative humidity (Kam et al., 2008). Peduncle, penultimate internodes and flag leaves were harvested for expression analysis.

Sugar Treatment

Shoots from 5-week-old wheat plants (cv. Babax), that were pre-adapted in the dark for 13 h, were cut just above the soil and were treated in a solution of 10 mM potassium phosphate (pH 6.5) with 50 mM sugar (sucrose or glucose) or without sugar (control) in the dark for 8 h. 8-10 fully expanded new leaves (1 leaf per tiller) were harvested after treatment and pooled as one biological sample.

Measurements of Water Soluble Carbohydrate Levels

WSC were extracted as described previously (Xue et al., 2008b). WSC level in the extracts was measured using the modified anthrone procedure (Xue et al., 2009). The WSC composition (sucrose, glucose, fructose and fructans) in the extracts was determined by HPAEC (Ruuska et al., 2006).

Correlated Expression Analysis of Affymetrix Wheat Genome Array Data

Affymetrix wheat genome array GSE9767 data for genotypic variation in gene expression among 16 samples of top two internodes at anthesis from 8 recombinant inbred SB lines with two field replicates were reported previously (Xue et al., 2008b) and were used for correlation analysis. The Affymetrix wheat genome array contains 61,127 probe sets. Raw Affymetrix array data were normalized using robust multiarray average (Irizarry et al., 2003). The normalised log values were converted to non-log values in Microsoft Excel, which were used for identification of regulatory genes that were correlated in expression with fructosyltransferases as well as stem WSC and fructan concentrations, using Pearson correlation coefficient.

Total RNA Extraction

Total RNA was isolated from samples using Plant RNA Reagent (Invitrogen, California, USA), according to the manufacturer's instruction. RNA was further purified through a Qiagen RNeasy column (Qiagen, Australia) after pre-treatment with RNase-free DNase I (Xue and Loveridge, 2004).

Isolation of the Full-Length cDNAs of TaMYB13-1, TaMYB13-2 and TaMYB13-3

Wheat cDNAs were synthesised from poly (A)+ mRNA prepared from wheat cv Babax stems. Wheat MYB cDNAs were isolated using 3'-RACE with a sense primer (MYBS1, 5'-TTCCTCGAGTCAAGTGGCTCT (SEQ ID NO:119)), corresponding to the 5'-untranslated region of an EST (CJ715544), and an anchor primer supplied in the RACE kit (Roche Diagnostics, Mannheim, Germany). The PCR-amplified products were cloned into pGEM-T (Promega) and sequenced using a BigDye terminator cycle sequencing kit (Applied Biosystems, Foster City, USA). The cDNA sequence of each TaMYB13 transcript was derived from sequencing 2-4 clones.

Isolation of Ta6-SFT Promoter Sequences

Wheat 6-SFT promoters were isolated from genomic DNA of SB169 line using inverse PCR (Triglia, 2000). Inverse PCR primers were designed based on the 5'-region sequence of a Ta6-SFT cDNA (AB029887). Two promoter sequences were obtained [Ta6-SFT1 (HQ738530) and Ta6-SFT2 (HQ738531), 851-bp and 1001-bp fragments upstream of the translation start codon, respectively].

Expression Analysis Using Quantitative RT-PCR

The transcript levels of wheat genes were quantified from cDNA samples synthesised from DNase I-treated total RNA using real-time PCR with an ABI Prism 7900 sequence detection system (Applied Biosystems) and SYBR Green PCR Master Mix (Applied Biosystems) according to the manufacturer's instructions. An external reference mRNA (626 nt) in vitro transcribed from a bovine cDNA (CF767388) (Xue et al., 2006a) was added to each RNA sample before cDNA synthesis. The sequences of primer pairs used for real-time PCR are listed in Table 2. The transcript-specific primers for three TaMYB13 genes are illustrated in FIG. 1. Primer pairs for fructosyltransferase genes and internal and external control genes were reported previously (Xue et al., 2006ab, 2008a; Stephenson et al., 2007).

The mRNA levels of TaRP15 and TaRPII36 internal reference genes were almost the same in the stem among samples of the 16 SB lines, as judged using the external reference gene (CF767388).

Wheat RNA polymerases (TaRPI136 and TaRP15) were selected as internal reference genes for calculation of relative transcript levels of the genes under study (Xue et al., 2008a). The PCR efficiency of each primer pair was determined by a dilution series of samples. The determination of the specificity of real-time PCR amplification and relative quantitation of mRNA levels were as described by Shaw et al. (2009).

Constructs pTaMYB13-CELD was constructed by translational fusion of the coding region sequence of TaMYB13-1 (correctly spliced form) to the N-terminus of the 6xHis-tagged CELD reporter (Xue, 2005). Cel1) encodes a *Neocallimastix patriciarum* cellulase (Xue et al., 1992). pHvD8TaMYB13R (FIG. 2a) was constructed by replacing uidA in pDhn8sGUSR (Xiao and Xue, 2001) with the coding region of correctly spliced TaMYB13-1. Fructosyltransferase promoter-driven xynA reporters (FIG. 2a) were constructed by replacing the maize Ubi1 promoter in pUbiSXR plasmid (Vickers et al., 2003) with the PCR-amplified fragments of Ta1-SST (FJ228689), Ta6-SFT1 (HQ738530) and Hv6-SFT (AJ306962) promoters. The second catalytic domain of *Neocallimastix patriciarum* xylanase A (XYNA) was used as a reporter (Xue et al., 1995). Ta1-SST promoter was isolated from genomic DNA of wheat genotype SB169 by PCR amplification. The 2199-bp Ta1-SST promoter fragment immediately upstream of translation start codon was inserted upstream of the xynA coding sequence to create Ta1-SSTSXR construct. Ta6-SFT1SXR was constructed by inserting a 689-bp fragment of Ta6-SFT1 promoter immediately upstream of translational start codon as for Ta1-SSTSXR. Hv6-SFT promoter was isolated from genomic DNA of *Hordeum vulgare* L. genotype Sahara by PCR amplification. The 1473-bp Hv6-SFT promoter fragment immediately upstream of translation start codon was inserted upstream of the xynA coding sequence. The nucleotide sequences of the constructs were checked by sequencing. pSP72 was used as a vector for these expression constructs.

TABLE 2

Primers for real-time PCR analysis of T aestivum and external control genes.

| Gene name | GanBank or TC # | Forward primer Name | Sequence | Reverse primer Name | Sequence |
|---|---|---|---|---|---|
| TaMYB13-1 | See FIG. 1 | TaMYB13S5 [c] | 5'-AGTTGCACCGGGTGGTTT (SEQ ID NO: 93) | TaMYB13R6 [c] | 5'-CCGTCCGGTTAAGACCTGA (SEQ ID NO: 106) |
| | | TaMYB13S5 [d] | 5'-AGTTGCACCGGGTGGTTT (SEQ ID NO: 94) | TaMYB13R8 [d] | 5'-GCCACCTTGCAAACCTGAC (SEQ ID NO: 107) |
| TaMYB13-2 | See FIG. 1 | TaMYB13S6 [c] | 5'-GGTTTCCGGAAGGGACCA (SEQ ID NO: 95) | TaMYB13R9 [c] | 5'-CCGTCCGGTTGAGACCTGA (SEQ ID NO: 108) |
| | | TaMYB13S6 [d] | 5'-GGTTTCCGGAAGGGACCA (SEQ ID NO: 96) | TaMYB13R8 [d] | 5'-GCCACCTTGCAAACCTGAC (SEQ ID NO: 109) |
| TaMYB13-3 | See FIG. 1 | TaMYB13S7 [c] | 5'-GGAGGAAGCAGTTGCACCC (SEQ ID NO: 97) | TaMYB13R9 [c] | 5'-CCGTCCGGTTGAGACCTGA (SEQ ID NO: 110) |
| | | TaMYB13S7 [d] | 5'-GGAGGAAGCAGTTGCACCC (SEQ ID NO: 98) | TaMYB13R8 [d] | 5'-GCCACCTTGCAAACCTGAC (SEQ ID NO: 111) |
| Ta1-SST1 [a] | 248548 | TaSSF1F | 5'-GGTCTTCGGACGCACTTCTG (SEQ ID NO: 99) | TaSSF1R | 5'-CGCCACATCGGTAGCATGT (SEQ ID NO: 112) |
| Ta1-SST2 [a] | 264622 | TaSSF2cF13 | 5'-ACAACGCCACCGGCACTA (SEQ ID NO: 100) | TaSSF2cR14 | 5'-GACGAGTCCATATCATGCACTACAA (SEQ ID NO: 113) |
| Ta6-SFT1 [a] | 251085 | TaSFF1bF13 | 5'-GAGATGGACTCAGCGCACAA (SEQ ID NO: 101) | TaSFF1bR14 | 5'-GCCTTCCTTGGTGAGCTTCTTT (SEQ ID NO: 114) |
| Ta6-SFT2 [a] | 251720 | TaSFF2F15 | 5'-CATATGTAAACGATTCCGCACAG (SEQ ID NO: 102) | TaSFF2R16 | 5'-GCAGAACATGACCCAAGGATAGA (SEQ ID NO: 115) |
| TaRPII36 [a] | 235230 | TaRPII36fF3 | 5'-ACGTATTAACCAAGAACTCATGGAGAC (SEQ ID NO: 103) | TaRPII36fR4 | 5'-TCAAATACTTTTGTAGGGCTGCTCTC (SEQ ID NO: 116) |
| TaRP15 [a] | 265122 | TaRP15F5 | 5'-GCACACGTGCTTTGCAGATAAG (SEQ ID NO: 104) | TaRP15R6 | 5'-GCCCTCAAGCTCAACCATAACT (SEQ ID NO: 117) |
| Bovine cDNA [b] | CF76738 | C12B07F | 5'-GAACTGTCTGGATTGTCCCATCA (SEQ ID NO: 105) | C12B07R | 5'-ACAGTAGGCCCACACCAATGTAC (SEQ ID NO: 118) |

[a] Xue et al., 2008b
[b] Xue et al., 2006a
[c] Primers specific for correctly spliced forms
[d] Primers specific for unspliced forms The promoter truncation constructs, Ta6-SFT1SXR-ΔS1S2 and Ta1-SSTSXR-ΔS1, were produced by PCR amplification of Ta6-SFT1SXR and Ta1-SSTSXR reporter gene cassettes using an anti-sense primer (SP72R, 5'-CTGAGAGTGCACCATATGGACATA (SEQ ID NO:120) in pSP72 vector, 112-bp downstream of rice rbcS 3') and a sense primer (Ta6-SFT1-ΔS1S2F, GGATAGTGTTGAACATACGGTTT (SEQ ID NO:121) or Ta1-SST-ΔS1F, 5'-TGTCGTATAATGCATTGTTTCTTACCGAACA (SEQ ID NO:122)) at the desired promoter position as specified in FIG. 2b. A point mutation construct (Ta6-SFT1SXR-mS1) was produced by PCR amplification of Ta6-SFT1SXR using SP72R and Ta6-SFT1mS1F (5'-CCGACAACTGTTTTGTGGTGAATTACAACCGATTTAACACAGTCTTGACCG TGCA (SEQ ID NO:123), the mutated bases are underlined), where the first TaMYB13-binding site (S1, TGTTAGGTTCGGTT (SEQ ID NO:124)) of Ta6-SFT1 was mutated to (TGTTA<u>AAA</u>TCGGTT (SEQ ID NO:125), which is incorporated in the reverse complementary sequence of Ta6-SFT1mS1F). Ta1-SSTSXR-ΔS1mS2 point mutation construct was produced by PCR amplification of Ta1-SSTSXR using SP72R and Ta1-SSTmS2F (5'-TGTCGTATAATGCATTGTTTCTTTGGAACATGCATGCGTCCCATGCAA (SEQ ID NO:126)), where the second TaMYB13-binding site (S2, ATGTTCGGTAA (SEQ ID NO:127)) of Ta1-SST in Ta1-SSTSXR-ΔS1 was mutated to (ATGTTCC<u>AAAA</u> (SEQ ID NO:128) in the reverse complementary sequence of Ta1-SSTmS2F). Ta6-SFT1SXR-SS was a construct with the addition of a duplicated Hv6-SFT S1 (TATGTTAGGTAC (SEQ ID NO:129)) to Ta6-SFT1SXR-ΔS1S2 and was produced by PCR amplification of Ta6-SFT1SXR using SP72R and Ta6-SFT1-SSF (5'-CCGC<u>TATGTTAGGTAC</u>AT<u>TATGTTAGGTAC</u>GGATAGTGTTGAACATACGGTTT (SEQ ID NO:130)).

In Vitro Random DNA Binding Site Selection

The standard procedure for in vitro binding site selection using Ni-NTA magnetic beads as an affinity matrix was used for selection of TaMYB13 binding sites (Xue, 2005), which used TaMYB13-1 fused with 6xHis-tagged CELD and a biotin-labelled double-stranded oligonucleotide containing a 30-nt random sequence [5'-GGATCCCTCGAGCTGCAGC(N30)GCTAGCCGATCGGAGCTCGG] (SEQ ID NO:131). The TaMYB13-selected oligonucleotides after the fifth round selection were cloned for sequence analysis (Xue, 2005).

DNA-Binding Activity Assays

The DNA-binding activity of TaMYB13-CELD was measured as described previously (Xue, 2002a) using streptavidin-coated 96-well plate and binding/washing buffer (25 mM HEPES/KOH, pH 7.0, 50 mM KCl, 0.2 mM EDTA and 0.5 mM DTT) containing 0.15 µg µl$^{-1}$ shared herring sperm DNA, 0.3 mg ml$^{-1}$ bovine, serum albumin, 10% glycerol and 0.025% Nonidet P-40. 40,000 fluorescent units h$^{-1}$ of the CELD activity of TaMYB13-CELD protein and 2 pmol of biotinylated probes were used per assay. The cellulase activity of TaMYB13-CELD proteins bound to immobilised biotinylated probes was assayed by incubation in 100 μl of the CELD substrate solution [1 mM methylumbelliferyl β-D-cellobioside (MUC) in 50 mM Na-citrate buffer, pH 6.0] at 40° C. for 3 h. A biotin-labelled double-stranded oligonucleotide without a TaMYB13 binding site was used as a control of background activity.

Binding site competition assays were as described by Xue (2002). An unlabelled doubled-stranded oligonucleotide (5 pmol) was added to the protein-DNA binding reaction as a competitor to a biotin-labelled probe (2 pmol). Relative TaMYB13 binding activity was expressed as fluorescence units (FU) of methylumbelliferyl group generated from MUC hydrolysis by TaMYB13-CELD that bound to an immobilised biotin-labelled probe after 3-h incubation of cellulase assay.

Transactivation Assays

Transactivation assays were described previously (Xue, 2003). The effector gene was co-introduced into the fully expanded new leaves of wheat (cv. Bobwhite) using a particle inflow gun with a xynA reporter gene driven by a fructosyltransferase promoter. A β-glucuronidase (GUS+) reporter driven by maize Ubi1 promoter, as described by Vickers et al. (2003), was also co-bombarded for normalisation of transformation efficiency between assays. The bombarded leaves were kept at room temperature under laboratory fluorescent lights for 30 h. Xylanase and GUS activities were assayed as described previously (Xue, 2002b; Vickers et al., 2003). Leaf tissues bombarded with vector (pSP72)-coated gold particles were used as a control of background activity.

Transformation of Wheat with TaMYB13 Construct

TaMYB13-1 expression construct (Hv6-SFT:TaMYB13-1:rice rbcS 3') was made by cloning the coding region of TaMYB13-1 in the pSP72 vector, between the barley Hv6-SFT promoter (Nagaraj et al., 2001), using the construction method as described by Xiao and Xue (2001), followed by nucleotide sequencing. The inventors used the selectable marker cassette containing rice act1:bar:nos 3' to co-transform Bobwhite wheat plants. Both cassettes were PCR-amplified and used for transformation of immature Bobwhite SH 98 26 embryos using the particle bombardment as described by Pellegrineschi et al. (2002). Transgenic plants were selected with the herbicide phospinothricin and grown in a controlled environment as described above. The presence of the HvSFT:TaMYB13-1:rice rbcS 3' cassette was verified by real-time PCR on genomic DNA as described above.

Affymetrix Expression Analysis of Transgenic Lines Over-Expressing TaMYB13 for Identification of Target Genes of TaMYB13

RNA from the flag leaves and top internode of transgenic plants and non-transformed Bobwhite grown in controlled environment was extracted and processed as described above. RNA-quality check, cRNA preparation, labelling, hybridization, and data acquisition of Affymetrix wheat GeneChips were performed by the microarray service at the Australian Genome Research Facility (Melbourne, Australia). The Affymetrix GeneChip data were normalized using GeneChip robust multiarray average (GC-RMA), developed by Wu et al. (2004), using the Affymetrix package within Bioconductor, running within the R statistical programming environment (http://www.r-project.org/). Probesets with expression levels below 100 in both the control plants as well as the transgenic lines were discarded, as were probesets that had a differential expression with a p-value below P=0.05. The inventors selected probesets that had an increase or decrease in hybridisation signals in TaMYB13 overexpressing transgenic lines at least two-fold compared to the control plants.

Determination of the Genomic DNA Sequence of TaMYB13 Target Genes

The sequences of the Affymetrix probes for the target genes were used as query sequences to BLAST the genothic sequence of wheat from the cerealsDB (http://www.cerealsdb.uk.net). The retrieved sequence was subsequently used in a new BLAST search to retrieve additional sequences. The final retrieved genomic sequence contigs were cross checked with EST data from NCBI (http://blast.ncbi.nlm.nih.gov/Blast.cgi) and the DFCI *Triticum aestivum* Gene Index (http://compbio.dfci.harvard.edu/cgi-bin/tgi/gimain.pl?gudb=wheat). Where possible, the BLAST search was continued until at least 1000 bp upstream of the ATG was determined.

Example 2

Identification of Regulatory Genes Positively Associated with Stem WSC and Fructan Concentrations and Correlated with Fructosyltransferase Expression To identify crucial genes that underlie the high WSC trait, the inventors performed a search for regulatory genes that were correlated in expression with the stem WSC and fructan concentrations as well as with 1-SST and 6-SFT transcript levels among SB lines, using Affymetrix dataset reported previously (Xue et al., 2008b). Among a number of correlated Affymetrix probe sets encoding regulatory genes, Ta.12834.1.S1_s_at, which represents a group of MYB ESTs, showed marked differential expression with a maximum 3.5-fold difference in mRNA level among the stem samples from SB lines (data not shown). The mRNA level of the Ta.12834.1.S1_s_at probe set was highly correlated with stem WSC (r=0.84, P<0.01) as well as fructan (r=0.68, P<0.01) concentrations among field-grown SB lines (FIG. 3a). Expression correlation analysis between Ta.12834.1.S1_s_at and three fructosyltransferase genes (Ta6-SFT1, Ta6-SFT2, and Ta1-SST1) present in the Affymetrix wheat genome array also showed highly positive correlations among 16 samples from 8 SB lines (FIG. 3). This data indicates that the MYB genes represented by Ta.12834.1.S1_s_at are candidate transcription factors that potentially control the expression of wheat fructosyltransferase genes.

Example 3

Molecular Features of TaMYB13 Genes

To further investigate their role in regulation of fructan synthesis, the inventors isolated the full-length cDNAs of MYB genes represented by Ta.12834.1.S1_S_at through 3'-RACE. Three highly homologous MYB genes were isolated from *T. aestivum* (FIGS. 1 and 4), designated TaMYB13-1, TaMYB13-2 and TaMYB13-3. The amino acid sequences of three TaMYB13 proteins share 91-96% identity each other and are 100% identical in the MYB domain. Each of these MYB genes had two transcript forms (FIG. 1). The short-form transcripts of these genes encode proteins possessing a R2R3-MYB domain (FIG. 5a). The long-form transcripts of three TaMYB13 genes contain an unspliced intron (FIG. 1), which leads to a translation stop before the end of the MYB R2 motif (FIG. 4). It is likely that these long-form transcripts do not encode a functional MYB protein. All three TaMYB13 genes match with the Affymetrix Ta.12834.1.S1_s_at probe set.

A sequence search for a TaMYB13 homologue in barley identified a homologous protein (designated HvMYB13) (FIG. 5) and shares 86% amino acid sequence identity with TaMYB13-1. An unspliced intron form of HvMYB13 also exists in barley (data not shown). The closest homologues of TaMYB13 in model plant species (*Arabidopsis* and rice) identified from the Pant Transcription Factor database (Riario-PachOn et al., 2007; Perez-Rodriguez et al., 2010) are *Arabidopsis* MYB48 (AtMYB48) and MYB59 (AtMYB59) and three unnamed rice MYB genes (LOC_Os11g47460.1, LOC_Os12g37970.1 and LOC_Os01g74410.1), which share the overall amino acid identity between 41 and 45% with that of TaMYB13-1 (FIG. 6). However, sequence conservation at the MYB domain is very high (FIG. 5b).

Example 4

TaMYB13 Shares the Same Expression Profile with 1-SST and 6-SFT

Relative transcript abundance of TaMYB13-1, TaMYB13-2 and TaMYB13-3 and their relationship with fructosyltransferases were examined in the flag leaves and top two internodes of wheat SB169 line at anthesis using quantitative RT-PCR. The unspliced transcript forms of all three TaMYB13 genes were found to be a predominant form in these organs (FIG. 7a). The ratio of the correctly spliced transcript to unspliced form in these organs was higher for TaMYB13-1 than TaMYB13-2 and TaMYB13-3. The ratio of correctly spliced to unspliced form of three TaMYB13 genes was at least 4 times higher in the stem than in the flag leaf. The correctly spliced transcript levels of three TaMYB13 genes in wheat flag leaves were about 2% of their levels in the second internode of the stems at anthesis (FIG. 7a). 1-SST and 6-SFT mRNA levels in the flag leaves were also very low, about 15-fold lower than those in the second internode at anthesis (FIG. 7a). The levels of both transcript forms of all three TaMYB13 genes were highly correlated (r values ranging from 0.87 to 0.98) with those of Ta6-SFT1 and Ta1-SST1 among 9 samples from the flag leaves, peduncle and penultimate internodes of SB169 plants at anthesis grown under controlled environmental conditions (FIG. 7b).

Among three TaMYB13 genes, the correctly spliced transcript level of TaMYB13-1 was more abundant than those of TaMYB13-2 and TaMYB13-3. Therefore, in further analyses, the inventors focused on the expression profile of TaMYB13-1 correctly spliced transcript and its relation to fructosyltransferase expression. The expression of TaMYB13-1 in wheat leaves showed a 2.5-fold increase by sucrose treatment in the dark and up-regulation of 1-SST and 6-SFT genes by sucrose was more dramatic (FIG. 8a). The mRNA levels of these genes also increased by glucose treatment, but up-regulation by glucose was not statistically significant (FIG. 8a). TaMYB13-1 was markedly up-regulated during stem development (FIG. 8b left). Developmental changes in the TaMYB13-1 mRNA level during stem development were highly correlated (r values between 0.90 and 0.93) with those of 1-SST and 6-SFT genes in the samples of plants grown in a controlled environmental room (FIG. 8b middle and right).

With primers specific for the correct form of TaMYB13-1 mRNA, the inventors also examined the expression levels of TaMYB13-1, 1-SST and 6-SFT genes in the stems of field-grown SB lines (8 SB lines with 2 field replicates). The quantitative RT-PCR data also showed significant correlations in expression of TaMYB13-1 with these fructosyltransferases as well as stem WSC and fructan concentrations in 8 field-grown SB lines among samples (n=16) or genotypes (n=8) (Table 3).

Table 3. Correlation of the correctly spliced TaMYB13-1 transcript levels with fructosyltransferase mRNA levels, stem WSC and fructan concentrations in 8 SB lines. SB lines were grown in the field under rain-fed conditions with 2 field replicates. The relative mRNA levels of each gene in the top two internodes were measured using quantitative RT-PCR. Correlation was analysed at both sample level (n=16) and genotypic level (n=8), *$P<0.05$; **$P<0.01$

| Gene or carbohydrate | Correlation coefficient with TaMYB13-1 | |
|---|---|---|
| | In 16 samples | In 8 SB lines |
| Ta6-SFT1 | 0.90** | 0.92** |
| Ta6-SFT2 | 0.86** | 0.91** |
| Ta1-SST1 | 0.78** | 0.83* |
| Ta1-SST2 | 0.74** | 0.77* |
| Stem WSC | 0.81** | 91** |
| Stem fructan | 0.71** | 0.71* |

Example 5

TaMYB13 Binds to a DTTHGGT Core Sequence, which is Present in Fructosyltransferase Promoters In order to understand the role of TaMYB13 in regulation of 1-SST and 6-SFT, the inventors performed in vitro random DNA-binding site selection to determine the TaMYB13 DNA-binding sequences using an oligonucleotide containing a 30-bp random sequence and TaMYB13-1 fused with cellulase D (CELD) as a reporter for DNA-binding assay (Xue, 2005). Thirty-nine clones obtained from TaMYB13-selected oligonucleotides after five rounds of selection were verified for the presence of TaMYB13-binding sites in DNA-binding assays and were subsequently sequenced. These clones represent 17 unique sequences (FIG. 9). The sequence alignment of these selected sequences revealed a DNA-binding sequence profile as shown in FIG. 9. Some of these selected oligonucleotides contained two core binding sequences in different orientations. This core sequence was further defined by base substitution mutagenesis of SynO2 (FIG. 10), corresponding to the selected sequence SO2 (FIG. 9). This quantitative analysis of TaMYB13 DNA-binding sequence specificity showed that the core binding sequence was DTTHGGT (SEQ ID NO:73), where D represents AGt and H is Atc (preferred bases in these positions are in capital letters). The sequence flanking the core sequence can also markedly influence TaMYB13 binding activity (FIG. 10). Its preferred binding sequence was AARTTAGGTAR (SEQ ID NO:74) (FIG. 10). Multiple base substitutions (SynO2m25 and SynO2m26) of its preferred flanking sequence resulted in a dramatic reduction of their binding affinity (FIG. 10).

A search for TaMYB13 binding site (DTTHGGT) in cereal 1-SST and 6-SFT promoters identified the presence of TaMYB13-binding elements in the promoters of barley Hv6-SFT and wheat Ta6-SFT and Ta1-SST genes (FIG. 11a). Prior to this study, only two promoter sequences of wheat and barley 1-SST and 6-SFT genes are available in public sequence databases. The promoters of two wheat 6-SFT genes (Ta6-SFT1 promoter, HQ738530; Ta6-SFT2 promoter, HQ738531) were isolated from SB169 line through inverse PCR. Ta6-SFT1 and Ta6-SFT2 promoters share 72% nt sequence identity. During this work, a 3.25-kb Ta6-SFT promoter is released in GenBank (GU944823), which shares 98% nt identities with Ta6-SFT1 promoter. DNA binding assays showed that TaMYB13 was capable of binding to DTTHGGT elements present in these promoters except the DTTHGGT sites 2 and 3 of Hv6-SFT promoter (FIG. 11).

Example 6

TaMYB13 is a Transcriptional Activator, Positively Regulating 1-SST and 6-SFT Expression To provide further evidence on the potential role of TaMYB13 in modulating fructan synthesis, the inventors performed transactivation assays of a Hv6-SFT, Ta6-SFT1 or Ta1-SST promoter-driven reporter gene in wheat leaves with or without co-introduction of TaMYB13-1 (the effector gene) driven by a constitutive barley HvDhn8s promoter (Xiao and Xue, 2001). As shown in FIG. 2a, co-introduction of the TaMYB13 construct markedly increased the expression levels of the fructosyltransferase promoter-driven reporters. This analysis clearly demonstrated that TaMYB13 is a transcriptional activator of these fructosyltransferases.

To determine whether 6-SFT and 1-SST genes in wheat are direct target genes of TaMYB13. Promoter truncation and TaMYB13-binding site mutation of Ta6-SFT1 and Ta1-SST were performed. There are three TaMYB13-binding sites (S1, S2 and S3) present in the Ta6-SFT1 promoter; Ta6-SFT1 S1 and S2 had higher binding affinity than S3 (FIG. 11a). The point mutation of S1 (TGTTAGGTTCG-GTT) (SEQ ID NO:124) of Ta6-SFT1SXR construct by changing to TGTTA<u>AAA</u>TCGGTT (SEQ ID NO:125) (Ta6-SFT1SXR-mS1) led to a marked reduction in the XynA reporter expression and TaMYB13-mediated transactivation (FIG. 2b). The deletion of Ta6-SFT1 S1 and S2 (Ta6-SFT1SXR-ΔS1S2) further reduced the activity of TaMYB13-mediated transactivation, while the addition of a duplicated Hv6-SFT S1 (TATGTTAGGTAC) (SEQ ID NO:129) sequence (Ta6-SFT1SXR-SS construct) to Ta6-SFT1SXR-ΔS1S2 resulted in a dramatic increase in the activity of TaMYB13-mediated transactivation (FIG. 2b).

For Ta1-SST promoter, there are two TaMYB13-binding sites (S1 and S2) with S2 (ATGTTCGGTAA) (SEQ ID NO:127) having higher binding affinity than S1 (GCATT-AGGTTC) (SEQ ID NO:132) (FIG. 11a). Ta1-SSTSXR-ΔS1mS2 construct, where S1 was truncated and S2 was mutated by, changing to ATGTTC<u>CAAAA</u> (SEQ ID NO:128), had a markedly lower TaMYB13-mediated transactivation than the S1-truncated construct (Ta1-SSTSXR-ΔS1) (FIG. 2b). However, elimination of two TaMYB13-binding sites in Ta1-SST promoter did not completely abolish the XynA reporter expression. A significant TaMYB13-mediated transactivation activity was still observed in Ta1-SSTSXR-ΔS1mS2 (the reporter gene expression being 52% higher in the presence of HvD8MYB13R than its absence).

Example 7

Expression Levels of TaMYB13 are Positively Associated with Genotypic Variation in Grain Weight and Grain Yield Among SB Lines As a transcription factor regulates a group of target genes, it generally has a strong impact on agronomic traits. Therefore, the inventors also analysed genotypic variation in TaMYB13-1 correctly spliced transcript level in the top two internode samples of 16 SB lines grown in the field under rain-fed conditions and its association with grain weight and yield. This analysis revealed that TaMYB13-1 mRNA level was positively correlated with the grain weight and yield of 16 SB lines (FIG. 12), particularly its correlation with grain weight being highly significant ($P<0.01$).

Example 8

Evaluation of TaMYB13 Binding Specificity in Relation to the Binding Sites of Other Plant R2R3 MYB Proteins Plant R2R3-MYB proteins form a large group of MYB subfamily with 126 members in *Arabidopsis thaliana* (Chen et al., 2006). Relatively few studies have been reported on the analysis of the DNA-binding sequence profiles of plant R2R3-MYB proteins. To evaluate whether TaMYB13 share some binding sequence commonality with other R2R3-MYB proteins, the inventors determined the relative binding activity of TaMYB13 to the following binding sites of previously reported plant R2R3-MYB proteins: the *Petunia hybrida* MYB.Ph3-selected binding sites (MYB.Ph3-I and MYB.Ph3-II, Solano et al., 1995), *Pinus taeda* MYB1 and MYB4 binding sequences present in the promoter of *Phaseolus vulgaris* PHENYLALANINE AMMONIA-LYASE 2 (AC-I, AC-II and AC-III, Patzlaff et al., 2003ab; Hatton et al., 1995; AC-III is also the binding site of *Antirrhinum majus* MYB305, Sablowski et al., 1994) and the potential binding sequences (MRE, MRE2 and ERE) of *Arabidopsis* MYB59, based on the positive results in a yeast one-hybrid assay (Mu et al., 2009). As shown in Table 4, TaMYB13 strongly bound to AC-III element that contains a TaMYB13-preferred core binding sequence (GTTAGGT) (SEQ ID NO:133). TaMYB13 showed low binding activity (less than 20% of its preferred binding sequence activity) towards MYB.Ph3-II (AGTTAGTTA) (SEQ ID NO:134) and MRE2 (TATAACGGTTTTT) (SEQ ID NO:135), but with no or negligible activity to MYB.Ph3-I, AC-I, AC-II, MRE and ERE.

To further analyse the relative binding affinity of the previously reported plant R2R3 MYB protein sites in relation to the preferred TaMYB13-binding site, a binding site competition analysis was performed. Relative TaMYB13 binding activity to three biotin-labelled probes (SynO2m14, MYB.Ph3-II and MRE2) was assessed in combination with or without one of the four unlabelled competitors in a 2.5-fold amount: SynO2m14, MYB.Ph3-II, MRE2 and AC-I. The addition of a 2.5-fold amount of unlabelled SynO2m14 to biotin-labelled SynO2m14 reduced the TaMYB13 binding activity by about 60%. In contrast, only a slight reduction in TaMYB13-binding to biotin-labelled SynO2m14 was observed in the presence of unlabelled MYB.Ph3-II or MRE2 (FIG. 13a). The addition of unlabelled AC-I did not affect TaMYB13 binding to biotin-labelled SynO2m14. With biotin-labelled MYB.Ph3-II or MRE2 as a probe, TaMYB13 binding activity was reduced by more than 5-fold in the presence of unlabelled SynO2m14 (FIG. 13b-c).

Table 4. The binding activity of TaMYB13-1 to the binding sequences of previously reported plant R2R3-MYB proteins. SynO2m5 is a TaMYB13-preferred binding sequence. MYB.Ph3-I and MYB.Ph3-II are the MYB.Ph3-selected binding sites (consensus sequences). AC-I, AC-II and AC-III are the PtMYB1 and PtMYB4 binding sequences. AC-III is also the binding site of AmMYB305. MRE, MRE2 and ERE are the potential binding sequences of AtMYB59. The MYB-binding sequences identified in this study or reported previously are in bold. Relative TaMYB13 binding activity values are presented as means±SD of three replicated assays. Rev-Comp, reverse complementary to the published sequence.

| Name | Oligonucleotide sequence | Relative TaMYB13 binding activity |
|---|---|---|
| SynO2m14 | TCGAGGGAATAAAGTTAGGTAAGATGT (SEQ ID NO: 60) | 1.00 ± 0.16 |
| MYB.Ph3-I | TCGAGGGAATAAAAACGGTTATGATGT (SEQ ID NO: 136) | 0.04 ± 0.01 |
| MYB.Ph3-II | TCGAGGGAATAAAGTTAGTTATGATGT (SEQ ID NO: 90) | 0.15 ± 0.02 |
| AC-I (rev-comp) | TCGAGGGAATAAGGTAGGTGGATGATGT (SEQ ID NO: 92) | 0.03 ± 0.01 |
| AC-II (rev-comp) | TCGAGGGAATAGGGTTGGTGGATGATGT (SEQ ID NO: 137) | 0 |
| AC-III | TCGAGGGAATAAAGTTAGGTTATGATGT (SEQ ID NO: 138) | 0.61 ± 0.04 |
| MRE (rev-comp) | TCGAGGGAATAATTTTTGGTTTGATGT (SEQ ID NO: 139) | 0.02 ± 0.01 |
| MRE2 | TCGAGGGAATTATAACGGTTTTTTGAT (SEQ ID NO: 91) | 0.16 ± 0.02 |
| ERE | TCGAGGGAATAAAATTTCAAATGATGT (SEQ ID NO: 140) | 0 |

Example 9

Production and Analysis of Transgenic Wheat Heterologously Expressing TaMYB13

A TaMYB13 expression plasmid was constructed by inserting the protein coding region of TaMYB13 between a barley 6-SFT promoter isolated from barley landrace 'Sahara' and a rice rbcS 3' transcription termination/polyadenylation region in the pSP72 vector using the construction method as described by Xiao and Xue (2001). The correctness of the construct was confirmed by nucleotide sequencing.

For wheat transformation, immature embryos from wheat cultivar Bobwhite SH98-26 and the particle bombardment method were used according to Pellegrineschi et al. (2002). The TaMYB13 expression cassette and selectable marker gene cassette (rice act1:bar:Nos3', constructed from pAAI1GUSR and pDM803 (Patel et al., 2000)) were amplified from expression plasmids constructed in the pSP72 vector using PCR. The PCR-amplified gene cassettes were purified using a Qiagen column. The TaMYB13 expression cassette was co-introduced with the selectable marker gene cassette into the immature embryos. The herbicide phosphinothricin was used for selection of transformed calli. Plantlets generated through the wheat transformation process were grown in a controlled-environment growth room in 1.5-L pots, containing a 3:1:1 mix of sand:soil:peat under night/day conditions of 16-h light (500 pmol m$^{-2}$s$^{-1}$), 16/20° C. and 80/60% relative humidity.

Analysis of TaMYB13 Transgene in Transgenic Lines

The presence of the TaMYB13 transgene in phosphinothricin-resistant wheat plants was analysed using real-time PCR amplification of a portion of the transgene using primers targeting to the rice rbcS3' region (rbcS3bF3: 5'-GCGAGGAGTCTGGTGGCAACT (SEQ ID NO:141); rbcS3bR4: 5'-AAGCAGAGCACGGCCGGTAA (SEQ ID NO:142)). The genomic DNA was prepared from 15-30 mg samples from young leaves by extraction with 0.6 ml of 1% (w/v) SDS and 0.5 M NaCl at 70° C. for 30 min after freeze-and-thawing of the leaf samples three times. The treated leaf samples were shaken vigorously for several hours to aid the release of genomic DNA into the solution. The genomic DNA was precipitated by adding an equal volume of iso-propanol, washed twice with 75% ethanol and dissolved in 50 μl of 2 mM Tris-HCl (pH 8) and 0.2 mM EDTA and 0.02 mg ml$^{-1}$ of DNase-free RNase A. After incubation at 37° C. for 3 h, 2 μl of the DNA solution was used in a 10-μl real-time PCR reaction for detection of the presence of the TaMYB13 transgene with an ABI Prism 7900 sequence detection system (Applied Biosystems) using SYBR Green PCR Master Mix (Applied Biosystems) according to the manufacturer's instructions. Genomic DNA prepared from non-transgenic Bobwhite was used as a negative control.

The expression of the TaMYB13 transgene in transgenic lines was analysed using quantitative RT-PCR as described above and primers corresponding to the rice rbcS3' region (rbcS3bF3 and rbcS3bR4).

Over-Expression of TaMYB13 in Transgenic Wheat Leads to Enhanced Expression of Fructosyltransferase Genes, Increased Accumulation of WSC and Fructans In order to investigate whether enhancing TaMYB13 expression level had a positive effect on stem fructan and WSC accumulation, and yield-related traits in transgenic wheat, transgenic lines over-expressing TaMYB13 were generated using the TaMYB13 construct as described above. Expression of the transgene was driven by a barley 6-SFT promoter. Seven transformed lines were obtained, self-fertilised to obtain T1 seed, and the subsequent T1 plants self-fertilised to produce T2 seed. Homozygous T2 seed were selected and sown to produce T2 plants. The T2 transgenic lines over-expressing the TaMYB13 were thereby obtained. The expression levels of the TaMYB13 transgene was analysed by RT-PCR, and the data is shown in FIG. 14.

The presence and expression of Hv6-SFT promoter driven TaMYB13 transgene was confirmed with genomic and RT PCR using the primer pair corresponding to the rice rbcS 3' region of the transgene. The average expression levels of TaMYB13 in the flag leaf and top internode (peduncle) in these transgenic lines at anthesis increased over 5.5-fold and 2.5-fold, respectively, compared to those in non-transgenic Bobwhite (FIG. 14). The over-expression of TaMYB13 resulted in marked increases in the expression levels of Ta6-SFT and Ta1-SST genes in the top internode and flag leaf at anthesis and also a significant increase in Ta1-FFT1 expression in these organs (Table and Table 6).

TABLE 5

Relative expression levels of fructosyltransferase genes in the top internode of Bobwhite (n = 3) and T2 transgenic lines carrying SFT-TaMYB13 (n = 7) at anthesis.

|  | Bobwhite control | | SFT-TaMYB13 | | |
| --- | --- | --- | --- | --- | --- |
|  | mean | SD | mean | SD | p-value |
| Ta6-SFT1 | 1.00 | 0.557 | 5.15 | 1.639 | 0.006 |
| Ta6-SFT2 | 1.00 | 0.607 | 6.14 | 2.265 | 0.009 |
| Ta1-SST1 | 1.00 | 0.109 | 2.17 | 0.458 | 0.005 |
| Ta1-SST2 | 1.00 | 0.673 | 7.12 | 2.075 | 0.003 |
| Ta1-FFT1 | 1.00 | 0.226 | 1.85 | 0.357 | 0.010 |
| Ta1-FFT2 | 1.00 | 0.575 | 2.23 | 3.201 | 0.543 |

TABLE 6

Relative expression levels of fructosyltransferase genes in the flag leaf of Bobwhite (n = 3) and T2 transgenic lines carrying SFT-TaMYB13 (n = 5) at anthesis.

|  | Bobwhite control | | SFT-TaMYB13 | | |
| --- | --- | --- | --- | --- | --- |
|  | mean | SD | mean | SD | p-value |
| Ta6-SFT1 | 1.00 | 0.81 | 5.49 | 2.07 | 0.024 |
| Ta6-SFT2 | 1.00 | 0.79 | 5.88 | 3.74 | 0.091 |
| Ta1-SST1 | 1.00 | 0.59 | 4.52 | 1.42 | 0.016 |
| Ta1-SST2 | 1.00 | 0.59 | 4.78 | 1.82 | 0.027 |
| Ta1-FFT1 | 1.00 | 0.59 | 3.70 | 1.56 | 0.048 |
| Ta1-FFT2 | 1.00 | 0.73 | 3.60 | 1.26 | 0.036 |

In a second experiment, the $T_2$ plants of five TaMYB13 transgene expressing lines (a20c1, b36c1, b2c1 and b13b1 and b13b3) were analysed for the expression level of TaMYB13 in the flag leaves at anthesis. The primers used amplified both the correctly spliced endogenous TaMYB13 as well as the transgene TaMYB13. The expression levels of TaMYB13 in the flag leaves of transgenic plants was from 2.3 times (b13b3) to 9.1 times (b36c1) higher than that of wild-type control plants (Bobwhite).

Example 10

Upregulation of Target Genes of TaMYB13 in TaMYB13-Over-Expressing Transgenic Wheat Three transgenic lines (a20c1, b2c1 and b36c1) were analysed to examine changes in the expression levels of target genes of TaMYB13. Since the expression of many genes might be affected by the upregulation of transcription factors like TaMYB13, the inventors decided to use the Affymetrix wheat gene chip to study the expression of the wheat transcriptome, comparing the three transgenic lines with three wild-type control plants. From the generated dataset, genes that had an expression level that was notably increased or decreased (factor 2; p-value<0.05) were selected. Thirty-two probesets (26 genes) had an increased expression level in the transgenic lines compared to the control plants (Table 7), whereas 22 probesets (22 genes) had a lower expression level. Sugar metabolism and fructan synthesis related genes were the most frequently observed type of up-regulated target genes in the transgenic lines, and accounted for 11 of the 32 up-regulated probesets. Amongst these 11 probesets were five probesets that targeted Ta1-SST and Ta6-SFT which were shown to be directly activated by TaMYB13. The inventors decided to focus on the up-regulated genes, since this would more likely result in the identification of direct targets of TaMYB13.

TABLE 7

Listing of genes that were increased at least two-fold in TaMYB13 over-expressing transgenic lines compared to Bobwhite control plants in Affymetrix wheat genome array data. The table contains a description of the genes targeted by the up-regulated probesets, expression ratio of individual probesets in the transgenic lines relative to control plants (EXPR) and the p-value of the differences between two groups.

| Probeset | Description | EXPR | p-value |
| --- | --- | --- | --- |
| Ta.24195.1.A1_at | unknown protein | 17.17 | 0.02 |
| TaAffx.71942.1.A1_at | Putative retroelement | 5.42 | 0.00 |
| Ta.3475.2.S1_at | 1-FFT2 | 5.32 | 0.04 |
| Ta.3475.1.A1_at |  | 4.35 | 0.02 |
| TaAffx.83540.1.S1_at | unknown protein | 4.60 | 0.00 |
| Ta.2788.1.A1_at | 1-SST2 | 4.20 | 0.02 |
| Ta.2789.1.S1_a_at ** | SFT2 | 3.92 | 0.03 |
| Ta.2789.2.S1_x_at ** |  | 3.31 | 0.03 |
| Ta.2789.2.S1_at |  | 2.74 | 0.03 |
| Ta.2789.1.S1_at | SFT1 | 3.11 | 0.02 |
| Ta.12834.1.S1_s_at | MYB13.1/2/3 | 3.73 | 0.05 |
| Ta.12258.1.A1_at | unknown protein | 3.38 | 0.00 |
| Ta.7378.5.A1_at | putative histone H2B | 3.10 | 0.04 |
| Ta.13965.1.S1_at | ubiquitin-protein ligase | 2.88 | 0.04 |
| Ta.30798.3.S1_at | vacuolar processing enzyme 3 | 2.85 | 0.02 |
| Ta.15881.1.S1_at | eukaryotic translation initiation factor | 2.61 | 0.02 |
| TaAffx.19583.2.A1_at | microtubule associated protein | 2.61 | 0.00 |
| TaAffx.59883.1.S1_at | putative amino acid permease | 2.50 | 0.05 |
| Ta.10107.2.S1_a_at | putative fructokinase | 2.50 | 0.01 |
| Ta.10107.2.S1_x_at |  | 2.49 | 0.02 |
| Ta.10107.1.S1_at |  | 2.18 | 0.02 |
| Ta.25919.1.S1_at | MYB transcription factor | 2.45 | 0.04 |
| Ta.23069.1.S1_at | auxin-responsive Aux/IAA family member | 2.42 | 0.05 |
| TaAffx.43914.1.S1_s_at | predicted protein | 2.41 | 0.02 |
| Ta.1549.1.S1_at | aspartyl protease family protein | 2.40 | 0.00 |
| Ta.20658.1.S1_a_at | putative lipase | 2.36 | 0.01 |
| Ta.10838.1.S1_at | CCT motif family protein | 2.31 | 0.03 |
| Ta.10838.1.S1_x_at |  | 2.17 | 0.04 |
| Ta.10772.1.A1_at | nodulin-like protein | 2.26 | 0.03 |
| Ta.28063.1.S1_x_at | glycine-rich protein | 2.21 | 0.01 |
| Ta.20658.2.S1_x_at | esterase precursor | 2.16 | 0.03 |
| Ta.27746.1.S1_at | Hypothetical protein | 2.05 | 0.03 |

As expected, the hybridisation signal of the TaMYB13 probeset (Ta.12834.1.S1_s_at) was higher in the transgenic lines than control plants, as it targeted both the native and the transgenic version of TaMYB13. Another confirmation of the validity of the data came from the upregulation in the transgenic lines of five probesets that targeted Ta1-SST and Ta6-SFT1 and Ta6-SFT2, which were shown to be targets of TaMYB13 in transient transactivation assays. Interestingly, Ta1-FFT, represented by the probesets Ta.3475.2.S1_at and Ta.3475.2.S1_at, also had an increased signal of about 4-5 times higher than control levels, indicating that TaMYB13 had an impact on the expression of all three major fructosyltransferases (FTs) in wheat. Besides FTs, other probesets that were up-regulated in the transgenic lines included three probesets that targeted a putative fructokinase (TaFK1) and Ta.30798.3.S1_at that targeted a γ-vacuolar processing enzyme (Taγ-VPE). To validate the upregulation of these genes, the expression of the seven above mentioned genes was measured by quantitative RT-PCR using cDNA that was retro-transcribed from the RNA samples used in the Affymetrix experiment. As can be seen in FIG. 15a, the upregulation of all of these genes in the flag leaves of transgenic lines compared to the wild-type control plants was confirmed.

To determine the effect of TaMYB13 overexpression on these genes in the top-internode at anthesis, real-time PCR was performed on cDNA from this tissue to measure the expression levels. When compared to Bobwhite control plants, expression of TaMYB13 and all FT genes was increased, as well as of the Taγ-VPE gene in the transgenic lines (FIG. 15b).

Example 11

Enhanced Fructan Accumulation in TaMYB13-Over-Expressing Transgenic Wheat

The expression data clearly pointed to the fructan synthesis pathway as a target for TaMYB13 regulation. It was known that a good correlation existed between Ta1-SST mRNA levels and its enzyme activity in wheat (Xue et al. 2008a) and Hv6-SFT mRNA levels and its enzyme activity in Barley (Sprenger et al. 1995). Since genes from Ta1-SST and Ta6-SFT families, together with Ta1-FFT family genes, were highly up-regulated in the TaMYB13 transgenic lines, the fructan and sugar contents in these transgenic lines were measured and compared with wild-type control plants.

Flag leaves and the top internodes from the TaMYB13 plants grown in controlled environment were harvested at anthesis. After grinding the tissue in liquid nitrogen, 1 g of tissue was used for the WSC extraction, which was performed as described by Xue et al. (2008a). The levels of WSC components (sucrose, glucose, fructose and fructans) were determined by injection of WSC extracts into a HPLC system (controller, Waters 600 s; pump, Waters 626; autosampler, Waters 717; Waters, Mass., USA) and separated on an analytical column (CarboPac PA-100; Dionex Pty Ltd, California, USA) protected by a guard column (CarboPac Pa-100 guard column; Dionex Pty Ltd), using 50-150 mM of NaOH as a mobile phase. Pulsed amperometric detection (Waters 464; Waters) was used to detect the eluted sugars. Sugar standards were loaded before and after each 10 samples, which were used as external standards to calculate standard curves to be able to quantify the eluted sugars. Approximately 80 µg sugars was loaded on 20 cm×20 cm aluminium plates pre-coated with silica-gel, 0.2 mm thick (Merck, TLC Silica gel 60 F254). The TLC was run twice as described by Incoll et al. (1989) with 1-propanol:Ethyl-ethanoate:water 5:3:2 (v/v). Sugars and fructans separated on TLC plates were visualised by spraying the plates with urea-phosphoric acid and heating the plates at 110° C. as described by Wise et al. (1955). Water-extracted WSC from *Helianthus tuberosus* were used as reference markers for fructans.

As can be seen in FIG. 16, the fructan levels in the top-internode as well as the flag leaves were increased in the transgenic lines compared to the control plants. The increase in fructans in flag leaves as well as the top-internode was statistically significant ($P \leq 0.01$). The TaMYB13 over-expression lines also showed a significant increase in the WSC concentration in the flag leaf and top internode (FIG. 17). In particular, an increase in fructan concentration in the flag leaf and top internode in the transgenic lines was more marked (FIG. 17). Both organs had a significant increase in total WSC contents ($P<0.05$), with the fructans being the biggest contributor to this increase. The transgenic lines contained more fructans, in particular the high molecular weight fructans, in the flag leaf and top internode at anthesis than the wild-type Bobwhite, as determined by TLC analysis of leaf extracts.

Transgenic lines also had slightly higher grain weight than. Bobwhite (Table 8 and Table 9). Other phenotypes of transgenic lines appear to be normal.

TABLE 8

Grain yield, grain weight and top spike weight of Bobwhite (n = 7) and top 5 T2 transgenic lines carrying SFT-TaMYB13 grown in separate 15-cm diameter pots.

|  | GY/plant (g) | HGW (g) | TSW (g) |
|---|---|---|---|
| Bobwhite | 23.4 ± 2.5 | 4.93 ± 0.22 | 4.25 ± 0.24 |
| SFT-TaMYB13 | 26.9 ± 2.5* | 5.20 ± 0.11* | 4.82 ± 0.50* |

GY = grain yield, HGW = hundred grain weight, TSW = top spike weight
*$P < 0.05$

TABLE 9

Grain yield, grain weight and top spike weight of Bobwhite (n = 3) and top 4 T2 transgenic lines carrying SFT-TaMYB13 grown in 30-cm diameter pots.

|  | GY/plant (g) | HGW (g) | TSW (g) |
|---|---|---|---|
| Bobwhite | 35.8 ± 1.9 | 5.00 ± 0.16 | 4.77 ± 0.08 |
| SFT-TaMYB13 | 40.3 ± 6.7 | 5.25 ± 0.11* | 4.62 ± 0.54 |

GY = grain yield, HGW = hundred grain weight, TSW = top spike weight
*$P < 0.05$ Example 12

Presence of TaMYB13 Binding Sites in Regulatory Regions of Target Genes

The wheat Affymetrix array expression analysis showed several candidate genes that were directly or indirectly regulated by TaMYB13. In the case of Ta1-SST and Ta6-SFT, this up-regulation was very likely to be direct since there were TaMYB13-binding sites present in the regulatory region of these genes. Furthermore, point mutations or deletions of these sites resulted in a decreased induction of a reporter gene in the presence of TaMYB13 in transient expression assays (Example 6). Therefore, the presence of one or more TaMYB13 DNA-binding sequences present in the regulatory regions of the up-regulated genes in the Affymetrix data might indicate direct regulation of these genes by TaMYB13.

The BLAST function on the cerealsDB website (http://www.cerealsdb.uk.net/CerealsDB) was used to identify regulatory regions of genes that were up-regulated in the TaMYB13 transgenic lines. The sequences of the Affymetrix probes for the target genes were used as query sequences to BLAST the genomic sequence of wheat from the cerealsDB (http://www.cerealsdb.uk.net). The retrieved sequence was subsequently used in a new BLAST search to retrieve additional sequences. The final retrieved genomic sequence contigs were cross checked with EST data from NCBI (http://blast.ncbi.nlm.nih.gov/Blast.cgi) and the DFCI *Triticum aestivum* Gene Index (http://compbio.dfci.harvard.edu/cgi-bin/tgi/gimain.pl?gudb=wheat) to determine the intron-exon structure and putative transcription/translation initiation sites. Where possible, at least 1000 bp of nucleotide sequence upstream of the translation initiation sites was identified. The obtained sequences and probable gene structures are displayed in Table 10.

TABLE 10

Numbers of TaMYB13 DNA-binding motifs found in the regulatory region of target genes of TaMYB13. MBS URS displays the number of TaMYB13 DNA-binding motifs found in the upstream regulatory region and MBS INTRON displays the number of TaMYB13 DNA-binding motifs found in introns of the target genes.

| Target | Sequence length | MBS URS | MBS INTRON |
|---|---|---|---|
| 1-FFT2 | 1425 | 3 | 0 |
| 1-SST2 | 2244* | 2 | n.d. |
| SFT2 | 850* | 4 | n.d. |
| SFT1 | 1001* | 3 | n.d. |
| MYB13.1/2/3 | 760 | 1 | 1 |
| NBS-LRR resistance-like protein | 300 | 0 | 0 |
| putative histone H2B | 960 | 1 | 0 |
| ubiquitin-protein ligase | 622 | 0 | 1 |
| vacuolar processing enzyme | 1140 | 2 | 5 |
| putative amino acid permease | 1061 | 0 | 5 |
| putative fructokinase | 1209 | 0 | 4 |
| MYB transcription factor | 1918 | 1 | 0 |
| IAA family member | 1172 | 0 | 1 |
| CCT motif family protein | 1831 | 1 | 3 |

The regulatory regions of 11 genes (represented by 16 probesets) were identified, in addition to the regulatory regions of Ta1-SST and Ta1SFT1/2, which were published previously (Nagaraj et al. 2001). The length of the upstream regulatory regions varied in the range from about 600 bp to about 2.2 kb, as shown in Table 10. Six of these newly identified genes contained at least one TaMYB13 DNA-binding sequence motif (DTTHGGT) in their upstream regulatory region. Besides Ta1-SST and Ta6-SFT1/2, notably Ta1-FFT contained three TaMYB13 DNA-binding motifs in its upstream regulatory region.

Several genes are known to be regulated by sequences that are present in their introns, for example AGAMOUS (AG) and SEEDSTICK (STK) (Deyholos and Sieburth 2000; Kooiker et al. 2005). Therefore, the inventors also searched for TaMYB13 DNA-binding motifs in the introns of the identified genes. As shown in Table 10, at least one binding site was present in the introns of seven of the analysed genes (e.g. TaFK1, Taγ-VPE and amino acid permease), and three of them even had four or more of these motifs in their introns.

TaMYB13 Binding to Target Genes

Though at least one core TaMYB13 DNA-binding motif was present in 10 of the 13 genes for which genomic sequence information was obtained, flanking regions were also examined since they can play a role in the determination of the binding affinity of TaMYB13. Therefore, CEL-D reporter based in vitro DNA-binding assays were performed to determine the affinity of TaMYB13 to the identified motifs in the upstream regulatory regions of the following up-regulated genes: Ta1-FFT (3 sites), TaMYB13-1, -2 and -3 (1 site each), TaH2B (1 site) and Taγ-VPE (2 sites). The data are shown in FIG. 18.

Oligonucleotides were designed for 10 bp upstream and downstream of the core sequence of TaMYB13 DNA-binding motifs. The TaMYB13 DNA-binding motifs present in the upstream regulatory region of Ta1-FFT were able to be bound by TaMYB13, though the affinity was stronger for the first site present at 1310 nucleotides before the translation start site (FIG. 18). TaMYB13 was also able to bind weakly to the motifs present in the upstream regulatory region of TaMYB13-1 and -2, but not the motif present in TaMYB13-3. No binding affinity of TaMYB13 for the motif present in the H2B promoter region was observed. (FIG. 18). The strongest interaction was with the motif present in the promoter of Taγ-VPE site 1 at −969 (FIG. 18), which was bound by TaMYB13 even stronger than SynO2, which was used as a positive control. Also the other site present in the same upstream regulatory region had strong affinity for TaMYB13 (FIG. 18).

Example 13

Expression Profiles of TaMYB13 and its Target Genes are Positively Correlated

The Affymetrix array data published by Xue et al. (2008a) was examined using 8 independent RILs with two field replicates per line (16 samples) in order to investigate the correlation between the expression of TaMYB13 and the genes that were up-regulated in the TaMYB13 over-expressing lines. High correlations were found between the expression of TaMYB13 and the targets Taγ-VPE, Ta1-FFT and TaFK1 (FIG. 19e-g), besides Ta1-SST and Ta6-SFT.

To further investigate the correlation between TaMYB13 and its target genes, the expression levels of these genes in developing stems (5 days before anthesis to 11 days after anthesis) was analysed. As shown in FIG. 19a-d, a strong correlation was observed between the expression of TaMYB13 and its target genes: Taγ-VPE, Ta1-FFT, Ta1-SST and Ta6-SFT1. However, correlation between the expression of TaMYB13 and TaFK1 in the stem samples was not statistically significant.

Example 14

Field Trial of TaMYB13 Over-Expression Transgenic Wheat Lines

Six TaMYB13 over-expressing transgenic lines at T2-T4 [a 1b2f1 (3 plots), a21c22a (3 plots), b2c21a2 (2 plots), b2c6f1c (2 plots), b13b7a (3 plots), b36c5 (1 plot)] were selected for a field trial at CSIRO's Ginninderra Experiment Station, Canberra. This field trial was permitted under license number DIR 111 of the Office of the Gene Technology Regulator. Wild-type (non-transformed) Bobwhite was used as the control variety (6 plots). 200 seeds were sowed per plot of 1 meter×1.6 meter with 6 rows. Plants are grown under rain-fed conditions.

The following traits are measured on the plants and produced grain: thousand grain weight, spike weight at maturity, grain weight per spike, tiller number per plant and grain yield (weight of grain per plant). The transgenic lines exhibit increased measures in these parameters.

Example 15

Related Genes from Other Species

Genes encoding homologs of the MYB13 polypeptides described herein from, for example, other species can be isolated using standard procedures. In one example, one or more of sequences provided as SEQ ID NOs 1 to 8 can be used to search sequence databases. Such procedures identified the homologs provided as 13 to 17 and 143 to 147. In another example, a probe(s) derived from a wheat and/or barley cDNA (for example derived from one or more of SEQ ID NOs 5 to 8) is used to probe a cDNA or genomic library using standard techniques. Candidate genes can be screened to determine if they encode a MYB polypeptide using techniques described herein, such as the procedure outlined in Example 6.

Example 16

Discussion

The present invention addresses regulatory gene(s) for controlling fructan accumulation in plants. Fructan synthesis in the developing stem of temperate cereals is predominantly by two types of fructosyltransferases, 1-SST and 6-SFT, resulting in deposition of the graminan type of fructan (Ritsema and Smeekens, 2003). Understanding of gene regulatory networks involved in fructan synthesis in important agronomic crops such as wheat and barley would provide better knowledge for genetic enhancement of fructan accumulation in these crops.

The inventors used correlation analysis and identified three highly homologous MYB transcription factors (TaMYB13-1, TaMYB13-2 and TaMYB13-3) with 100% identical in the MYB domain and sharing a similar expression pattern. As *T. aestivum* contains three genomes, it is possible that these three TaMYB13 genes are homoeologues. Analysis of a predominantly expressed TaMYB13-1 gene showed that its mRNA level was highly correlated with those of Ta1-SST and Ta6-SFT genes in wheat stems among recombinant inbred lines as well as with stem WSC and fructan concentrations. This positive correlation also extended to the developmental expression profiles of these genes in wheat stems. TaMYB13 and 1-SST/6-SFT genes were very highly expressed in wheat stem at anthesis, compared to the flag leaves. These expression patterns appear to be associated with differences in fructan accumulation between stems and flag leaves in wheat reported by Ruuska et al. (2008). The expression correlation data point to the potential role of TaMYB13 in regulation of these fructosyltransferase genes in wheat stems.

1-SST and 6-SFT genes are known to be up-regulated by sucrose in barley and wheat leaves (Müller et al., 2000; Koroleva et al., 2001; Nagaraj et al., 2001, 2004; Martinez-Noel et al., 2001, 2006; Ruuska et al., 2008). Similarly, TaMYB13-1 was also up-regulated by sucrose. However, there was a marked difference in the extent of up-regulation, indicating that other factors may also play a role in the sucrose-mediated up-regulation of these fructosyltransferase genes.

TaMYB13 transcripts were found to be alternatively spliced in wheat and so did its homologue in barley. The closest homologues of TaMYB13 in *Arabidopsis* (At-MYB48 and AtMYB59) also have alternatively spliced forms (Li et al., 2006). However, the role of alternative splicing, if any, of these MYB genes is still unknown.

TaMYB13 shares very high sequence similarity with AtMYB48 and AtMYB59 in the MYB domains (79% and 80% amino acid identity with TaMYB13-1, respectively), which is likely to share similar DNA-binding specificity. For example, AtMYC2 shares a high sequence similarity in the bHLH DNA-binding domain with OsbHLH66 (AY625681) and TabHLH94 (AY625684) and shares similar DNA-binding sequence specificity (Dombrecht et al., 2007; Xue, 2005). However, the DNA-binding sequence profile of AtMYB48/AtMYB59 and their closest homologues in other plant species has not been reported to date. The DNA-binding site selection experiment followed by base substitution analysis revealed that TaMYB13 bound to a DTTHGGT (SEQ ID NO:73) core sequence, which represents the first report of the DNA-binding sequence profile of TaMYB13-like MYB genes. However, the presence of this core binding sequence is not sufficient for the effective binding by TaMYB13 and the bases flanking the core sequence are also important determinants for its binding affinity. It is most likely that AtMYB48 and AtMYB59 are capable of binding to the TaMYB13-binding site based on the very high amino acid similarity in the MYB domain with TaMYB13. Thus, data on the TaMYB13 DNA-binding specificity provide fundamental information for future investigation of the potential direct target genes of AtMYB48 and AtMYB59 in *Arabidopsis* and their homologues in other plant species.

Comparative analysis of TaMYB13 binding activity to a number of previously reported plant R2R3 MYB binding sites revealed that TaMYB13 showed significant binding activity to the *Petunia hybrida* MYB.Ph3-selected binding site II (MYB.Ph3-II), but not site I (MYB.Ph3-I) (Solano et al., 1995). TaMYB13 and MYB.Ph3 have 53% amino acid identity in the MYB domains. TaMYB13 also bound to one of three AC elements, AC-III, present in the promoter of PHENYLALANINE AMMONIA-LYASE 2 from *Phaseolus vulgaris* (Hatton et al., 1995), but not AC-I and AC-II. AC-III has been shown to be a binding site of *P. taeda* PtMYB1, PtMYB4 and *A. majus* AmMYB305 (Patzlaff et al., 2003ab; Sablowski et al., 1994). The MYB domains of PtMYB1 and AmMYB305 share 61.5% amino acid identity with TaMYB13-1. PtMYB4 shares 55% amino acid identity with TaMYB13-1 in the MYB domains. Among the above reported R2R3-MYB binding elements, AC-III contains a perfect match to the TaMYB13-preferred core binding sequence and MYB.Ph3-II shares high sequence similarity with TaMYB13 binding site. Most interestingly, TaMYB13 also showed significant binding activity towards MRE2, which shares little sequence similarity with TaMYB13-selected sequences. This indicates that the MRE2 sequence is another binding site of TaMYB13-like R2R3-MYB proteins, although TaMYB13 binding activity to this element is only 16% of TaMYB13-preferred binding sequence. Mu et al. (2009) have shown that AtMYB59 is capable of interacting with the MRE2 element in a yeast one-hybrid assay, likely through direct binding to this element in the yeast. Overall DNA binding data suggest that different groups of R2R3-MYB proteins possess unique DNA-binding sequence specificity, but also share some common binding sequences, such as GTTAGGT (SEQ ID NO:133) and AGTTAGTTA (SEQ ID NO:134). However, it is likely that their sequence preference differ among different groups of R2R3-MYB proteins. For example, PtMYB4 binds much more strongly to AC-I and AC-II elements than AC-III (Patzlaff et al., 2003b).

Using the DNA-binding sequence profile data, the inventors identified the DTTHGGT cis-acting element in the promoters of wheat Ta6-SFT1 and Ta6-S1, 12, Ta1-SST and barley Hv6-SFT genes and also confirmed the ability of TaMYB13 to bind to this cis-element in these fructosyltransferase promoters. The TaMYB13 binding site is repeated at least twice in these wheat fructosyltransferase promoters. Most importantly, this study demonstrated that TaMYB13 functioned as a transcriptional activator, positively regulating the expression of Ta1-SST and Hv6-SFT promoter-driven reporter genes in wheat. The deletion and point mutation of TaMYB13-binding sites in the Ta6-SFT1 and Ta1-SST promoters markedly reduced reporter gene expression driven by these deletion/mutant promoters and TaMYB13-mediated transactivation activity, suggesting that TaMYB13 plays a significant role in transcriptional regulation of these fructosyltransferase genes in wheat. A proposed sucrose and stem developmental signal-mediated MYB13 regulatory pathway for fructan synthesis in temperate cereals is illustrated in FIG. 16. As the fructan synthetic pathway is not present in *Arabidopsis* and rice, AtMYB48 and AtMYB59 and their homologues in rice are not relevant to this pathway in these two model plant species.

Overexpression of TaMYB13 using a transgene encoding this protein resulted not only in increased expression levels of the genes encoding three fructosyltransferase enzymes but also increased fructan contents in stems and leaves of the transgenic plants. Analogous results are expected in other plants including other cereals which are transformed with constructs encoding MYB13 proteins.

The Affymetrix array expression analysis revealed that 26 genes were up-regulated at least two-fold in the TaMYB13 over-expressing transgenic lines compared to Bobwhite control plants. Of these up-regulated genes, three genes encoded the fructosyltransferases Ta1-SST, Ta6-SFT1 and Ta6-SFT2. Most interestingly, the gene encoding Ta1-FFT was also up-regulated in TaMYB13 over-expressing lines. Correlation analysis also showed that the expression levels of Ta1-SST, Ta6-SFT and Ta1-FFT were highly correlated with TaMYB13 expression among samples from transgenic lines and Bobwhite control plants, as well as among samples from different stem-developmental stages. The expression profiles of Ta1-SST and Ta6-SFT genes were positively correlated with that of TaMYB13 in recombinant inbred lines. Correlation analysis of the Affymetrix data published by Xue et al. (2008a) showed that the expression of Ta1-FFT (Ta.3475.2.S1_at) was also positively correlated with that of TaMYB13 ($r=0.74$). The correlation coefficients between TaMYB13 and Ta1-FFT in plants analysed in this study were very high, being 0.96 and 0.98 in the flag leaves and stems in transgenic plants and control plants, respectively, whereas the coefficient in different stem developmental stages was 0.94. The fact that there were very high expression correlations between TaMYB13 and Ta1-FFT in various genetic backgrounds as well as different stem developmental stages made it likely that Ta1-FFT was also a direct target of TaMYB13. To further support this hypothesis, it was shown using in vitro DNA-binding assays that TaMYB13 was able to bind three TaMYB13 binding motifs that are present in the upstream regulatory region of Ta1-FFT.

Besides genes that are directly involved in the fructan synthetic pathway, two other genes (Taγ-VPE and TaFK1) were found to be up-regulated in the TaMYB13 over-expressing lines and could be linked indirectly to this pathway. TaFK1, represented by three probesets on the Affymetrix array, was up-regulated about 2.4-fold in the transgenic lines, indicating a role of TaMYB13 in. the regulation of the fructose metabolism. Fructokinases (EC 2.7.1.4) catalyse the conversion of fructose to fructose-6-phosphate and have been shown to be induced upon the external application of sugars such as fructose, glucose and sucrose in tomato (Schaffer and Petreikov 1997). Davies et al. (2005) have shown that, in potato, fructokinases are able to balance sucrose synthesis and metabolism in concert with sucrose synthase. The increased demand for sucrose in the cells that express more FTs might therefore be balanced by the increase in fructokinase, since the product of this enzyme, fructose-6-phosphate, is a substrate for sucrose-phosphate synthase (EC 2.4.1.14). Therefore, an increase in fructokinase would favour carbon flow towards fructan accumulation. There were three TaMYB13 DNA-binding motifs present in the first intron of this gene, suggesting that direct regulation of this gene by TaMYB13 was occurring. The expression of TaMYB13 and TaFK1 correlated significantly in the datasets of the transgenic versus control plants and of the recombinant inbred lines. However, expression correlation of these two genes in the developing stems of wheat was not statistically significant, which indicated that the expression of TaFK1 might be regulated predominantly by other transcription factors in the stem. It was also interesting to note that TaFK1 is the dominant fructokinase in the leaves, whereas in stem other fructokinases (TaFK4) were more highly expressed (Xue et al. 2008a).

The other TaMYB13 up-regulated-gene that might be indirectly linked to the fructan synthesis was Taγ-VPE, which is thought to be involved in processing vacuolar fructosyltransferase proteins. VPE proteins are plant specific vacuolar proteases, originally identified in castor bean where they were shown to cleave storage proteins (Hara-Nishimura et al., 1991). Shimada et al. (2003) showed that the cleavage site of VPEs was preferentially between the Asn-Pro bond found in the S albumin storage proteins, but the enzyme could also cleave the bond between two aspartic acid residues. A more general cleavage after an Asn residue has been reported by Hara-Nishimura et al. (1991). Analysis of the Affymetrix data of recombinant inbred lines showed that the expression of Taγ-VPE was highly correlated with the expression of TaMYB13 in recombinant inbred lines ($r=0.85$). A similar correlation was observed in the developing stem samples ($r=0.81$) and in the transgenic/control plants ($r=0.91$). The upstream regulatory region of this gene contained 2 TaMYB13 DNA-binding motifs that were bound very strongly by TaMYB13 in in vitro DNA-binding assays, indicating that this gene was likely to be directly regulated by TaMYB13. These data suggested that Taγ-VPE was likely to be involved in maturation of fructosyltransferases in vacuoles in wheat.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/523, 050 filed 12 Aug. 2011, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4: 1087.
Altenbach et al. (2009) Plant Mol. Biol. 69:47-56.
Barnabas et al. (2008) Plant Cell Environ. 31:11-38.
Baumlein et al. (1992) Plant J. 2:233-239.
Bevan et al. (1983) Nucl. Acid Res. 11: 369-385.
Blacklow et al. (1984) Plant Sci. Lett. 36:213-218.
Bolouri-Moghaddam et al. (2010) FEBS J. 277:2022-2037.
Bonnett and Incoll (1992) Ann. Bot. 69:219-225.
Brandt et al. (1985) Carlsberg Res. Commun. 50:333-345.
Busk et al. (1997) The Plant Journal 11:1285-1295.

Cadwell and Joyce (1992) PCR Methods Appl. 2:28-33.
Capecchi (1980) Cell 22: 479-488
Chalmers et al. (2005) Plant Biotechnol. J. 3:459-474.
Chen et al. (2006) Plant Mol. Biol. 60:107-124.
Cheng et al. (1996) Plant Cell Rep. 15:653-657.
Cheng et al. (2010) Transgenic Res 19: 221-229.
Christensen & Quail (1989) Plant Molecular Biology 12:619-632.
Christensen et al. (1992) Plant Molecular Biology 18:675-689.
Clapp (1993) Clin. Perinatol. 20: 155-168.
Coco et al. (2001) Nature Biotechnology 19:354-359.
Coco et al. (2002) Nature Biotechnology 20:1246-1250.
Colot et al. (1987) EMBO J 6:3559-3564.
Comai et al. (2004) Plant J 37: 778-786.
Conley et al. (1994) Mol. Cell. Biol. 19: 2525-33.
Crameri et al. (1998) Nature 391:288-291.
Curiel et al. (1992) Hum. Gen. Ther. 3: 147-154.
Davies et al. (2005) Plant Cell Physiol 46: 1103-1115.
De Roover et al. (2000) Planta 210:808-814.
Del Viso et al. (2009) Plant Cell Physiol. 50:489-503.
Deyholos and Sieburth (2000) Plant Cell 12:1799-1810.
Dombrecht et al. (2007) Plant Cell 19:2225-2245.
Du et al. (2009) Biochemistry (Mosc). 74:1-11.
Eggert et al. (2005) Chembiochem 6:1062-1067.
Eglitis et al. (1988) Biotechniques 6: 608-614.
Feller et al. (2011) Plant J. 66:94-116.
Fujimura et al. (1985) Plant Tissue Cultural Letters 2: 74.
Gotor et al. (1993) Plant J. 3:509-518.
Graham et al. (1973) Virology 54: 536-539.
Grant et al. (1995) Plant Cell Rep. 15:254-258.
Grierson et al. (1994) Plant J. 5:815-26.
Hara-Nishimura et al. (1991) FEBS Lett 294:89-93.
Harayama (1998) Trends Biotechnol. 16: 76-82.
Hatton et al. (1995) Plant J. 7:859-876.
Hellinga (1997) Proc. Natl. Acad. Sci. 94(19):10015-10017.
Hendry (1993) New Phytol. 123:3-14.
Henikoff et al. (2004) Plant Physiol 135: 630-636.
Hinchee et al. (1988) Biotech. 6: 915.
Hisano et al. (2008) New Phytol. 178:766-780.
Housley (2000) Develop. Crop Sci. 26:207-222.
Huang et al. (1990) Plant Mol. Biol. 14:655-68.
Hwang et al. (1998) 36:331-41.
Incoll et al. (1989) Journal of Plant Physiology 134:196-202.
Irizarry et al. (2003) Biostatistics 4:249-264.
Jézéquel et al. (2008) Biotechniques 45:523-532.
Joshi (1987) Nucl. Acid Res. 15: 6643-6653.
Kam et al. (2008) Plant Mol. Biol. 67:305-322.
Kaur and Gupta (2002) J. Biosci. 27:703-714.
Kawakami and Yoshida (2002) Biosci. Biotechnol. Biochem. 66:2297-2305.
Kawakami and Yoshida (2005) Planta 223:90-104.
Kawakami et al. (2005) Gene 358:93-101.
Kawakami et al. (2008) J. Exp. Bot. 59:793-802.
Kooiker et al. (2005) Plant Cell 17:722-729.
Koroleva et al. (2001) Ann. Appl. Biol. 138:27-32.
Kusch et al. (2009) New Phytol. 184:127-140.
Kwon et al. (1994) Plant Physiol. 105: 357-367.
Lagudah et al. (2006) Theor. and Appl. Genet. 114: 21-30.
Langridge et al., (2001) Aust J Agric Res 52: 1043-1077
Lasseur et al. (2011) J. Exp. Bot. 62:1871-1885.
Last et al. (1991) Theor. Appl. Genet. 81:581-588.
Le Roy et al. (2007) Funct. Plant Biol. 34:972-983.
Lemieux (2000) Current Genomics 1: 301-311.
Leung et al. (1989) Technique 1:11-15.
Li et al. (2006) J. Exp. Bot. 57:1263-1273.
Liu et al. (1998) Plant Cell 10:1391-1406.
Livingston et al. (2009) Cell Mol. Life Sci. 66:2007-2023.
Lu et al. (1993) J. Exp. Med. 178: 2089-2096.
Lu et al. (2002) Plant Physiol. 130:1335-1348.
Maleux and Van den Ende (2007) J. Plant Biol. 50:671-680.
Martinez-Noel et al. (2001) Planta 213:640-646.
Martinez-Noel et al. (2006) Planta 225:183-191.
Martinez-Noel et al. (2007) Plant Physiol. Biochem. 45:410-419.
Martinez-Noel et al. (2009) Planta 230:1071-1079.
Martinez-Noel et al. (2010) Plant Signal Behav. 5:311-313.
Matsuoka et al. (1993) Proc. Natl. Acad. Sci. USA 90:9586-9590.
McElroy et al. (1990) Plant Cell 2:163-171.
Medberry et al. (1992) Plant Cell 4: 185-192.
Medberry et al. (1993) Plant J. 3: 619-626.
Mu et al. (2009) Cell Res. 19:1291-304.
Müller et al. (2000) Plant Physiol. 123:265-274.
Nagaraj et al. (2001) J. Plant Physiol. 158:1601-1607.
Nagaraj et al. (2004) New Phytol. 161:735-748.
Needleman and Wunsch (1970) J. Mol. Biol. 48:443-453.
Ness et al. (2002) Nature Biotechnology 20:1251-1255.
Niedz et al. (1995) Plant Cell Reports 14: 403-406.
Nomura et al. (2000) Plant Mol. Biol. 44: 99-106
Odell et al. (1985) Nature 313:810-812.
Orozco et al. (1993) Plant Mol. Biol. 23:1129-1138.
Ostermeiet et al. (1999) Nature Biotechnology 17:1205-1209.
Ow et al. (1986) Science 234: 856-859.
Patel et al. (2000) Mol. Breeding 6: 113-124.
Patzlaff et al. (2003a) Plant Mol. Biol. 53:597-608.
Patzlaff et al. (2003b) Plant J. 36:743-754.
Pellegrineschi et al. (2002) Genome 45:421-430.
Pérez-Rodriguez et al. (2010) Nucl. Acids Res. 38:D822-D827.
Perrin et al. (2000) Mol Breed 6:345-352.
Prasher et al. (1985) Biochem. Biophys. Res. Comm. 126: 1259-68.
Rao et al. (2011) et al. J. Plant Physiol. 168:344-351.
Rialio-Pachon et al. (2007) BMC Bioinformatics 8:42.
Ritsema and Smeekens (2003) Curr. Opin. Plant Biol. 6:223-230.
Ritsema et al. (2003) New Phytol. 160:61-67.
Ritsema et al. (2005) Plant Mol. Biol. 58:597-607.
Ritsema et al. (2009) PLoS ONE 4: e6605.
Ruuska (2006) Funct. Plant Biol. 33:799-809.
Ruuska (2008) Plant Mol. Biol. 66:15-32.
Sablowski et al. (1994) EMBO J. 13:128-137.
Schaffer and Petreikov (1997) Plant Physiol 113:739-746.
Schnyder (1993) New Phytol. 123:233-245.
Shaw et al. (2009) Funct. Integr. Genomics. 9:485-498.
Shimada et al. (2003) J. Biol. Chem. 278:32292-32299.
Sieber et al. (2001) Nature Biotechnology 19:456-460.
Slade and Knauf (2005) Transgenic Res. 14: 109-115.
Solano et al. (1995) EMBO J. 14:1773-1784.
Sprenger et al. (1995) Proc. Natl. Acad. Sci. USA 92:11652-11656.
Stahl et al. (2004) BMC Biotechnology 4:31
Stalker et al. (1988) Science 242: 419-423.
Stefanov et al. (1991) Acta Biologica Hungarica 42:323-330.
Stemmer (1994a) Proc. Natl. Acad. Sci. USA 91:10747-10751.
Stemmer (1994b) Nature 370:389-391.
Stephenson et al. (2007) Plant Mol. Biol. 65:77-92.
Stockhaus et al. (1987) Proc. Natl. Acad. Sci. USA 84:7943-7947.
Stockhaus et al. (1989) EMBO J. 8:2445-2451.

Thillet et al. (1988) J. Biol. Chem. 263: 12500.
Toriyama et al. (1986) Theor. Appl. Genet. 205: 34.
Triglia (2000) Methods Mot. Biol. 130:79-83.
Tungland and Meyer (2002) Comprehensive Reviews in Food Science and Food Safety 2:73-77. Valluru and Van den Ende (2008) J. Exp. Bot. 59:2905-2916.
Van den Ende and Valium (2009) J. Exp. Bot. 60:9-18.
Van den Ende et al. (2003) Plant Physiol. 131:621-631.
Van den Ende et al. (2005) New Phytol. 166:917-932.
Van den Ende et al. (2009) FEBS J. 276:5788-5798.
Van den Ende et al. (2011) Plant Physiol. 155:603-614.
Van Herwaarden et al. (1998) Aust. J. Agric. Res. 49:1095-1110.
Van Laere and Van den Ende (2002) Plant Cell Environ. 25:803-813.
Van Riet et al. (2006) J. Exp. Bot. 57:213-223.
Velten et al. (1984) EPBO J. 3:2733-2730.
Vickers et al. (2003) Plant Cell Rep. 22:135-1140.
Vijn and Smeekens (1999) Plant Physiol. 120: 351-360.
Vilardell et al. (1990) Plant Mol Biol 14:423-432.
Volkov et al. (1999) Nucleic acids research 27(18):e18.
Wagner et al. (1992) Proc. Natl. Acad. Sci. USA 89: 6099-6103.
Wardlaw and Willenbrink (2000) New Phytol. 148:413-422.
Wei and Chatterton (2001) J. Plant Physiol. 158:1203-1213.,
Wise et al. (1955) Analytical chemistry 27:33-36.
Xiao and Xue (2001) Plant Cell Rep. 20:667-673.
Xue et al. (1992) J. Gen. Microbiol. 138:2397-2403.
Xue et al. (1995) J. Biotechnol. 38:269-277.
Xue (2002a) Nucl. Acids Res. 30:e77.
Xue (2002b) Biochim. Biophys. Acta-Gene Struct. Expre. 1577:63-72.
Xue (2003) Plant J. 33:373-383.
Xue and Loveridge (2004) Plant J. 37:326-339.
Xue (2005) Plant J. 41:638-649.
Xue et al. (2006a) Funct Plant Biol. 33:43-57.
Xue et al. (2006b) Plant Mol. Biol. 61:863-881.
Xue et al. (2008a) Plant Mol. Biol. 67:197-214.
Xue et al. (2008b) Plant Physiol. 146: 441-454.
Xue et al. (2009) Crop Pasture Sci. 60:51-59.
Yamamoto et al. (1994) Plant Cell Physiol. 35: 73-778.
Yamamoto et al. (1997) Plant J. 1:255-265.
Yang et al. (1990) Proc. Natl. Acad. Sci. U.S.A. 87:4144-8.
Zaidi et al. (2005) Transgenic Res. 14:289-98.
Zhao et al. (1998) Nature Biotechnology 16:258-261.

The invention claimed is:

1. A process for producing flour, wholemeal, starch, a food product or a beverage product, comprising
   a) obtaining seed which comprises an exogenous polynucleotide which encodes a polypeptide with an amino acid sequence that is at least 90% identical to the full length amino acid sequence of any one of SEQ ID NOs 1-4 wherein the polynucleotide is operably linked to a promoter capable of directing expression of the polynucleotide in a cell of the plant; and
   b) processing the seed to produce the flour, wholemeal, starch, food product or beverage product.

2. The process of claim 1, wherein the exogenous polynucleotide encodes a polypeptide with an amino acid sequence that is at least 95% identical to the full length amino acid sequence of any one of SEQ ID NOs 1-4.

3. The process of claim 1, wherein the food product is selected from the group consisting of bread, pasta, noodles, breakfast cereal, snack food, cake, pastry and a food containing a flour-based sauce.

4. The process of claim 1, wherein the beverage product is beer or malt.

5. The process of claim 2, wherein the exogenous polynucleotide encodes a polypeptide with an amino acid sequence that is at least 95% identical to the full length amino acid sequence of SEQ ID NO 1.

6. The process of claim 2, wherein the exogenous polynucleotide encodes a polypeptide with an amino acid sequence that is at least 95% identical to the full length amino acid sequence of SEQ ID NO 2.

7. The process of claim 2, wherein the exogenous polynucleotide encodes a polypeptide with an amino acid sequence that is at least 95% identical to the full length amino acid sequence of SEQ ID NO 3.

8. The process of claim 2, wherein the exogenous polynucleotide encodes a polypeptide with an amino acid sequence that is at least 95% identical to the full length amino acid sequence of SEQ ID NO 4.

* * * * *